US008212052B2

(12) United States Patent
Choi et al.

(10) Patent No.: US 8,212,052 B2
(45) Date of Patent: *Jul. 3, 2012

(54) DUAL-ACTING BENZOIMIDAZOLE ANTIHYPERTENSIVE AGENTS

(75) Inventors: Seok-Ki Choi, Ann Arbor, MI (US); Paul R. Fatheree, San Francisco, CA (US); Robert Murray McKinnell, Half Moon Bay, CA (US); Brooke Olson, San Francisco, CA (US)

(73) Assignee: Theravance, Inc., South San Francisco, CA (US)

( * ) Notice: Subject to any disclaimer, the term of this patent is extended or adjusted under 35 U.S.C. 154(b) by 590 days.

This patent is subject to a terminal disclaimer.

(21) Appl. No.: 12/330,289

(22) Filed: Dec. 8, 2008

(65) Prior Publication Data

US 2009/0149521 A1      Jun. 11, 2009

Related U.S. Application Data

(60) Provisional application No. 61/007,129, filed on Dec. 11, 2007.

(51) Int. Cl.
*A61K 31/4184* (2006.01)
*C07D 235/08* (2006.01)
(52) U.S. Cl. .................... 548/304.4; 514/394
(58) Field of Classification Search .............. 548/304.4
See application file for complete search history.

(56) References Cited

U.S. PATENT DOCUMENTS

| | | | |
|---|---|---|---|
| 4,513,009 A | 4/1985 | Roques et al. |
| 4,610,816 A | 9/1986 | Berger |
| 4,722,810 A | 2/1988 | Delaney et al. |
| 4,929,641 A | 5/1990 | Haslanger et al. |
| 5,030,654 A | 7/1991 | Barnish et al. |
| 5,138,069 A | 8/1992 | Carini et al. |
| 5,155,100 A | 10/1992 | Erion et al. |
| 5,217,996 A | 6/1993 | Ksander |
| 5,270,317 A | 12/1993 | Bernhart et al. |
| 5,294,632 A | 3/1994 | Erion et al. |
| 5,399,578 A | 3/1995 | Buhlmayer et al. |
| 5,508,272 A | 4/1996 | Robl |
| 5,587,375 A | 12/1996 | Robl |
| 5,591,762 A | 1/1997 | Hauel et al. |
| 5,616,599 A | 4/1997 | Yanagisawa et al. |
| 5,705,517 A | 1/1998 | Naka et al. |
| 5,864,043 A | 1/1999 | Narr et al. |
| 6,602,866 B2 | 8/2003 | Flynn et al. |
| 6,777,443 B2 | 8/2004 | Fink |
| 6,852,745 B2 | 2/2005 | Murugesan et al. |
| 7,060,721 B1 | 6/2006 | Oku et al. |
| 2003/0144215 A1 | 7/2003 | Ksander et al. |
| 2006/0046978 A1 | 3/2006 | Pierau et al. |
| 2008/0188533 A1 | 8/2008 | Choi et al. |
| 2008/0269305 A1 | 10/2008 | Allegretti et al. |
| 2008/0318951 A1* | 12/2008 | Allegretti et al. .......... 514/234.5 |

FOREIGN PATENT DOCUMENTS

| | | |
|---|---|---|
| EP | 0 361 365 A1 | 4/1990 |
| EP | 0437103 A2 | 7/1991 |
| EP | 0505954 A1 | 9/1992 |
| EP | 0 726 072 A2 | 8/1996 |
| JP | 06 184086 | 7/1994 |
| JP | 07 048360 | 2/1995 |
| JP | 2003 048874 | 2/2003 |
| WO | WO 92/13564 | 8/1992 |
| WO | WO 00/01389 A2 | 1/2000 |
| WO | WO 2006/027680 A1 | 3/2006 |
| WO | WO 2006/086456 A2 | 8/2006 |
| WO | WO 2007/045663 A2 | 4/2007 |
| WO | WO 2007/056546 A1 | 5/2007 |
| WO | WO 2007/106708 A2 | 9/2007 |
| WO | WO 2007/109456 A2 | 9/2007 |
| WO | WO 2008/142576 A2 | 11/2008 |

OTHER PUBLICATIONS

Middlemiss et al., "Benzofuran based angiotensin II antagonists related to GR117289: Part II; amino acid amides", Bioorganic & Medicinal Chemistry Letters, vol. 3, No. 10, pp. 2043-2046 (1993).
International Search Report for PCT/US2008/085868, Aug. 12, 2008.
Shah et al., "Angiotensin II—AT$_1$ Receptor Antagonist: design, synthesis and evaluation of substituted carboxamido benzoimidazole derivatives", European Journal of Medicinal Chemistry, 43(9), pp. 1808-1812 (2008).
Fournie-Zaluski et al., "Design of Orally Active Dual Inhibitors of Neutral Endopeptidase and Angiotensin-Converting Enzyme with long Duration of Action" Journal of Medicinal Chemistry 39:2594-2608 (1996).
U.S. Appl. No. 12/148,842 filed Apr. 23, 2008, Allegretti et al.
U.S. Appl. No. 12/156,695, filed Jun. 4, 2008, Allegretti et al.
U.S. Appl. No. 12/231,858, filed Sep. 5, 2008, Choi et al.

OTHER PUBLICATIONS

Gardiner et al., "Regional hemodynamic effects of neutral endopeptidase inhibition and angiotensin (AT1) receptor antagonism alone or in combination in conscious spontaneously hypertensive rats", The Journal of Pharmacology and Experimental Therapeutics, vol. 319 No. 1, pp. 340-348 (2006).

(Continued)

Primary Examiner — Laura L. Stockton
(74) Attorney, Agent, or Firm — Jeffrey A. Hagenah; Shelley Eberle

(57) ABSTRACT

The invention relates to compounds having the formula:

(I)

wherein Ar, r, n, X, $R^2$, $R^{2'}$, $R^3$, and $R^{5-7}$ are as defined in the specification, or a pharmaceutically acceptable salt thereof. These compounds have $AT_1$ receptor antagonist activity and neprilysin inhibition activity. The invention also relates to pharmaceutical compositions comprising such compounds; methods of using such compounds; and a process and intermediates for preparing such compounds.

23 Claims, No Drawings

OTHER PUBLICATIONS

Pu et al., "The effect of combined AT1 receptor antagonist and neutral endopeptidase (NEP) inhibitor compared to the dual angiotensin converting enzyme inhibitor/NEP on endothelial function and vascular remodeling of SHRSP", Abstract presented at the Canadian Cardiovascular Congress (Oct. 2004).

Robl et al., "Recent advances in the design and development of vasopeptidase inhibitors", Expert Opinion on Therapeutic Patents, 9(12), pp. 1665-1677 (1999).

Ashton et al., "Nonpeptide Angiotensin II Antagonists Derived from 4H-1,2,4-triazoles and 3H-Imidazo[1,2-b][1,2,4] triazoles", J. Med. Chem., 36, 591-609 (1993).

U.S. Appl. No. 12/431,056, filed Apr. 28, 2009, Allegretti et al.

U.S. Appl. No. 12/507,995, filed Jul. 23, 2009, Choi et al.

\* cited by examiner

DUAL-ACTING BENZOIMIDAZOLE ANTIHYPERTENSIVE AGENTS

CROSS-REFERENCE TO RELATED APPLICATIONS

This application claims the benefit of U.S. Provisional Application No. 61/007,129, filed on Dec. 11, 2007; the disclosure of which is incorporated herein by reference in its entirety.

BACKGROUND OF THE INVENTION

1. Field of the Invention

The present invention relates to novel compounds having angiotensin II type 1 ($AT_1$) receptor antagonist activity and neprilysin-inhibition activity. The invention also relates to pharmaceutical compositions comprising such compounds, processes and intermediates for preparing such compounds and methods of using such compounds to treat diseases such as hypertension.

2. State of the Art

The aim of antihypertensive therapy is to lower blood pressure and prevent hypertension-related complications such as myocardial infarction, stroke, and renal disease. For patients with uncomplicated hypertension (i.e., no risk factors, target organ damage, or cardiovascular disease), it is hoped that reducing blood pressure will prevent development of cardiovascular and renal comorbidities, conditions that exist at the same time as the primary condition in the same patient. For those patients with existing risk factors or comorbidities, the therapeutic target is the slowing of comorbid disease progression and reduced mortality.

Physicians generally prescribe pharmacological therapies for patients whose blood pressure cannot be adequately controlled by dietary and/or lifestyle modifications. Commonly used therapeutic classes act to promote diuresis, adrenergic inhibition, or vasodilation. A combination of drugs is often prescribed, depending upon what comorbidities are present.

There are five common drug classes used to treat hypertension: diuretics, which include thiazide and thiazide-like diuretics such as hydrochlorothiazide, loop diuretics such as furosemide, and potassium-sparing diuretics such as triamterene; $\beta_1$ adrenergic receptor blockers such as metoprolol succinate and carvedilol; calcium channel blockers such as amlodipine; angiotensin-converting enzyme (ACE) inhibitors such as captopril, benazepril, enalapril, enalaprilat, lisinopril, quinapril, and ramipril; and $AT_1$ receptor antagonists, also known as angiotensin II type 1 receptor blockers (ARBs), such as candesartan cilexetil, eprosartan, irbesartan, losartan, olmesartan medoxomil, telmisartan, and valsartan. Combinations of these drugs are also administered, for example, a calcium channel blocker (amlodipine) and an ACE inhibitor (benazepril), or a diuretic (hydrochlorothiazide) and an ACE inhibitor (enalapril). All of these drugs, when used appropriately, are effective in the treatment of hypertension. Nevertheless, both efficacy and tolerability should be further improved in new drugs targeting hypertension. Despite the availability of many treatment options, the recent National Health And Nutrition Examination Survey (NHANES) demonstrated that only about 50% of all treated patients with hypertension achieve adequate blood pressure control. Furthermore, poor patient compliance due to tolerability issues with available treatments further reduces treatment success.

In addition, each of the major classes of antihypertensive agents have some drawbacks. Diuretics can adversely affect lipid and glucose metabolism, and are associated with other side effects, including orthostatic hypotension, hypokalemia, and hyperuricemia. Beta blockers can cause fatigue, insomnia, and impotence; and some beta blockers can also cause reduced cardiac output and bradycardia, which may be undesirable in some patient groups. Calcium channel blockers are widely used but it is debatable as to how effectively these drugs reduce fatal and nonfatal cardiac events relative to other drug classes. ACE inhibitors can cause coughing, and rarer side effects include rash, angioedema, hyperkalemia, and functional renal failure. $AT_1$ receptor antagonists are equally effective as ACE inhibitors but without the high prevalence of cough.

Neprilysin (neutral endopeptidase, EC 3.4.24.11) (NEP), is an endothelial membrane bound $Zn^{2+}$ metallopeptidase found in many tissues, including the brain, kidney, lungs, gastrointestinal tract, heart, and peripheral vasculature. NEP is responsible for the degradation and inactivation of a number of vasoactive peptides, such as circulating bradykinin and angiotensin peptides, as well as the natriuretic peptides, the latter of which have several effects including vasodilation and diuresis. Thus, NEP plays an important role in blood pressure homeostasis. NEP inhibitors have been studied as potential therapeutics, and include thiorphan, candoxatril, and candoxatrilat. In addition, compounds have also been designed that inhibit both NEP and ACE, and include omapatrilat, gempatrilat, and sampatrilat. Referred to as vasopeptidase inhibitors, this class of compounds are described in Robl et al (1999) *Exp. Opin. Ther. Patents* 9(12): 1665-1677.

There may be an opportunity to increase anti-hypertensive efficacy when combining $AT_1$ receptor antagonism and NEP inhibition, as evidenced by $AT_1$ receptor antagonist/NEP inhibitor combinations described in WO 9213564 to Darrow et al. (Schering Corporation); US20030144215 to Ksander et al.; Pu et al., Abstract presented at the Canadian Cardiovascular Congress (October 2004); and Gardiner et al. (2006) *JPET* 319:340-348; and WO 2007/045663 (Novartis AG) to Glasspool et al.

Recently, WO 2007/056546 (Novartis AG) to Feng et al. has described complexes of an $AT_1$ receptor antagonist and a NEP inhibitor, where an $AT_1$ receptor antagonist compound is non-covalently bound to a NEP inhibitor compound, or where the antagonist compound is linked to the inhibitor compound by a cation.

In spite of the advances in the art, there remains a need for a highly efficacious monotherapy with multiple mechanisms of action leading to levels of blood pressure control that can currently only be achieved with combination therapy. Thus, although various hypertensive agents are known, and administered in various combinations, it would be highly desirable to provide compounds having both $AT_1$ receptor antagonist activity and NEP inhibition activity in the same molecule. Compounds possessing both of these activities are expected to be particularly useful as therapeutic agents since they would exhibit antihypertensive activity through two independent modes of action while having single molecule pharmacokinetics.

In addition, such dual-acting compounds are also expected to have utility to treat a variety of other diseases that can be treated by antagonizing the $AT_1$ receptor and/or inhibiting the NEP enzyme.

SUMMARY OF THE INVENTION

The present invention provides novel compounds that have been found to possess $AT_1$ receptor antagonist activity and neprilysin (NEP) enzyme inhibition activity. Accordingly, compounds of the invention are expected to be useful and advantageous as therapeutic agents for treating conditions such as hypertension and heart failure.

One aspect of the invention relates to a compound of formula I:

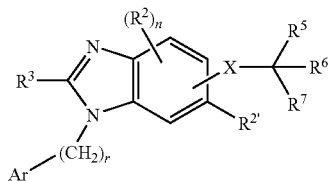

wherein:
r is 0, 1 or 2;
Ar is an aryl group selected from:

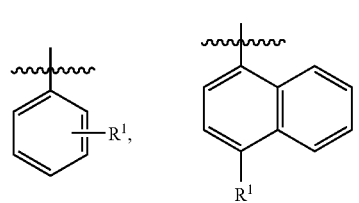

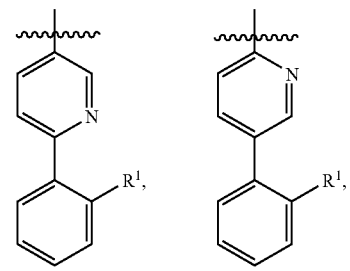

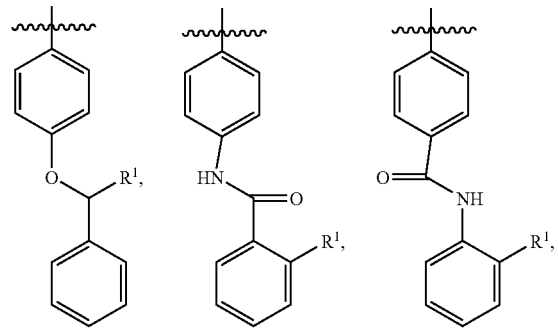

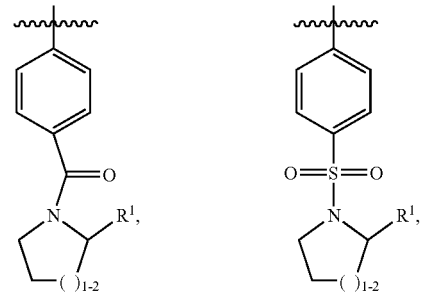

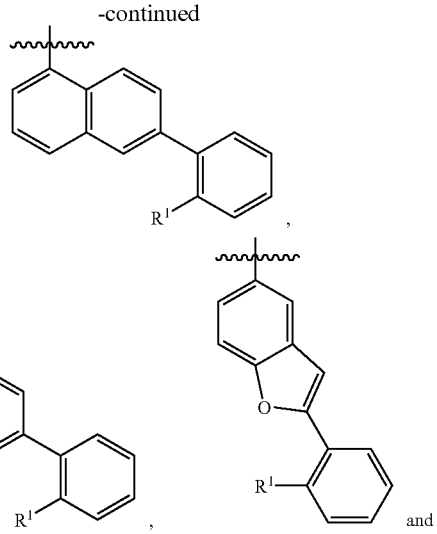

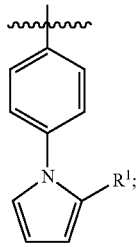

$R^1$ is selected from —COOR$^{1a}$, —NHSO$_2$R$^{1b}$, —SO$_2$NHR$^{1d}$, —SO$_2$OH, —C(O)NH—SO$_2$R$^{1c}$, —P(O)(OH)$_2$, —CN, —OCH(R$^{1e}$)—COOH, tetrazol-5-yl,

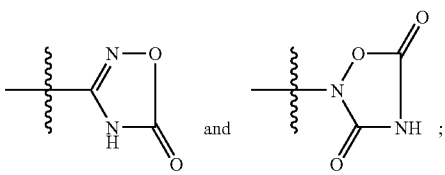

$R^{1a}$ is H, —C$_{1-6}$alkyl, —C$_{1-3}$alkylenearyl, —C$_{1-3}$alkylene-heteroaryl, —C$_{3-7}$cycloalkyl, —CH(C$_{1-4}$alkyl)OC(O)R$^{1aa}$, —C$_{0-6}$alkylenemorpholine,

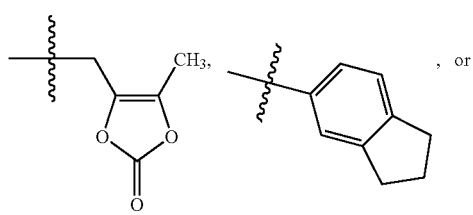

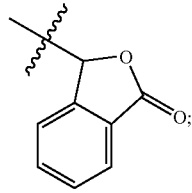

$R^{1aa}$ is —O—C$_{1-6}$alkyl, —O—C$_{3-7}$cycloalkyl, —NR$^{1ab}$R$^{1ac}$, or —CH(NH$_2$)CH$_2$COOCH$_3$; R$^{1ab}$ and R$^{1ac}$ are independently H, —C$_{1-6}$alkyl, or benzyl, or are taken together as —(CH$_2$)$_{3-6}$—; R$^{1b}$ is R$^{1c}$ or —NHC(O)R$^{1c}$; R$^{1c}$ is —C$_{1-6}$alkyl, —C$_{0-6}$alkylene-O—R$^{1ca}$, —C$_{1-5}$alkylene-NR$^{1cb}$R$^{1cc}$, —C$_{0-4}$alkylenearyl, or —C$_{0-4}$alkyleneheteroaryl; R$^{1ca}$ is H, —C$_{1-6}$alkyl, or —C$_{1-6}$alkylene-O—C$_{1-6}$alkyl; R$^{1cb}$ and R$^{1cc}$ are independently H or —C$_{1-6}$alkyl, or are taken together as —(CH$_2$)$_2$—O—(CH$_2$)$_2$— or —(CH$_2$)$_2$—N[C(O)CH$_3$]—(CH$_2$)$_2$—; R$^{1d}$ is H, R$^{1c}$, —C(O)R$^{1c}$, or —C(O)NHR$^{1c}$; R$^{1e}$ is —C$_{1-4}$alkyl or aryl;

n is 0, 1, 2 or 3;

each R$^2$ is independently selected from halo, —NO$_2$, —C$_{1-6}$ alkyl, —C$_{2-6}$alkenyl, —C$_{3-7}$cycloalkyl, —CN, —C(O)R$^{2a}$, —C$_{0-5}$alkylene-OR$^{2b}$, —C$_{0-5}$alkylene-NR$^{2c}$R$^{2d}$, —C$_{0-3}$alkylenearyl, and —C$_{0-3}$alkyleneheteroaryl; R$^{2a}$ is H, —C$_{1-6}$alkyl, —C$_{3-7}$cycloalkyl, —OR$^{2b}$, or —NR$^{2c}$R$^{2d}$; R$^{2b}$ is H, —C$_{1-6}$alkyl, —C$_{3-7}$cycloalkyl, or —C$_{0-1}$alkylenearyl; and R$^{2c}$ and R$^{2d}$ are independently H, —C$_{1-4}$alkyl, or —C$_{0-1}$alkylenearyl;

R$^{2'}$ is selected from H and R$^2$;

R$^3$ is selected from —C$_{1-10}$alkyl, —C$_{2-10}$alkenyl, —C$_{3-10}$alkynyl, —C$_{0-3}$alkylene-C$_{3-7}$cycloalkyl, —C$_{2-3}$alkenylene-C$_{3-7}$cycloalkyl, —C$_{2-3}$alkynylene-C$_{3-7}$cycloalkyl, —C$_{0-5}$alkylene-NR$^{3a}$—C$_{0-5}$alkylene-R$^{3b}$, —C$_{0-5}$alkylene-O—C$_{0-5}$alkylene-R$^{3b}$, —C$_{1-5}$alkylene-S—C$_{1-5}$alkylene-R$^{3b}$, and —C$_{0-3}$alkylenearyl; R$^{3a}$ is H, —C$_{1-6}$alkyl, —C$_{3-7}$cycloalkyl, or —C$_{0-3}$alkylenearyl; and R$^{3b}$ is H, —C$_{1-6}$alkyl, —C$_{3-7}$cycloalkyl, —C$_{2-4}$alkenyl, —C$_{2-4}$alkynyl, or aryl;

X is —C$_{1-12}$alkylene-, where at least one —CH$_2$— moiety in the alkylene is replaced with a —NR$^{4a}$—C(O)— or —C(O)—NR$^{4a}$— moiety, where R$^{4a}$ is H, —OH, or —C$_{1-4}$alkyl;

R$^5$ is selected from —C$_{0-3}$alkylene-SR$^{5a}$, —C$_{0-3}$alkylene-C(O)NR$^{5b}$R$^{5c}$, —C$_{0-3}$alkylene-NR$^{5b}$—C(O)R$^{5d}$, —NH—C$_{0-1}$alkylene-P(O)(OR$^{5e}$)$_2$, —C$_{0-3}$alkylene-P(O)OR$^{5e}$R$^{5f}$, —C$_{0-2}$alkylene-CHR$^{5g}$COOH, —C$_{0-3}$alkylene-C(O)NR$^{5h}$—CHR$^{5i}$—COOH, and —C$_{0-3}$alkylene-S—SR$^{5j}$; R$^{5a}$ is H or —C(O)—R$^{5aa}$; R$^{5aa}$ is —C$_{1-6}$alkyl, —C$_{0-6}$alkylene-C$_{3-7}$cycloalkyl, —C$_{0-6}$alkylenearyl, —C$_{0-6}$alkyleneheteroaryl, —C$_{0-6}$alkylenemorpholine, —C$_{0-6}$alkylenepiperazine-CH$_3$, —CH[N(R$^{5ab}$)$_2$]-aa where aa is an amino acid side chain, -2-pyrrolidine, —C$_{0-6}$alkylene-OR$^{5ab}$, —OC$_{0-6}$alkylenearyl, —C$_{1-2}$alkylene-OC(O)—C$_{1-6}$alkyl, —C$_{1-2}$alkylene-OC(O)—C$_{0-6}$alkylenearyl, or —C$_{1-2}$alkylene-OC(O)—OC$_{1-6}$alkyl; R$^{5ab}$ is independently H or —C$_{1-6}$alkyl; R$^{5b}$ is H, —OH, —OC(O)R$^{5ba}$, —CH$_2$COOH, —O-benzyl, -pyridyl, or —OC(S)NR$^{5bb}$R$^{5bc}$; R$^{5ba}$ is H, —C$_{1-6}$alkyl, aryl, —OCH$_2$-aryl, —CH$_2$O-aryl, or —NR$^{5bb}$R$^{5bc}$; R$^{5bb}$ and R$^{5bc}$ are independently H or —C$_{1-4}$alkyl; R$^{5c}$ is H, —C$_{1-6}$alkyl, or —C(O)—R$^{5ca}$; R$^{5ca}$ is H, —C$_{1-6}$alkyl, —C$_{3-7}$cycloalkyl, aryl, or heteroaryl; R$^{5d}$ is H, —C$_{1-4}$alkyl, —C$_{0-3}$alkylenearyl, —NR$^{5da}$R$^{5db}$, —CH$_2$SH, or —O—C$_{1-6}$alkyl; R$^{5da}$ and R$^{5db}$ are independently H or —C$_{1-4}$alkyl; R$^{5e}$ is H, —C$_{1-6}$alkyl, —C$_{1-3}$alkylenearyl, —C$_{1-3}$alkyleneheteroaryl, —C$_{3-7}$cycloalkyl, —CH(CH$_3$)OC(O)R$^{5ea}$,

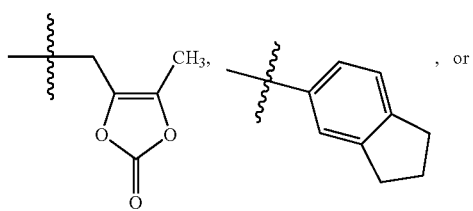

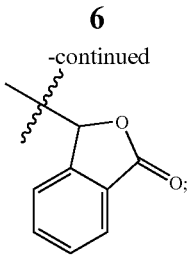

R$^{5ea}$ is —O—C$_{1-6}$alkyl, —O—C$_{3-7}$cycloalkyl, —NR$^{5eb}$R$^{5ec}$, or —CH(NH$_2$)CH$_2$COOCH$_3$; R$^{5eb}$ and R$^{5ec}$ are independently H, —C$_{1-4}$alkyl, or —C$_{1-3}$alkylenearyl, or are taken together as —(CH$_2$)$_{3-6}$—; R$^{5f}$ is H, —C$_{1-4}$alkyl, —C$_{0-3}$alkylenearyl, —C$_{1-3}$alkylene-NR$^{5fa}$R$^{5fb}$, or —C$_{1-3}$alkylene(aryl)-C$_{0-3}$alkylene-NR$^{5fa}$R$^{5fb}$; R$^{5fa}$ and R$^{5fb}$ are independently H or —C$_{1-4}$alkyl; R$^{5g}$, is H, —C$_{1-6}$alkyl, —C$_{1-3}$ alkylenearyl, or —CH$_2$—O—(CH$_2$)$_2$—OCH$_3$; R$^{5h}$ is H or —C$_{1-4}$alkyl; and R$^{5i}$ is H, —C$_{1-14}$alkyl, or —C$_{0-3}$alkylenearyl; and R$^{5j}$ is —C$_{1-6}$alkyl, aryl, or —CH$_2$CH(NH$_2$)COOH;

R$^6$ is selected from —C$_{1-6}$alkyl, —CH$_2$O(CH$_2$)$_2$OCH$_3$, —C$_{1-6}$alkylene-O—C$_{1-6}$alkyl, —C$_{0-3}$alkylenearyl, —C$_{0-3}$alkyleneheteroaryl, and —C$_{0-3}$alkylene-C$_{3-7}$cycloalkyl; and R$^7$ is H or is taken together with R$^6$ to form —C$_{3-8}$cycloalkyl;

wherein each —CH$_2$— group in —(CH$_2$)$_r$— is optionally substituted with 1 or 2 substituents independently selected from —C$_{1-4}$alkyl and fluoro;

each carbon atom in the alkylene moiety in X is optionally substituted with one or more R$^{4b}$ groups and one —CH$_2$— moiety in X may be replaced with a group selected from —C$_{4-8}$cycloalkylene-, —CR$^{4d}$=CH—, and —CH=CR$^{4d}$—; R$^{4b}$ is —C$_{0-5}$alkylene-COOR$^{4c}$, —C$_{1-6}$alkyl, —C$_{0-1}$alkylene-CONH$_2$, —C$_{1-2}$alkylene-OH, —C$_{0-3}$alkylene-C$_{3-7}$cycloalkyl, 1H-indol-3-yl, benzyl, or hydroxybenzyl; R$^{4c}$ is H or —C$_{1-4}$alkyl; and R$^{4d}$ is —CH$_2$-thiophene or phenyl;

each alkyl and each aryl in R$^1$, R$^2$, R$^{2'}$, R$^3$, R$^{4a-4d}$, and R$^{5-6}$ is optionally substituted with 1 to 7 fluoro atoms;

each ring in Ar and each aryl and heteroaryl in R$^1$, R$^2$, R$^{2'}$, R$^3$, and R$^{5-6}$ is optionally substituted with 1 to 3 substituents independently selected from —OH, —C$_{1-6}$alkyl, —C$_{2-4}$alkenyl, —C$_{2-4}$alkynyl, —CN, halo, —O—C$_{1-6}$alkyl, —S—C$_{1-6}$ alkyl, —S(O)—C$_{1-6}$alkyl, —S(O)$_2$—C$_{1-4}$alkyl, -phenyl, —NO$_2$, —NH$_2$, —NH—C$_{1-6}$alkyl, and —N(C$_{1-6}$alkyl)$_2$, wherein each alkyl, alkenyl and alkynyl is optionally substituted with 1 to 5 fluoro atoms;

or a pharmaceutically acceptable salt thereof.

Another aspect of the invention relates to pharmaceutical compositions comprising a pharmaceutically acceptable carrier and a compound of the invention. Such compositions may optionally contain other therapeutic agents such as diuretics, β$_1$ adrenergic receptor blockers, calcium channel blockers, angiotensin-converting enzyme inhibitors, AT$_1$ receptor antagonists, neprilysin inhibitors, non-steroidal anti-inflammatory agents, prostaglandins, anti-lipid agents, anti-diabetic agents, anti-thrombotic agents, renin inhibitors, endothelin receptor antagonists, endothelin converting enzyme inhibitors, aldosterone antagonists, angiotensin-converting enzyme/neprilysin inhibitors, vasopressin receptor antagonists, and combinations thereof. Accordingly, in yet another aspect of the invention, a pharmaceutical composition comprises a compound of the invention, a second therapeutic agent, and a pharmaceutically acceptable carrier. Another aspect of the invention relates to a combination of active agents, comprising a compound of the invention and a second therapeutic agent. The compound of the invention can be formulated together or separately from the additional agent(s). When formulated separately, a pharmaceutically acceptable carrier may be included with the additional agent(s). Thus, yet another aspect of the invention relates to a combination of pharmaceutical compositions, the combination comprising: a first pharmaceutical composition comprising a compound of the invention and a first pharmaceutically acceptable carrier; and a second pharmaceutical composition comprising a second therapeutic agent and a second pharmaceutically acceptable carrier. The invention also relates to a kit containing such pharmaceutical compositions, for example where the first and second pharmaceutical compositions are separate pharmaceutical compositions.

Compounds of the invention possess both $AT_1$ receptor antagonist activity and NEP enzyme inhibition activity, and are therefore expected to be useful as therapeutic agents for treating patients suffering from a disease or disorder that is treated by antagonizing the $AT_1$ receptor and/or inhibiting the NEP enzyme. Thus, one aspect of the invention relates to a method of treating patients suffering from a disease or disorder that is treated by antagonizing the $AT_1$ receptor and/or inhibiting the NEP enzyme, comprising administering to a patient a therapeutically effective amount of a compound of the invention. Another aspect of the invention relates to a method of treating hypertension or heart failure, comprising administering to a patient a therapeutically effective amount of a compound of the invention. Still another aspect of the invention relates to a method for antagonizing an $AT_1$ receptor in a mammal comprising administering to the mammal, an $AT_1$ receptor-antagonizing amount of a compound of the invention. Yet another aspect of the invention relates to a method for inhibiting a NEP enzyme in a mammal comprising administering to the mammal, a NEP enzyme-inhibiting amount of a compound of the invention.

Compounds of the invention that are of particular interest include those that exhibit an inhibitory constant ($pK_i$) for binding to an $AT_1$ receptor greater than or equal to about 5.0; in particular those having a $pK_i$ greater than or equal to about 6.0; in one embodiment those having a $pK_i$ greater than or equal to about 7.0; more particularly those having a $pK_i$ greater than or equal to about 8.0; and in yet another embodiment, those having a $pK_i$ within the range of about 8.0-10.0. Compounds of particular interest also include those having a NEP enzyme inhibitory concentration ($pIC_{50}$) greater than or equal to about 5.0; in one embodiment those having a $pIC_{50}$ greater than or equal to about 6.0; in particular those having a $pIC_{50}$ greater than or equal to about 7.0; and most particularly those having a $pIC_{50}$ within the range of about 7.0-10.0. Compounds of further interest include those having a $pK_i$ for binding to an $AT_1$ receptor greater than or equal to about 7.5 and having a NEP enzyme $pIC_{50}$ greater than or equal to about 7.0.

Since compounds of the invention possess $AT_1$ receptor antagonist activity and NEP inhibition activity, such compounds are also useful as research tools. Accordingly, one aspect of the invention relates to a method of using a compound of the invention as a research tool, the method comprising conducting a biological assay using a compound of the invention. Compounds of the invention can also be used to evaluate new chemical compounds. Thus another aspect of the invention relates to a method of evaluating a test compound in a biological assay, comprising: (a) conducting a biological assay with a test compound to provide a first assay value; (b) conducting the biological assay with a compound of the invention to provide a second assay value; wherein step (a) is conducted either before, after or concurrently with step (b); and (c) comparing the first assay value from step (a) with the second assay value from step (b). Exemplary biological assays include an $AT_1$ receptor binding assay and a NEP enzyme inhibition assay. Still another aspect of the invention relates to a method of studying a biological system or sample comprising an $AT_1$ receptor, a NEP enzyme, or both, the method comprising: (a) contacting the biological system or sample with a compound of the invention; and (b) determining the effects caused by the compound on the biological system or sample.

The invention also relates to processes and intermediates useful for preparing compounds of the invention. In one aspect of the invention novel intermediates have formula III, IV, or V.

Yet another aspect of the invention relates to the use of a compound of formula I or a pharmaceutically acceptable salt thereof, for the manufacture of a medicament, especially for the manufacture of a medicament useful for treating hypertension or acute decompensated heart failure. Another aspect of the invention relates to use of a compound of the invention for antagonizing an $AT_1$ receptor or for inhibiting a NEP enzyme in a mammal. Still another aspect of the invention relates to the use of a compound of the invention as a research tool. Other aspects and embodiments of the invention are disclosed herein.

DETAILED DESCRIPTION OF THE INVENTION

The invention relates to compounds of formula I:

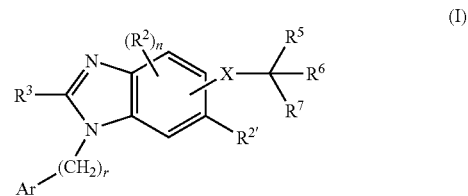

(I)

and pharmaceutically acceptable salts thereof.

As used herein, the term "compound of the invention" includes all compounds encompassed by formula I such as the species embodied in formulas Ia, Ib, Ic, II, IIa, IIb, IIc, III, IV, and V, described below. In addition, the compounds of the invention may also contain several basic or acidic groups (e.g., amino or carboxyl groups) and therefore, such compounds can exist as a free base, free acid, or in various salt forms. All such salt forms are included within the scope of the invention. Finally, the compounds of the invention may also exist as prodrugs. Accordingly, those skilled in the art will recognize that reference to a compound herein, for example, reference to a "compound of the invention" or a "compound of formula I" includes a compound of formula I as well as pharmaceutically acceptable salts and prodrugs of that compound unless otherwise indicated. Further, the term "or a pharmaceutically acceptable salt and/or prodrug thereof" is intended to include all permutations of salts and prodrugs, such as a pharmaceutically acceptable salt of a prodrug. Furthermore, solvates of compounds of formula I or salts thereof are included within the scope of the invention.

The compounds of formula I may contain one or more chiral centers and therefore, these compounds may be prepared and used in various stereoisomeric forms. Accordingly, the invention relates to racemic mixtures, pure stereoisomers (i.e., enantiomers or diastereomers), stereoisomer-enriched mixtures, and the like unless otherwise indicated. When a chemical structure is depicted herein without any stereochemistry, it is understood that all possible stereoisomers are encompassed by such structure. Thus, for example, the term "compound of formula I" is intended to include all possible stereoisomers of the compound. Similarly, when a particular stereoisomer is shown or named herein, it will be understood by those skilled in the art that minor amounts of other stereoisomers may be present in the compositions of the invention unless otherwise indicated, provided that the utility of the composition as a whole is not eliminated by the presence of such other isomers. Individual enantiomers may be obtained by numerous methods that are well known in the art, including chiral chromatography using a suitable chiral stationary phase or support, or by chemically converting them into diastereomers, separating the diastereomers by conventional means such as chromatography or recrystallization, then regenerating the original enantiomers. Additionally, where applicable, all cis-trans or E/Z isomers (geometric isomers), tautomeric forms and topoisomeric forms of the compounds of the invention are included within the scope of the invention unless otherwise specified.

One possible chiral center could be present in the X portion of the compound. For example, a chiral center exists at a carbon atom in the alkylene moiety in X that is substituted with an $R^{4b}$ group such as —$C_{1-6}$alkyl, for example —$CH_3$. This chiral center is present at the carbon atom indicated by the symbol * in the following partial formula:

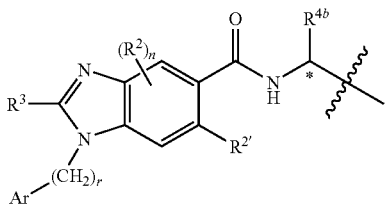

Another possible chiral center could be present in the —$CR^5R^6R^7$ portion of the compound, when $R^6$ is a group such as —$C_{1-6}$alkyl, for example —$CH_2CH(CH_3)_2$, and $R^7$ is H. This chiral center is present at the carbon atom indicated by the symbol ** in the following formula:

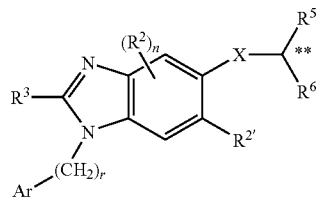

In one embodiment of the invention, the carbon atom identified by the symbol * and/or ** has the (R) configuration. In this embodiment, compounds of formula I have the (R) configuration at the carbon atom identified by the symbol * and/or ** or are enriched in a stereoisomeric form having the (R) configuration at this carbon atom (or atoms). In another embodiment, the carbon atom identified by the symbol * and/or ** has the (S) configuration. In this embodiment, compounds of formula I have the (S) configuration at the carbon atom identified by the symbol * and/or ** or are enriched in a stereoisomeric form having the (S) configuration at this carbon atom. It is understood that a compound may have a chiral center at both the * and the ** carbon atoms. In such cases, four possible diastereomers can exist. In some cases, in order to optimize the therapeutic activity of the compounds of the invention, e.g., as hypertensive agents, it may be desirable that the carbon atom identified by the symbol * and/or ** have a particular (R) or (S) configuration.

The compounds of the invention, as well as those compounds used in their synthesis, may also include isotopically-labeled compounds, i.e., where one or more atoms have been enriched with atoms having an atomic mass different from the atomic mass predominately found in nature. Examples of isotopes that may be incorporated into the compounds of formula I, for example, include, but are not limited to, $^2H$, $^3H$, $^{13}C$, $^{14}C$, $^{15}N$, $^{18}O$, $^{17}O$, $^{35}S$, $^{36}Cl$, and $^{18}F$.

The compounds of formula I have been found to possess $AT_1$ receptor antagonizing activity and NEP enzyme inhibition activity. Among other properties, such compounds are expected to be useful as therapeutic agents for treating diseases such as hypertension. By combining dual activity into a single compound, double therapy can be achieved, i.e., $AT_1$ receptor antagonist activity and NEP enzyme inhibition activity can be obtained using a single active component. Since pharmaceutical compositions containing one active component are typically easier to formulate than compositions containing two active components, such single-component compositions provide a significant advantage over compositions containing two active components. In addition, certain compounds of the invention have also been found to be selective for inhibition of the $AT_1$ receptor over the angiotensin II type 2 ($AT_2$) receptor, a property that may have therapeutic advantages.

The nomenclature used herein to name the compounds of the invention is illustrated in the Examples herein. This nomenclature has been derived using the commercially available AutoNom software (MDL, San Leandro, Calif.).

REPRESENTATIVE EMBODIMENTS

The following substituents and values are intended to provide representative examples of various aspects and embodiments of the invention. These representative values are intended to further define and illustrate such aspects and embodiments and are not intended to exclude other embodiments or to limit the scope of the invention. In this regard, the representation that a particular value or substituent is preferred is not intended in any way to exclude other values or substituents from the invention unless specifically indicated.

In one aspect, the invention relates to compounds of formula I:

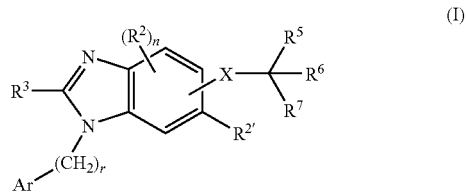

The values for r are 0, 1 or 2. In one embodiment, r is 1. Each —$CH_2$— group in the —$(CH_2)_r$— group may be substituted with 1 or 2 substituents independently selected from —$C_{1-4}$alkyl (for example, —$CH_3$) and fluoro. In one particular embodiment, the —$(CH_2)_r$— group is unsubstituted; in another embodiment, one or two —$CH_2$— groups in —$(CH_2)_r$— are substituted with an —$C_{1-4}$alkyl group.

Ar represents an aryl grup selected from:

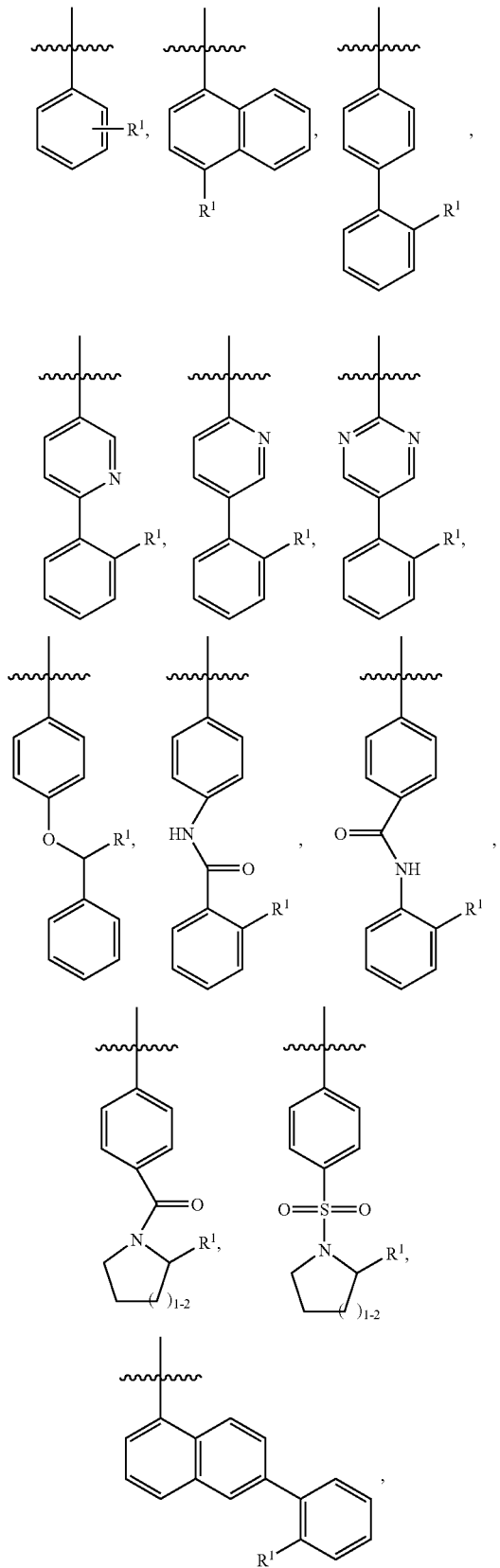

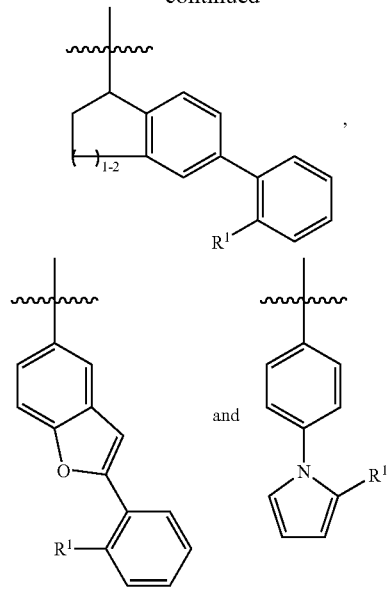

Each ring in the Ar moiety may be substituted with 1 to 3 substituents independently selected from —OH, —$C_{1-6}$alkyl, —$C_{2-4}$alkenyl, —$C_{2-4}$alkynyl, —CN, halo, —O—$C_{1-6}$alkyl, —S—$C_{1-6}$alkyl, —S(O)—$C_{1-6}$alkyl, —S(O)$_2$—$C_{1-4}$alkyl, -phenyl, —NO$_2$, —NH$_2$, —NH—$C_{1-6}$alkyl and —N($C_{1-6}$alkyl)$_2$. Furthermore, each of the aforementioned alkyl, alkenyl and alkynyl groups are optionally substituted with 1 to 5 fluoro atoms.

In one particular embodiment, each ring in the Ar moiety may be substituted with 1 to 2 substituents independently selected from —OH, —$C_{1-4}$alkyl (for example, —$CH_3$), halo (for example bromo, fluoro, chloro, and di-fluoro), —O—$C_{1-4}$ alkyl (for example, —$OCH_3$), and -phenyl. Exemplary substituted Ar moieties include:

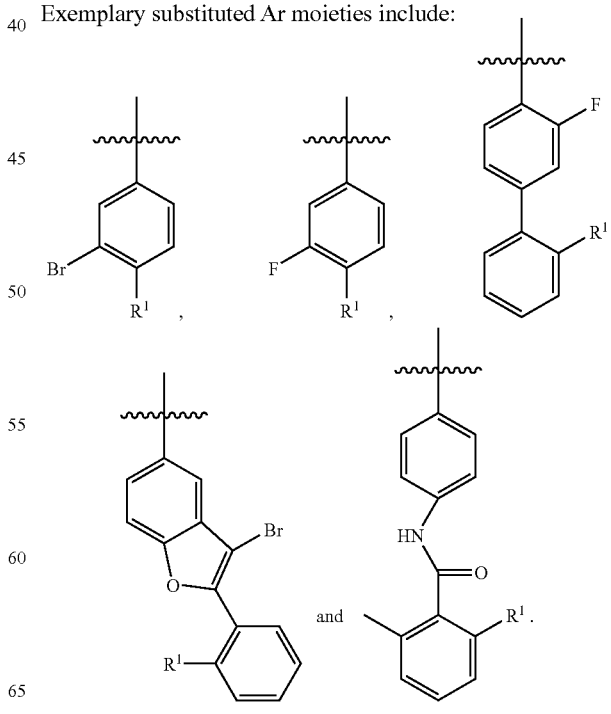

Of particular interest is the embodiment where Ar is substituted with 1 or 2 halo atoms.

It is understood that the Ar structure depicted as:

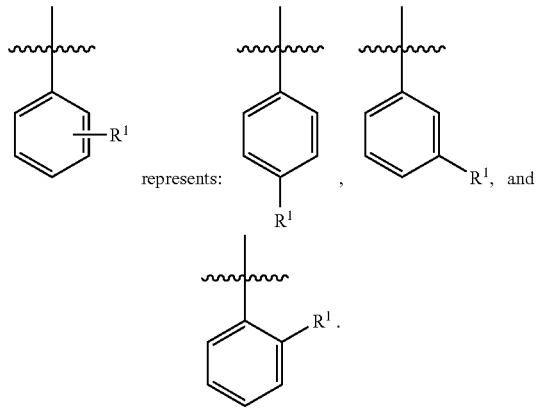

represents:

In one particular embodiment, Ar is an aryl group selected from:

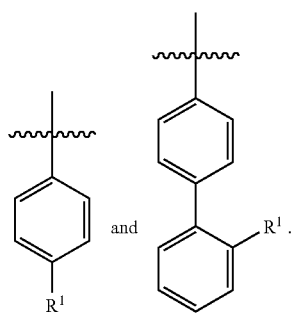

$R^1$ is selected from —COOR$^{1a}$, —NHSO$_2$R$^{1b}$, —SO$_2$NHR$^{1d}$, —SO$_2$OH, —C(O)NH—SO$_2$R$^{1c}$, —P(O)(OH)$_2$, —CN, —OCH(R$^{1e}$)—COOH, tetrazol-5-yl, and

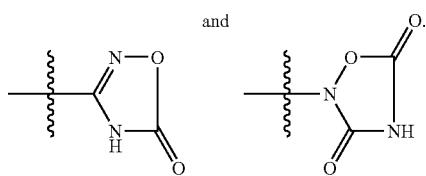

The R$^{1a}$ moiety is H, —C$_{1-6}$alkyl, —C$_{1-3}$alkylenearyl, —C$_{1-3}$alkyleneheteroaryl, —C$_{3-7}$cycloalkyl, —CH(C$_{1-4}$alkyl)OC(O)R$^{1aa}$, —C$_{0-6}$alkylenemorpholine,

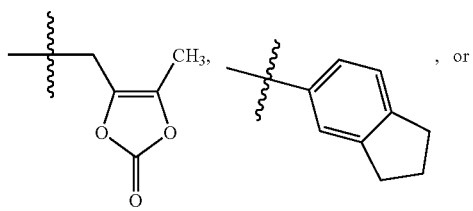

, or

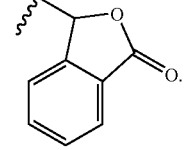

R$^{1aa}$ is —O—C$_{1-6}$alkyl, —O—C$_{3-7}$cycloalkyl, —NR$^{1ab}$R$^{1ac}$, or —CH(NH$_2$)CH$_2$COOCH$_3$. R$^{1ab}$ and R$^{1ac}$ are independently selected from H, —C$_{1-6}$alkyl, and benzyl, or are taken together as —(CH$_2$)$_{3-6}$—.

The R$^{1b}$ moiety is R$^{1c}$ or —NHC(O)R$^{1c}$. The R$^{1c}$ group is —C$_{1-6}$alkyl, —C$_{0-6}$alkylene-O—R$^{1ca}$, —C$_{1-5}$alkylene-NR$^{1cb}$R$^{1cc}$, —C$_{0-4}$alkylenearyl, or —C$_{0-4}$alkyleneheteroaryl. The R$^{1ca}$ moiety is H, —C$_{1-6}$alkyl, or —C$_{1-6}$alkylene-O—C$_{1-6}$alkyl. The R$^{1cb}$ and R$^{1cc}$ groups are independently selected from H and —C$_{1-6}$alkyl, or are taken together as —(CH$_2$)$_2$—O—(CH$_2$)$_2$— or —(CH$_2$)$_2$—N[C(O)CH$_3$]—(CH$_2$)$_2$—. The R$^{1d}$ moiety is H, R$^{1c}$, —C(O)R$^{1c}$, or —C(O)NHR$^{1c}$. The R$^{1e}$ group is C$_{1-4}$alkyl or aryl.

Each alkyl and each aryl in R$^1$ is optionally substituted with 1 to 7 fluoro atoms. In addition, the term "alkyl" is intended to include divalent alkylene groups such as those present in —C$_{1-3}$alkylenearyl and —C$_{1-3}$alkyleneheteroaryl, for example. Further, each aryl and heteroaryl group that might be present in R$^1$, may be substituted with 1 to 3-OH, —C$_{1-6}$alkyl, —C$_{2-4}$alkenyl, —C$_{2-4}$alkynyl, —CN, halo, —O—C$_{1-6}$alkyl, —S—C$_{1-6}$alkyl, —S(O)—C$_{1-6}$alkyl, —S(O)$_2$—C$_{1-4}$alkyl, -phenyl, —NO$_2$, —NH$_2$, —NH—C$_{1-6}$alkyl, or —N(C$_{1-6}$alkyl)$_2$ groups. Further, each of the aforementioned alkyl, alkenyl and alkynyl groups may be substituted with 1 to 5 fluoro atoms. It is understood that when referring to "each alkyl," "each aryl" and "each heteroaryl" group in R$^1$, the terms also include any alkyl, aryl and heteroaryl groups that might be present in the R$^{1a}$ through R$^{1e}$ moieties.

In one embodiment, R$^1$ is —COOR$^{1a}$ and R$^{1a}$ is H. In another embodiment, R$^1$ is —COOR$^{1a}$ and R$^{1a}$ is —C$_{1-6}$alkyl, examples of which include —CH$_3$, —CH$_2$CH$_3$, —(CH$_2$)$_2$CH$_3$, —(CH$_2$)$_2$—CF$_3$, —CH$_2$CH(CH$_3$)$_2$, —CH(CH$_3$)$_2$, —CH(CH$_3$)—CF$_3$, —CH(CH$_2$F)$_2$, —C(CH$_3$)$_3$, —(CH$_2$)$_3$CH$_3$, and —(CH$_2$)$_2$—CF$_2$CF$_3$. Thus, examples of R$^1$ include —C(O)OCH$_3$, —COOCH$_2$CH$_3$, —C(O)O(CH$_2$)$_2$CH$_3$, —C(O)OCH$_2$CH(CH$_3$)$_2$, —C(O)O(CH$_2$)$_3$CH$_3$, and so forth.

In one embodiment, R$^1$ is —COOR$^{1a}$ and R$^{1a}$ is —C$_{1-3}$alkylenearyl, for example, a benzyl group, which may be substituted such as chlorobenzyl, fluorobenzyl, di fluorobenzyl, -benzyl-CH$_3$, -benzyl-CF$_3$ and -benzyl-OCF$_3$. Thus, examples of R$^1$ include: —C(O)OCH$_2$-benzyl,

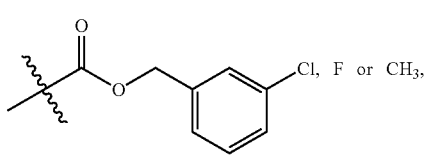

Cl, F or CH$_3$,

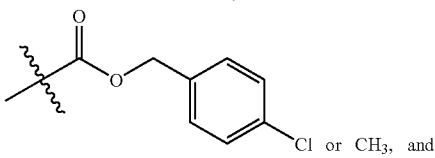

Cl or CH$_3$, and

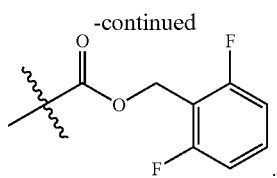

In one embodiment, $R^1$ is —COOR$^{1a}$ and $R^{1a}$ is —C$_{1-3}$ alkyleneheteroaryl, examples of which include —CH$_2$-pyridinyl. In one embodiment, $R^1$ is —COOR$^{1a}$ and $R^{1a}$ is —C$_{3-7}$cycloalkyl, examples of which include cyclopentyl.

In yet another embodiment $R^1$ is —COOR$^{1a}$ and $R^{1a}$ is —CH(C$_{1-4}$alkyl)OC(O)R$^{1aa}$, where R$^{1aa}$ is —O—C$_{1-6}$alkyl, —O—C$_{3-7}$cycloalkyl, —NR$^{1ab}$R$^{1ac}$, or —CH(NH$_2$)CH$_2$COOCH$_3$. R$^{1ab}$ and R$^{1ac}$ are independently selected from H, —C$_{1-6}$alkyl, and benzyl, or are taken together as —(CH$_2$)$_{3-6}$—. Examples of —O—C$_{1-6}$alkyl groups include —O—CH$_2$CH$_3$ and —O—CH(CH$_3$)$_2$. Exemplary —O—C$_{3-7}$cycloalkyl groups include —O—cyclohexyl. Thus, examples of R$^1$ include —C(O)OCH(CH$_3$)OC(O)—O—CH$_2$CH$_3$, —C(O)OCH(CH$_3$)OC(O)—O—CH(CH$_3$)$_2$, and —C(O)OCH(CH$_3$)OC(O)—O-cyclohexyl.

In one embodiment, $R^1$ is —COOR$^{1a}$ and $R^{1a}$ is —C$_{0-6}$ alkylenemorpholine, examples of which include —(CH$_2$)$_2$-morpholine and —(CH$_2$)$_3$-morpholine. In another embodiment, $R^{1a}$ is

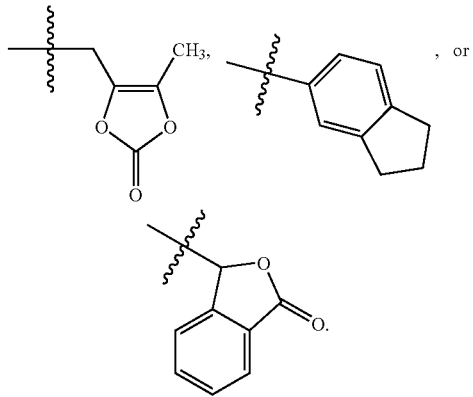

In one embodiment, R$^1$ is —NHSO$_2$R$^{1b}$ and R$^{1b}$ is R$^{1c}$. The R$^{1c}$ group is —C$_{1-6}$alkyl, —C$_{0-6}$alkylene-O—R$^{1ca}$, —C$_{1-5}$ alkylene-NR$^{1cb}$R$^{1cc}$, —C$_{0-4}$alkylenearyl or —C$_{0-4}$alkyleneheteroaryl. The R$^{1ca}$ moiety is H, —C$_{1-6}$alkyl, or —C$_{1-6}$alkylene-O—C$_{1-6}$alkyl. The R$^{1cb}$ and R$^{1cc}$ groups are independently selected from H and —C$_{1-6}$alkyl, or are taken together as —(CH$_2$)$_2$—O—(CH$_2$)$_2$— or —(CH$_2$)$_2$—N[C(O)CH$_3$]—(CH$_2$)$_2$—. In one embodiment, R$^{1c}$ is —C$_{1-6}$alkyl, such that exemplary R$^1$ groups include —NHSO$_2$—CH$_3$ and the fluoro-substituted group, —NHSO$_2$—CF$_3$. In another embodiment, R$^{1c}$ is C$_{0-4}$alkylenearyl, such that exemplary R$^1$ groups include —NHSO$_2$-phenyl. In another embodiment, R$^{1c}$ is —C$_{0-4}$alkyleneheteroaryl, such that exemplary R$^1$ groups include —NHSO$_2$-4,5-dimethylisoxazol-3-yl.

In another embodiment, R$^1$ is —NHSO$_2$R$^{1b}$ and R$^{1b}$ is —NHC(O)R$^{1c}$, where R$^{1c}$ is defined above. In a particular embodiment, R$^1$ is —NHSO$_2$R$^{1b}$, R$^{1b}$ is —NHC(O)R$^{1c}$, and R$^{1c}$ is —C$_{1-6}$alkyl or —C$_{0-4}$alkylenearyl.

In another embodiment, R$^1$ is —SO$_2$NHR$^{1d}$ and R$^{1d}$ is H. In another embodiment, R$^1$ is —SO$_2$NHR$^{1d}$ and R$^{1d}$ is R$^{1c}$, where R$^{1c}$ is defined above. In a particular embodiment, R$^{1c}$ is —C$_{1-6}$alkyl or —C$_{0-4}$alkylenearyl. When R$^{1c}$ is —C$_{1-6}$ alkyl, exemplary R$^1$ groups include the fluoro-substituted groups —SO$_2$NH—CF$_3$, —SO$_2$NH—CHF$_2$, —SO$_2$NH—CF$_2$CH$_2$F and —SO$_2$NH—CF$_2$CF$_2$CF$_3$.

In another embodiment, R$^1$ is —SO$_2$NHR$^{1d}$ and R$^{1d}$ is —C(O)R$^{1c}$, where R$^{1c}$ is defined above. In a particular embodiment, R$^{1c}$ is —C$_{1-6}$alkyl or —C$_{0-4}$alkylenearyl. When R$^{1c}$ is —C$_{1-6}$alkyl, exemplary R$^1$ groups include —SO$_2$NHC(O)CH$_3$ and —SO$_2$NHC(O)(CH$_2$)$_2$CH$_3$. When R$^{1c}$ is —C$_{0-6}$ alkylene-O—R$^{1ca}$ and R$^{1ca}$ is H, exemplary R$^1$ groups include —SO$_2$NHC(O)CH$_2$OH, —SO$_2$NHC(O)CH(CH$_3$)OH, and —SO$_2$NHC(O)C(CH$_3$)$_2$OH. When R$^{1c}$ is —C$_{0-6}$ alkylene-O—R$^{1ca}$ and R$^{1ca}$ is —C$_{1-6}$alkyl, exemplary R$^1$ groups include —SO$_2$NHC(O)CH$_2$—O—CH$_3$, —SO$_2$NHC(O)—O—CH$_3$, and —SO$_2$NHC(O)—O—CH$_2$CH$_3$. When R$^{1c}$ is —C$_{0-6}$alkylene-O—R$^{1ca}$ and R$^{1ca}$ is —C$_{1-6}$alkylene-O—C$_{1-6}$alkyl, exemplary R$^1$ groups include —SO$_2$NHC(O)CH$_2$—O—(CH$_2$)$_2$—O—CH$_3$. When R$^{1c}$ is —C$_{1-5}$alkylene-NR$^{1cb}$R$^{1cc}$, exemplary R$^1$ groups include —SO$_2$NHC(O)CH$_2$N(CH$_3$)$_2$, —SO$_2$NHC(O)CH$_2$NH$_2$, and —SO$_2$NHC(O)—CH(CH$_3$)NH$_2$. Another example when R$^{1c}$ is —C$_{1-5}$ alkylene-NR$^{1cb}$R$^{1cc}$ is where the R$^{1cb}$ and R$^{1cc}$ are taken together as —(CH$_2$)$_2$—O—(CH$_2$)$_2$— or —(CH$_2$)$_2$—N[C(O)CH$_3$]—(CH$_2$)$_2$—. Such exemplary R$^1$ groups include:

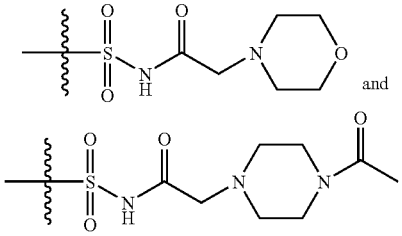

In another embodiment, R$^1$ is —SO$_2$NHR$^{1d}$ and R$^{1d}$ is —C(O)NHR$^{1c}$, where R$^{1c}$ is defined above. In a particular embodiment, R$^{1c}$ is —C$_{1-6}$alkyl or —C$_{0-4}$alkylenearyl. When R$^{1c}$ is —C$_{1-6}$alkyl, exemplary R$^1$ groups include —SO$_2$NHC(O)NH—CH$_2$CH$_3$ and —SO$_2$NHC(O)NH—(CH$_2$)$_2$CH$_3$. When R$^{1c}$ is —C$_{0-4}$alkylenearyl, exemplary R$^1$ groups include —SO$_2$NHC(O)NH-phenyl.

In yet another embodiment, R$^1$ is —SO$_2$OH. In one embodiment, —P(O)(OH)$_2$. In still another embodiment, R$^1$ is —CN.

In another embodiment, R$^1$ is —C(O)NH—SO$_2$R$^{1c}$, where R$^{1c}$ is defined above. In a particular embodiment, R$^{1c}$ is —C$_{1-6}$ alkyl or —C$_{0-4}$alkylenearyl. When R$^{1c}$ is —C$_{1-6}$alkyl, exemplary R$^1$ groups include —C(O)—NH—SO$_2$—CH$_3$, —C(O)—NH—SO$_2$—CH$_2$CH$_3$ and the fluoro-substituted —C(O)—NH—SO$_2$—CF$_3$ group.

In another embodiment, R$^1$ is —OCH(R$^{1e}$)—COOH, where R$^{1e}$ is —C$_{1-4}$alkyl or aryl. Examples of such R$^1$ groups include, —OCH(CH$_3$)—COOH and —OCH(phenyl)-COOH.

In one particular embodiment, R$^1$ is selected from —COOR$^{1a}$ and tetrazol-5-yl. In another embodiment, R$^1$ is —COOR$^{1a}$ and R$^{1a}$ is H or —C$_{1-6}$alkyl.

The values for n are 0, 1, 2 or 3. In one embodiment, n is 0. In another embodiment, n is 1.

Each R$^2$ is independently selected from halo, —NO$_2$, —C$_{1-6}$alkyl, —C$_{2-6}$alkenyl, —C$_{3-7}$cycloalkyl, —CN, —C(O)R$^{2a}$, —C$_{0-5}$alkylene-OR$^{2b}$, —C$_{0-5}$alkylene-NR$^{2c}$R$^{2d}$, —C$_{0-3}$alkylenearyl, and —C$_{0-3}$alkyleneheteroaryl. The R$^{2a}$ moiety is H, —C$_{1-6}$alkyl, —C$_{3-7}$cycloalkyl, —OR$^{2b}$, or —$NR^{2c}R^{2d}$. $R^{2b}$ is selected from H, —$C_{1-6}$alkyl, —$C_{3-7}$cycloalkyl, and —$C_{0-1}$alkylenearyl; and $R^{2c}$ and $R^{2d}$ are independently selected from H, —$C_{1-4}$alkyl, and —$C_{0-1}$alkylenearyl.

In one particular embodiment, $R^2$ is halo, for example, chloro. In yet another embodiment, $R^2$ is —$C_{1-6}$alkyl such as —$CH_3$, and fluoro-substituted alkyl groups such as —$CH_2F$ and —$CF_3$. In another embodiment $R^2$ is —$C_{0-5}$alkylene-$OR^{2b}$ and $R^{2b}$ is H; one such $R^2$ group is —$CH_2OH$.

The $R^{2'}$ moiety can be H or a moiety as defined above for $R^2$, i.e., is selected from, halo, —$NO_2$, —$C_{1-6}$alkyl, —$C_{2-6}$alkenyl, —$C_{3-7}$cycloalkyl, —CN, —$C(O)R^{2a}$, —$C_{0-5}$alkylene-$OR^{2b}$, —$C_{0-5}$alkylene-$NR^{2c}R^{2d}$, —$C_{0-3}$alkylenearyl, and —$C_{0-3}$alkyleneheteroaryl. In one particular embodiment, $R^{2'}$ is H. In another embodiment $R^{2'}$ is —$C(O)R^{2a}$ and $R^{2a}$ is —$C_{1-6}$alkyl such as —$CH_3$.

Each alkyl and each aryl in $R^2$ and $R^{2'}$ is optionally substituted with 1 to 7 fluoro atoms. It is understood that when referring to the "alkyl" in $R^2$ or $R^{2'}$, the term includes any alkyl groups that might be present in the $R^{2a}$, $R^{2b}$, $R^{2c}$ and $R^{2d}$ moieties. In addition, each aryl and heteroaryl in $R^2$ and $R^{2'}$, for example in —$C_{0-3}$alkylenearyl and —$C_{0-3}$alkyleneheteroaryl, may be substituted with 1 to 3-OH, —$C_{1-6}$alkyl, —$C_{2-4}$alkenyl, —$C_{2-4}$alkynyl, —CN, halo, —O—$C_{1-6}$alkyl, —S—$C_{1-6}$alkyl, —S(O)—$C_{1-6}$alkyl, —$S(O)_2$—$C_{1-4}$alkyl, -phenyl, —$NO_2$, —$NH_2$, —NH—$C_{1-6}$alkyl, or —$N(C_{1-6}$alkyl$)_2$ groups. Further, each of the aforementioned alkyl, alkenyl and alkynyl groups may be substituted with 1 to 5 fluoro atoms. It is understood that when referring to the "aryl" or the "heteroaryl" in $R^2$ or $R^{2'}$, the terms includes any aryl or heteroaryl groups that might be present in the $R^{2a}$, $R^{2b}$, $R^{2c}$ and $R^{2d}$ moieties.

$R^3$ is selected from —$C_{1-10}$alkyl, —$C_{2-10}$alkenyl, —$C_{3-10}$alkynyl, —$C_{0-3}$alkylene-$C_{3-7}$cycloalkyl, —$C_{2-3}$alkenylene-$C_{3-7}$cycloalkyl, —$C_{2-3}$alkynylene-$C_{3-7}$cycloalkyl, —$C_{0-5}$alkylene-$NR^{3a}C_{0-5}$alkylene-$R^{3b}$, —$C_{0-5}$alkylene-O—$C_{0-5}$alkylene-$R^{3b}$, —$C_{1-5}$alkylene-S—$C_{1-5}$alkylene-$R^{3b}$, and —$C_{0-3}$alkylenearyl (for example, —$C_{0-1}$alkylenearyl such as phenyl and benzyl). The $R^{3a}$ moiety is H, —$C_{1-6}$alkyl, —$C_{3-7}$cycloalkyl, or —$C_{0-3}$alkylenearyl (for example, —$C_{0-1}$alkylenearyl such as phenyl and benzyl). $R^{3b}$ is H, —$C_{1-6}$alkyl, —$C_{3-7}$cycloalkyl, —$C_{2-4}$alkenyl, —$C_{2-4}$alkynyl, or aryl (such as phenyl).

In addition, each alkyl and each aryl in $R^3$ is optionally substituted with 1 to 7 fluoro atoms, where the term "alkyl" is intended to include divalent alkylene groups such as those present in —$C_{0-3}$alkylene-$C_{3-7}$cycloalkyl and —$C_{0-3}$alkylenearyl, for example. Each aryl in $R^3$, for example in —$C_{0-3}$alkylenearyl or aryl, may be substituted with 1 to 3-OH, —$C_{1-6}$alkyl, —$C_{2-4}$alkenyl, —$C_{2-4}$alkynyl, —CN, halo, —O—$C_{1-6}$alkyl, —S—$C_{1-6}$alkyl —S(O)—$C_{1-6}$alkyl, —$S(O)_2$—$C_{1-4}$alkyl, -phenyl, —$NO_2$, —$NH_2$, —NH—$C_{1-6}$alkyl, or —$N(C_{1-6}$alkyl$)_2$ groups. Further, each of the aforementioned alkyl, alkenyl and alkynyl groups may be substituted with 1 to 5 fluoro atoms. It is understood that when referring to "each alkyl" and "each aryl" group in $R^3$, the terms also include any alkyl and aryl groups that might be present in the $R^{3a}$ and $R^{3b}$ moieties.

In one embodiment, $R^3$ is —$C_{1-10}$alkyl optionally substituted with 1 to 7 fluoro atoms. In another embodiment, $R^3$ is —$C_{2-7}$alkyl; and in yet another embodiment, $R^3$ is —$C_{3-5}$alkyl. Examples of such $R^3$ groups include, —$CH_3$, —$CF_3$, —$CH_2CH_3$, —$(CH_2)_2CH_3$, —$(CH_2)_3CH_3$, —$CH_2$—CH$(CH_3)_2$, —$CH_2$—CH$(CH_3)CH_2CH_3$, —$(CH_2)_2$—CH$(CH_3)_2$, —CH$(CH_2CH_3)_2$, and —$(CH_2)_4CH_3$.

In another embodiment, $R^3$ is —$C_{2-10}$alkenyl such as —$CH_2CH$=$CHCH_3$. In yet another embodiment, $R^3$ is —$C_{3-10}$alkynyl such as —$CH_2C$≡$CCH_3$.

In another embodiment, $R^3$ is —$C_{0-3}$alkylene-$C_{3-7}$cycloalkyl such as -cyclopropyl, —$CH_2$-cyclopropyl, cyclopentyl, —$CH_2$-cyclopentyl, —$(CH_2)_2$-cyclopentyl, and —$CH_2$-cyclohexyl. In a particular embodiment, $R^3$ is —$C_{0-1}$alkylene-$C_{3-5}$cycloalkyl. In one embodiment, $R^3$ is —$C_{2-3}$alkenylene-$C_{3-7}$cycloalkyl, such as —$CH_2CH$=CH-cyclopentyl; and in another embodiment, $R^3$ is —$C_{2-3}$alkynylene-$C_{3-7}$cycloalkyl, such as —$CH_2C$≡C-cyclopentyl.

In yet another embodiment, $R^3$ is —$C_{0-5}$alkylene-$NR^{3a}$—$C_{0-5}$alkylene-$R^{3b}$. In one particular embodiment, $R^{3a}$ is H and $R^{3b}$ is —$C_{1-6}$alkyl. Examples of such $R^3$ groups include —$NHCH_2CH_3$, —$NHCH(CH_3)_2$, —$NH(CH_2)_2CH_3$, —$NH(CH_2)_3CH_3$, —$NHCH(CH_3)CH_2CH_3$, —$NH(CH_2)_4CH_3$, and —$NH(CH_2)_5CH_3$.

In another embodiment, $R^3$ is —$C_{0-5}$alkylene-O—$C_{1-5}$alkylene. In one particular embodiment $R^{3b}$ is selected from H, —$C_{1-6}$alkyl, and aryl. Examples of such $R^3$ groups include —$OCH_3$, —O—$CH_2CH_3$, —$OCH(CH_3)_2$, —$O(CH_2)_2CH_3$, —$O(CH_2)_3CH_3$, —$OCH_2CH(CH_3)_2$, —O-phenyl, and —O-benzyl. In another embodiment, $R^3$ is —$C_{0-5}$alkylene-O—$C_{0-5}$alkylene-$R^{3b}$, where $R^{3b}$ is —$C_{1-6}$alkyl, and in another embodiment, $R^3$ is —O—$C_{1-5}$alkyl.

In another embodiment, $R^3$ is —$C_{1-5}$alkylene-S—$C_{1-5}$alkylene-$R^{3b}$, and in one particular embodiment $R^{3b}$ is H, such as when $R^3$ is —$CH_2$—S—$CH_2CH_3$. In another embodiment, $R^3$ is —$C_{0-3}$alkylenearyl, such as phenyl, benzyl, and —$(CH_2)_2$-phenyl.

X is —$C_{1-12}$alkylene-, where at least one —$CH_2$— moiety in the alkylene is replaced with a —$NR^{4a}$—$C(O)$— or —$C(O)$—$NR^{4a}$— moiety. Thus X can be —$C_1$alkylene-, —$C_1$alkylene-, —$C_2$alkylene-, —$C_3$alkylene-, —$C_4$alkylene-, —$C_5$alkylene-, —$C_6$alkylene-, —$C_7$alkylene-, —$C_8$alkylene, —$C_9$alkylene-, —$C_{10}$alkylene-, —$C_{11}$alkylene-, or —$C_{12}$alkylene-, with at least one —$CH_2$— moiety being replaced. $R^{4a}$ is selected from H, —OH, and —$C_{1-4}$alkyl. In one embodiment, $R^{4a}$ is H. Each carbon atom in the —$C_{1-12}$alkylene-moiety may be substituted with one or more $R^{4b}$ groups. $R^{4b}$ is selected from —$C_{0-5}$alkylene-$COOR^{4c}$, —$C_{1-6}$alkyl, —$C_{0-1}$alkylene-$CONH_2$, —$C_{1-2}$alkylene-OH, —$C_{0-3}$alkylene-$C_{3-7}$cycloalkyl, 1H-indol-3-yl, benzyl, and hydroxybenzyl, where $R^{4c}$ is H or —$C_{1-4}$alkyl.

In one embodiment, the carbon atoms in —$C_{1-2}$alkylene- are unsubstituted, i.e., there are no $R^{4b}$ groups. In another embodiment, one carbon atom is substituted with one $R^{4b}$ group; and in another embodiment, 1 or 2 carbon atoms are substituted with one or two $R^{4b}$ groups. In one embodiment, $R^{4b}$ is —$C_{0-5}$alkylene-$COOR^{4c}$, where $R^{4c}$ is H or —$C_{1-4}$alkyl. Examples of such $R^{4b}$ groups include —COOH, —$CH_2COOH$, —$(CH_2)_2COOH$, and $CH_2COOCH_3$. In another embodiment, $R^{4b}$ is —$C_{1-6}$alkyl, for example —$CH_3$ or —$CH(CH_3)_2$. In one embodiment, $R^{4b}$ is —$C_{0-1}$alkylene-$CONH_2$, for example —$CH_2$—$CONH_2$ or —$(CH_2)_2$—$CONH_2$. In yet another embodiment, $R^{4b}$ is —$C_{1-2}$alkylene-OH, for example $CH_2$—OH. In one embodiment, $R^{4b}$ is 1H-indol-3-yl, benzyl, or hydroxybenzyl.

In addition, one —$CH_2$— moiety in X may be replaced with a group selected from —$C_{4-8}$cycloalkylene-, —$CR^{4d}$=CH—, and —CH=$CR^{4d}$—. $R^{4d}$ is selected from —$CH_2$-thiophene and phenyl. In one embodiment, none of the —$CH_2$— moieties are so replaced. In another embodiment, one —$CH_2$— moiety in X is replaced with —$C_{4-8}$cycloalkylene-, for example, cyclohexylene. In another embodiment, one —CH$_2$— moiety is replaced with —CH=CR$^{4d}$—, where R$^{4d}$ is —CH$_2$-thiophene such as —CH$_2$-thiophen-2-yl.

Each alkyl and each aryl in R$^{4a}$, R$^{4b}$, R$^{4c}$, and R$^{4d}$, may be substituted with 1 to 7 fluoro atoms, and the term "alkyl" is intended to include divalent alkylene groups such as that present in —C$_{0-5}$alkylene-COOR$^{4c}$, for example. It is noted that the R$^{4b}$ group, —C$_{0-3}$alkylene-C$_{3-7}$cycloalkyl moiety is intended to include a —C$_{3-7}$cycloalkyl linked to the X—C$_{1-12}$ alkylene-chain by a bond as well as a —C$_{3-7}$cycloalkyl that is directly attached to the chain, as illustrated below:

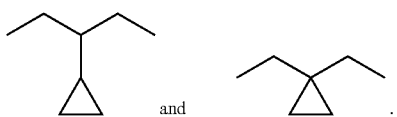

and

In one embodiment, one to four —CH$_2$— moieties are replaced with —NR$^{4a}$—C(O)— or —C(O)—NR$^{4a}$— moieties; and in another embodiment one —CH$_2$— moiety is replaced, examples of which include: —C(O)NH—, —NHC(O)—, and —CH$_2$—NHC(O)—. In one embodiment, X is —C$_{1-6}$alkylene- and one to four —CH$_2$— moieties are replaced with a —NR$^{4a}$—C(O)— or —C(O)—NR$^{4a}$— moiety; and in another embodiment X is —C$_{1-4}$alkylene- and one or two —CH$_2$-moieties are replaced. In one embodiment X is —C$_{1-2}$alkylene- and one —CH$_2$— moiety is replaced. In another embodiment X is —C$_1$alkylene- and one —CH$_2$— moiety is replaced, i.e., X is —NR$^{4a}$—C(O)— or —C(O)—NR$^{4a}$—, for example, —C(O)—NH—. When more than one —CH$_2$— moiety in —C$_{1-12}$alkylene- is replaced with a —NR$^{4a}$—C(O)— or —C(O)—NR$^{4a}$— moiety, the replaced moieties may be contiguous or non-contiguous. In one particular embodiment, the replaced moieties are contiguous. Exemplary X groups include the following, which depict: examples where one or more —CH$_2$— moieties are replaced with —NR$^{4a}$—C(O)— or —C(O)—NR$^{4a}$— moieties; examples where —CH$_2$— moieties are replaced with a group selected from —C$_{4-8}$cycloalkylene-, —CR$^{4d}$=CH—, and —CH=CR$^{4d}$—; and examples where carbon atoms in the —C$_{1-12}$alkylene- group are substituted with one or more R$^{4b}$ groups:

—C$_1$alkylene- with one —CH$_2$— moiety replaced:
—C(O)NH—
—NHC(O)—
—C$_2$alkylene- with one —CH$_2$— moiety replaced:
—CH$_2$—NHC(O)—
—C(O)NH—CH$_2$—
—CH$_2$—C(O)NH—
—CH[CH(CH$_3$)$_2$]—C(O)NH—
—CH(COOH)—NHC(O)—
—CH(CH$_2$COOH)—NHC(O)—
—CH[(CH$_2$)$_2$COOH]—NHC(O)—
—CH(CH$_2$COOCH$_3$)—NHC(O)—
—CH(CH$_3$)—NHC(O)—
—CH(CH(CH$_3$)$_2$)—NHC(O)—
—CH(CH$_2$—CONH$_2$)—NHC(O)—
—CH[(CH$_2$)$_2$—CONH$_2$]—NHC(O)—
—CH(CH$_2$—OH)—NHC(O)—
—CH(benzyl)-NHC(O)—
—CH(4-hydroxybenzyl)-NHC(O)—
—CH(1H-indol-3-yl)-NHC(O)—
—C$_2$alkylene- with two —CH$_2$— moieties replaced:
—C(O)NH—NHC(O)—
—CH=C(—CH$_2$-thiopheny-2-yl)-C(O)NH—
—C$_3$alkylene- with one —CH$_2$— moiety replaced:
—(CH$_2$)$_2$—NHC(O)—
—(CH$_2$)$_2$—C(O)NH—
—CH(CH$_3$)—CH$_2$—NHC(O)—
—CH[CH(CH$_3$)$_2$]—CH$_2$—NHC(O)—
—CH(COOH)—CH$_2$—NHC(O)—
—CH$_2$—CH(COOH)—NHC(O)—
—CH$_2$—C(CH$_3$)$_2$—NHC(O)—
—C$_3$alkylene- with two —CH$_2$— moieties replaced:
—NHC(O)—CH$_2$—NHC(O)—
—C$_4$alkylene- with one —CH$_2$— moiety replaced:
—(CH$_2$)$_3$—NHC(O)—
—C(O)NH—CH$_2$—CH(COOH)—CH$_2$
—C$_4$alkylene- with two —CH$_2$— moieties replaced:
—C(O)NH—CH(benzyl)-CH$_2$—NHC(O)—
—C(O)NH—CH(benzyl)-CH$_2$—C(O)NH—
—CH$_2$—NHC(O)—CH$_2$—NHC(O)—
—CH(benzyl)-NHC(O)—CH$_2$—NHC(O)—
—CH(1H-indol-3-yl)-NHC(O)—CH$_2$—NHC(O)—
—C$_4$alkylene- with three —CH$_2$— moieties replaced:
—CH$_2$—NHC(O)-cyclohexylene-NHC(O)—
—CH$_2$—N(OH)C(O)-cyclohexylene-NHC(O)—
—C$_5$alkylene- with two —CH$_2$— moieties replaced:
—CH$_2$—NHC(O)—CH$_2$—CH(COOH)—NHC(O)—
—CH$_2$—NHC(O)—(CH$_2$)$_2$—NHC(O)—
—C(O)NH—(CH$_2$)$_2$—C(O)N(OH)—CH$_2$
—C(O)NH—(CH$_2$)$_2$—CH(COOH)—NHC(O)—
—CH(COOH)—CH$_2$—NHC(O)—CH$_2$—NHC(O)—
—(CH$_2$)$_2$—NHC(O)-cyclohexylene-NHC(O)—
—CH$_2$—CH(COOH)—NHC(O)—CH$_2$—NHC(O)—
—C$_6$alkylene- with two —CH$_2$— moieties replaced:
—C(O)NH—(CH$_2$)$_4$—NHC(O)—
—CH$_2$—NHC(O)—(CH$_2$)$_2$—CH(COOH)—NHC(O)—
—C(O)NH—(CH$_2$)$_3$—CH(COOH)—NHC(O)—
—C$_6$alkylene- with three —CH$_2$— moieties replaced:
—C(O)NH—(CH$_2$)$_2$—NHC(O)—CH$_2$—NHC(O)—
—C$_6$alkylene- with four —CH$_2$— moieties replaced:
—C(O)NH—(CH$_2$)$_2$—NHC(O)-cyclohexylene-NHC(O)—
—C$_7$alkylene- with two —CH$_2$— moieties replaced:
—CH$_2$—NHC(O)—(CH$_2$)$_4$—NHC(O)—
—C(O)NH—(CH$_2$)$_4$—CH(COOH)—NHC(O)—
—C$_7$alkylene- with three —CH$_2$— moieties replaced:
—CH[CH(CH$_3$)$_2$]—C(O)NH—(CH$_2$)$_2$—NHC(O)—CH$_2$—NHC(O)—
—C$_7$alkylene- with four —CH$_2$— moieties replaced:
—CH$_2$—NHC(O)—(CH$_2$)$_2$—NHC(O)-cyclohexylene-NHC(O)—
—CH$_2$—C(O)NH—(CH$_2$)$_2$—NHC(O)-cyclohexylene-NHC(O)—
—C$_8$alkylene- with three —CH$_2$— moieties replaced:
—C(O)NH—(CH$_2$)$_4$—NHC(O)—CH$_2$—NHC(O)—
—C$_8$alkylene- with four —CH$_2$— moieties replaced:
—C(O)NH—(CH$_2$)$_4$—NHC(O)-cyclohexylene-NHC(O)—
—C$_9$alkylene- with two —CH$_2$— moieties replaced:
—CH$_2$—NHC(O)—(CH$_2$)$_6$—NHC(O)—
—C$_9$alkylene- with four —CH$_2$— moieties replaced:
—CH$_2$—NHC(O)—(CH$_2$)$_4$—NHC(O)-cyclohexylene-NHC(O)—
—C$_{10}$alkylene- with four —CH$_2$— moieties replaced:
—C(O)NH—(CH$_2$)$_6$—NHC(O)-cyclohexylene-NHC(O)—
—C$_{11}$alkylene- with three —CH$_2$— moieties replaced:
—CH(CH(CH$_3$)$_2$)—C(O)NH—(CH$_2$)$_6$—NHC(O)—CH$_2$—NHC(O)—

—C₁₁alkylene- with four —CH₂— moieties replaced: —CH₂—NHC(O)—(CH₂)₆—NHC(O)-cyclohexylene-NHC(O)—

In one particular embodiment, X is —C$_{1-6}$alkylene- with one or two —CH₂— moieties being replaced with —NHC(O)— or —C(O)NH—, and in another embodiment X is —C$_{1-4}$alkylene- with one or two —CH₂— moieties being replaced. In another embodiment, X is selected from —C(O)NH—, —NHC(O)—, and —CH₂—NHC(O)—. In yet another embodiment, X is —C(O)NH—.

$R^5$ is selected from —C$_{0-3}$alkylene-SR$^{5a}$, —C$_{0-3}$alkylene-C(O)NR$^{5b}$R$^{5c}$, —C$_{0-3}$alkylene-NR$^{5b}$—C(O)R$^{5d}$, —NH—C$_{0-1}$alkylene-P(O)(OR$^{5e}$)₂, —C$_{0-3}$alkylene-P(O)OR$^{5e}$R$^{5f}$, —C$_{0-2}$alkylene-CHR$^{5g}$COOH, —C$_{0-3}$alkylene-C(O)NR$^{5h}$—CHR$^{5i}$—COOH, and —C$_{0-3}$alkylene-S—SR$^{5j}$. Each alkyl and each aryl in $R^5$ is optionally substituted with 1 to 7 fluoro atoms, where the term "alkyl" is intended to include divalent alkylene groups such as those present in —C$_{0-3}$alkylene-SR$^{5a}$ and —C$_{0-3}$alkylene-P(O)OR$^{5e}$R$^{5f}$, for example. Each aryl and heteroaryl in $R^5$ may be substituted with 1 to 3-OH, —C$_{1-6}$alkyl, —C$_{2-4}$alkenyl, —C$_{2-4}$alkynyl, —CN, halo, —O—C$_{1-6}$alkyl, —S—C$_{1-6}$alkyl, —S(O)—C$_{1-6}$alkyl, —S(O)₂—C$_{1-4}$alkyl, -phenyl, —NO₂, —NH₂, —NH—C$_{1-6}$alkyl, or —N(C$_{1-6}$alkyl)₂ groups. Further, each of the aforementioned alkyl, alkenyl and alkynyl groups may be substituted with 1 to 5 fluoro atoms. It is understood that when referring to "each alkyl," "each aryl" and "each heteroaryl" group in $R^5$, the terms also include any alkyl, aryl and heteroaryl groups that might be present in the R$^{5a-5j}$, R$^{5aa}$, R$^{5ab}$, R$^{5ba}$, R$^{5bb}$, R$^{5bc}$, R$^{5ca}$, R$^{5da}$, R$^{5db}$, R$^{5ea}$, R$^{5eb}$, R$^{5ec}$, R$^{5fa}$, R$^{5fb}$ moieties.

In one embodiment, $R^5$ is —C$_{0-3}$alkylene-SR$^{5a}$. R$^{5a}$ is H or —C(O)—R$^{5aa}$. The R$^{5aa}$ group is —C$_{1-6}$alkyl, —C$_{0-6}$alkylene-C$_{3-7}$cycloalkyl, —C$_{0-6}$alkylenearyl, —C$_{0-6}$alkyleneheteroaryl, —C$_{0-6}$alkylenemorpholine, —C$_{0-6}$alkylenepiperazine-CH₃, —CH[N(R$^{5ab}$)₂]-aa where aa is an amino acid side chain, -2-pyrrolidine, —C$_{0-6}$alkylene-OR$^{5ab}$, —OC$_{0-6}$alkylenearyl, —C$_{1-12}$alkylene-OC(O)—C$_{1-6}$alkyl, —C$_{1-2}$alkylene-OC(O)—C$_{0-6}$alkylenearyl, or —C$_{1-2}$alkylene-OC(O)—OC$_{1-6}$alkyl. The R$^{5ab}$ group is independently H or —C$_{1-6}$alkyl. In one specific embodiment, R$^{5a}$ is H, for example $R^5$ can be —SH or —CH₂SH. In another embodiment, R$^{5a}$ is —C(O)—R$^{5aa}$, and R$^{5aa}$—C$_{1-6}$alkyl. Exemplary —C$_{1-6}$alkyl groups include —CH₃, —CH₂CH₃, —CH(CH₃)₂, —C(CH₃)₃, and —CH₂CH(CH₃)₂. Thus, examples of $R^5$ include —SC(O)CH₃, —CH₂SC(O)CH₃, —CH₂SC(O)CH₂CH₃, —CH₂SC(O)CH(CH₃)₂, —CH₂SC(O)C(CH₃)₃, and —CH₂SC(O)CH₂CH(CH₃)₂. In one embodiment, R$^{5a}$ is selected from H and —C(O)—C$_{1-6}$alkyl.

In one embodiment, $R^5$ is —C$_{0-3}$alkylene-SR$^{5a}$, where R$^{5a}$ is —C(O)—R$^{5aa}$, and R$^{5aa}$ is —C$_{0-6}$alkylene-C$_{3-7}$cycloalkyl. Exemplary C$_{3-7}$cycloalkyl groups include cyclopentyl and cyclohexyl. Thus, examples of $R^5$ include —CH₂SC(O)-cyclopentyl, —CH₂SC(O)-cyclohexyl, and —CH₂SC(O)—CH₂-cyclopentyl. In another embodiment, $R^5$ is —C$_{0-3}$alkylene-SR$^{5a}$, where R$^{5a}$ is —C(O)—R$^{5aa}$, and R$^{5aa}$ is —C$_{0-6}$alkylenearyl. In one specific embodiment, the aryl is optionally substituted with 1 to 3 substituents such as —O—C$_{1-6}$alkyl. Exemplary aryl groups include phenyl and -phenyl-OCH₃. Thus, examples of $R^5$ include —CH₂SC(O)-phenyl and —CH₂SC(O)-phenyl-OCH₃. In yet another embodiment, $R^5$ is —C$_{0-3}$alkylene-SR$^{5a}$, where R$^{5a}$ is —C(O)—R$^{5aa}$, and R$^{5aa}$ is —C$_{0-6}$alkyleneheteroaryl. Exemplary heteroaryl groups include furanyl, thienyl and pyridinyl. Thus, examples of $R^5$ include: —CH₂SC(±)-2-pyridine, —CH₂SC(±)-3-pyridine, and —CH₂SC(±)-4-pyridine.

In another embodiment, is —C$_{0-3}$alkylene-SR$^{5a}$, where R$^{5a}$ is —C(O)—R$^{5aa}$, and R$^{5aa}$ is —C$_{0-6}$alkylenemorpholine:

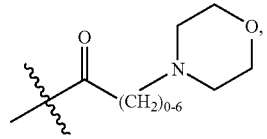

more particularly, —C(O)—C$_{1-3}$alkylenemorpholine. Thus, examples of $R^5$ include —CH₂S—C(O)CH₂-morpholine and —CH₂S—C(O)(CH₂)₂-morpholine. In another embodiment, $R^5$ is —C$_{0-3}$alkylene-SR$^{5a}$, where R$^{5a}$ is —C(O)—R$^{5aa}$, and R$^{5aa}$ is —C$_{0-6}$alkylenepiperazine-CH₃. Thus, examples of $R^5$ include —CH₂S—C(O)(CH₂)₂-piperazine-CH₃.

In one embodiment, $R^5$ is —C$_{0-3}$alkylene-SR$^{5a}$, where R$^{5a}$ is —C(O)—R$^{5aa}$, and R$^{5aa}$ is —CH[N(R$^{5ab}$)₂]-aa where aa is an amino acid side chain. For example, the amino acid side chain could be —CH(CH₃)₂, the valine side chain, —CH₂CH(CH₃)₂ (leucine side chain), —CH(CH₃)CH₂CH₃ (isoleucine side chain), —CH₂COOH (aspartic acid side chain), —(CH₂)₂COOH (glutamic acid side chain), —CH(OH)(CH₃) (threonine side chain), -benzyl (phenylalanine side chain), -4-hydroxybenzyl (tyrosine side chain), and —(CH₂)₂SCH₃ (methionine side chain). Thus, examples of $R^5$ include —CH₂S—C(O)—CH(NH₂)—CH(CH₃)₂, —CH₂SC(O)CH(NH₂)—CH₂CH(CH₃)₂, —CH₂SC(O)CH(NH₂)—CH(CH₃)CH₂CH₃, —CH₂SC(O)CH(NH₂)—CH₂COOH, —CH₂SC(O)CH(NH₂)—(CH₂)₂COOH, —CH₂SC(O)CH(NH₂)—CH(OH)(CH₃), —CH₂SC(O)—CH(NH₂)-benzyl, —CH₂SC(O)CH(NH₂)-4-hydroxybenzyl, and —CH₂SC(O)CH(NH₂)—(CH₂)₂SCH₃.

In yet another embodiment, $R^5$ is —C$_{0-3}$alkylene-SR$^{5a}$, where R$^{5a}$ is —C(O)—R$^{5aa}$, and R$^{5aa}$ is –2-pyrrolidine:

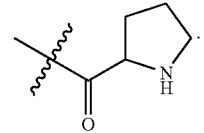

Thus, an example of $R^5$ is —CH₂S—C(±)-2-pyrrolidine.

In yet another embodiment, $R^5$ is —C$_{0-3}$alkylene-SR$^{5a}$, where R$^{5a}$ is —C(O)—R$^{5aa}$, and R$^{5aa}$ is —C$_{0-6}$alkylene-OR$^{5ab}$. In one embodiment, R$^{5ab}$ is H, such that R$^{5a}$ is —C(O)—C$_{0-6}$alkylene-OH. In another embodiment, R$^{5ab}$ is —C$_{1-6}$alkyl, such that R$^{5a}$ is —C(O)—C$_{0-6}$alkylene-OC$_{1-6}$alkyl, for example, $R^5$ can be —CH₂SC(O)—OCH₂CH₃. In yet another embodiment, $R^5$ is —C$_{0-3}$alkylene-SR$^{5a}$, where R$^{5a}$ is —C(O)—R$^{5aa}$, and R$^{5aa}$ is —OC$_{0-6}$alkylenearyl. In yet another embodiment, $R^5$ is —C$_{0-3}$alkylene-SR$^{5a}$, where R$^{5a}$ is —C(O)—R$^{5aa}$, and R$^{5aa}$ is —C$_{1-2}$alkylene-OC(O)—C$_{1-6}$alkyl; and in another embodiment, $R^5$ is —C$_{0-3}$alkylene-SR$^{5a}$, where R$^{5a}$ is —C(O)—R$^{5aa}$, and R$^{5aa}$ is —C$_{1-2}$alkylene-OC(O)—C$_{0-6}$alkylenearyl; and in still another embodiment, $R^5$ is —C$_{0-3}$alkylene-SR$^{5a}$, where R$^{5a}$ is —C(O)—R$^{5aa}$, and R$^{5aa}$ is —O—C$_{1-2}$alkylene-OC(O)—OC$_{1-6}$alkyl, for example, $R^5$ is —CH₂SC(O)O—CH(CH₃)OC(O)OCH(CH₃)₂.

In one embodiment, $R^5$ is —C$_{0-3}$alkylene-C(O)NR$^{5b}$R$^{5c}$. The R$^{5b}$ moiety is H, —OH, —OC(O)R$^{5ba}$, —CH₂COOH, —O-benzyl, -pyridyl, or —OC(S)NR$^{5bb}$R$^{5bc}$. R$^{5ba}$ is H, —C$_{1-6}$alkyl, aryl, —OCH₂-aryl (for example, —OCH₂-phenyl), —CH₂O-aryl (for example, —CH₂O-phenyl), or —NR$^{5bb}$R$^{5bc}$. The R$^{5bb}$ and R$^{5bc}$ moieties are independently selected from H and —C$_{1-4}$alkyl. In one embodiment, R$^{5b}$ is —OH or —OC(O)R$^{5ba}$, where —R$^{5ba}$ is —C$_{1-6}$alkyl. R$^{5c}$ is H, —C$_{1-6}$alkyl, or —C(O)R$^{5ca}$, where R$^{5ca}$ is H, —C$_{1-6}$alkyl, —C$_{3-7}$cycloalkyl, aryl, or heteroaryl. In one embodiment, R$^5$ is —C$_{0-3}$alkylene-C(O)NR$^{5b}$R$^{5c}$ and R$^{5c}$ is H. In one specific embodiment, R$^5$ is —C$_{0-3}$alkylene-C(O)NR$^{5b}$R$^{5c}$, where R$^{5b}$ is —OH and R$^{5c}$ is H, for example, R$^5$ can be —C(O)N(OH)H or —CH₂C(O)N(OH)H. In another embodiment, R$^5$ is —C$_{0-3}$ alkylene-C(O)NR$^{5b}$R$^{5c}$, where R$^{5b}$ is —OC(O)R$^{5ba}$, R$^{5ba}$ is —C$_{1-6}$alkyl, and R$^{5c}$ is H Thus, examples of R$^5$ include —C(O)N[OC(O)CH₃]H and —C(O)N[OC(O)C(CH₃)₃]H. In still another embodiment, R$^5$ is —C$_{0-3}$alkylene-C(O)NR$^{5b}$R$^{5c}$ and both R$^{5b}$ and R$^{5c}$ are H, for example, R$^5$ can be —C(O)NH₂. In yet another embodiment, R$^5$ is —C$_{0-3}$alkylene-C(O)NR$^{5b}$R$^{5c}$, where R$^{5b}$ is —OC(O)R$^{5ba}$, R$^{5ba}$ is —OCH₂-aryl or —CH₂O-aryl, and R$^{5c}$ is H. Thus, examples of R$^5$ include —CH₂—C(O)NH[OC(O)OCH₂-phenyl] and —CH₂—C(O)N[OC(O)CH₂O-phenyl]H. In another embodiment, R$^5$ is —C$_{0-3}$alkylene-C(O)NR$^{5b}$R$^{5c}$, where R$^{5b}$ is —OC(S)NR$^{5bb}$R$^{5bc}$, R$^{5bb}$ and R$^{5bc}$ are both —C$_{1-4}$alkyl, and R$^{5c}$ is H, for example, R$^5$ can be —CH₂—C(O)N[OC(S)N(CH₃)₂]H. In another embodiment, R$^5$ is —C$_{0-3}$alkylene-C(O)NR$^{5b}$R$^{5c}$, where R$^{5b}$ is —CH₂COOH and R$^{5c}$ is H, for example, R$^5$ can be —C(O)NH—(CH₂COOH).

In one embodiment, R$^5$ is —C$_{0-3}$alkylene-NR$^{5b}$—C(O)R$^{5d}$. The R$^{5d}$ moiety is H, —C$_{1-4}$alkyl, —C$_{0-3}$alkylenearyl, —NR$^{5da}$R$^{5db}$, —CH₂SH, or —O—C$_{1-6}$alkyl. The R$^{5da}$ and R$^{5db}$ moieties are independently selected from H and —C$_{1-4}$ alkyl. In one embodiment, R$^{5b}$ is —OH and R$^{5d}$ is H, for example, R$^5$ can be —CH₂—N(OH)C(O)H; and in another embodiment, R$^{5b}$ is —OH and R$^{5d}$ is —C$_{1-4}$alkyl, for example, R$^5$ can be —CH₂—N(OH)C(O)CH₃. In another embodiment, R$^{5b}$ is H and R$^{5d}$ is —CH₂SH, for example, R$^5$ can be —C$_{0-1}$alkylene-NHC(O)CH₂SH, for example, —NHC(O)CH₂SH or —CH₂NHC(O)—CH₂SH.

In yet another embodiment, R$^5$ is —NH—C$_{0-1}$alkylene-P(O)(OR$^{5e}$)₂. The R$^{5e}$ moiety is H, —C$_{1-6}$alkyl, —C$_{1-3}$alkylenearyl, —C$_{1-3}$alkyleneheteroaryl, —C$_{3-7}$cycloalkyl, —CH(CH₃)—O—C(O)R$^{5ea}$,

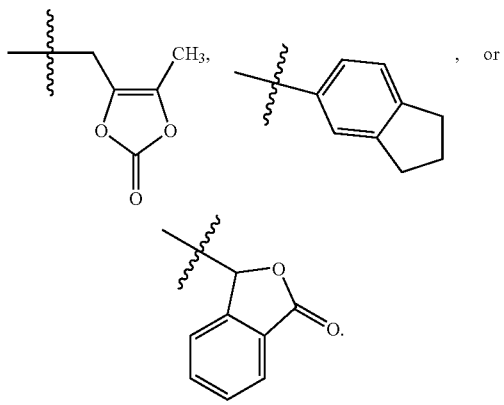

The R$^{5ea}$ group is —O—C$_{1-6}$alkyl, —O—C$_{3-7}$cycloalkyl, —NR$^{5eb}$R$^{5ec}$, or —CH(NH₂)CH₂COOCH₃. R$^{5eb}$ and R$^{5ec}$ are independently selected from H, —C$_{1-4}$alkyl, and —C$_{1-3}$alkylenearyl (for example, benzyl). R$^{5eb}$ and R$^{5ec}$ may also be taken together to form —(CH₂)$_{3-6}$—. In one embodiment, R$^{5e}$ is H, for example, R$^5$ can be —NH—CH₂—P(O)(OH)₂.

In one embodiment, R$^5$ is —C$_{0-3}$alkylene-P(O)OR$^{5e}$R$^{5f}$. The R$^{5f}$ moiety is H, —C$_{1-4}$alkyl, —C$_{0-3}$alkylenearyl, —C$_{1-3}$alkylene-NR$^{5fa}$R$^{5fb}$, or —C$_{1-3}$alkylene(aryl)-C$_{0-3}$alkylene-NR$^{5fa}$R$^{5fb}$. The R$^{5fa}$ and R$^{5fb}$ groups are independently selected from H and —C$_{1-4}$alkyl. In one embodiment, R$^{5e}$ is H, for example, R$^5$ can be —C$_{0-3}$alkylene-P(O)(OH)R$^{5f}$.

In one embodiment, R$^5$ is —C$_{0-2}$alkylene-CHR$^{5g}$—COOH. The R$^{5g}$ moiety is H, C$_{1-6}$alkyl, —C$_{1-3}$alkylenearyl, or —CH₂—O—(CH₂)₂—OCH₃. In one embodiment, R$^{5g}$ is —CH₂—O—(CH₂)₂—OCH₃, for example R$^5$ can be —CH₂—CH—[CH₂—O—(CH₂)₂—OCH₃]—COOH. In another embodiment, R$^{5g}$ is H, for example R$^5$ can be —CH₂COOH.

In one embodiment, R$^5$ is —C$_{0-3}$alkylene-C(O)NR$^{5h}$—CHR$^{5i}$—COOH. The R$^{5h}$ moiety is H or —C$_{1-4}$alkyl. The R$^{5i}$ moiety is H, —C$_{1-4}$alkyl, or —C$_{0-3}$alkylenearyl. In one embodiment, R$^{5h}$ is H and R$^{5i}$ is —C$_{0-3}$alkylenearyl, and the aryl is optionally substituted with 1 to 3 substituents such as —OH, for example, R$^5$ can be —C(O)NH—CH(CH₂-phenyl-OH)(COOH).

In another embodiment, R$^5$ is —C$_{0-3}$alkylene-S—SR$^{5j}$, and the R$^{5j}$ moiety is —C$_{1-6}$alkyl, aryl, or —CH₂CH(NH₂) COOH. Examples of such R$^5$ groups include —C$_{0-3}$alkylene-S—S—CH₃, —C$_{0-3}$alkylene-S—S-phenyl, and —C$_{0-3}$alkylene-S—S—CH₂CH(NH₂)—COOH.

R$^6$ is selected from —C$_{1-6}$alkyl, —CH₂O(CH₂)₂OCH₃, —C$_{1-6}$alkylene-O—C$_{1-6}$alkyl, —C$_{0-3}$alkylenearyl, —C$_{0-3}$alkyleneheteroaryl, and —C$_{0-3}$alkylene-C$_{3-7}$cycloalkyl. In one particular embodiment, R$^6$ is selected from —C$_{1-6}$alkyl, —C$_{0-3}$alkylenearyl, and —C$_{0-3}$alkylene-C$_{3-7}$cycloalkyl. Each alkyl and each aryl in R$^6$ is optionally substituted with 1 to 7 fluoro atoms, where the term "alkyl" is intended to include divalent alkylene groups such as those present in —C$_{1-6}$alkylene-O—C$_{1-6}$alkyl and —C$_{0-3}$alkylene-C$_{3-7}$cycloalkyl, for example. In addition, each aryl and heteroaryl in R$^6$ may be substituted with 1 to 3-OH, —C$_{1-6}$alkyl, —C$_{2-4}$ alkenyl, —C$_{2-4}$alkynyl, —CN, halo, —O—C$_{1-6}$alkyl, —S—C$_{1-6}$alkyl, —S(O)—C$_{1-6}$alkyl, —S(O)₂—C$_{1-4}$alkyl, -phenyl, —NO₂, —NH₂, —NH—C$_{1-6}$alkyl, or —N(C$_{1-6}$ alkyl)₂ groups. Further, each of the aforementioned alkyl, alkenyl and alkynyl groups may be substituted with 1 to 5 fluoro atoms.

In one embodiment, R$^6$ is —C$_{1-6}$alkyl, for example, —CH₃, —CH₂CH₃, —CH(CH₃)₂, —(CH₂)₂CH₃, —(CH₂)₃CH₃, —CH(CH₃)CH₂CH₃, —CH₂CH(CH₃)₂, —CH₂C(CH₃)₃, —(CH₂)₂CH(CH₃)₂, and —(CH₂)₄CH₃. As noted above, each alkyl in R$^6$ is optionally substituted with 1 to 7 fluoro atoms. Examples of such fluoro-substituted R$^6$ groups include —(CH₂)₂CF₃ and —(CH₂)₃CF₃.

In another embodiment, R$^6$ is —CH₂O(CH₂)₂OCH₃. In still another one embodiment, R$^6$ is —C$_{1-6}$alkylene-O—C$_{1-6}$ alkyl, for example, —OCH₃ and —CH₂OCH₃.

In one embodiment, R$^6$ is —C$_{0-3}$alkylenearyl, for example, phenyl, benzyl, —CH₂-biphenyl, —(CH₂)₂-phenyl and —CH₂-naphthalen-1-yl. The aryl may be substituted with 1 to 3 substituents. Thus, other examples of R$^6$ include monosubstituted groups such as, methylbenzyl, chlorobenzyl, fluorobenzyl, fluorophenyl, bromobenzyl, iodobenzyl, benzyl-CF₃, 2-trifluoromethyl-benzyl, -benzyl-CN, and -benzyl-NO₂; and di-substituted groups such as di-chlorobenzyl and di-fluorobenzyl. Each aryl may also be substituted with 1 to 7 fluoro atoms. Thus, other examples of R$^6$ include penta-fluorobenzyl.

In one particular embodiment, R$^6$ is selected from —C$_{1-6}$ alkyl and —C$_{0-3}$alkylenearyl (e.g., benzyl).

In one embodiment, R$^6$ is —C$_{0-3}$alkyleneheteroaryl, for example, —CH₂-pyridyl, —CH₂-furanyl, —CH₂-thienyl, and —CH$_2$-thiophenyl. In another embodiment, R$^6$ is —C$_{0-3}$alkylene-C$_{3-7}$cycloalkyl, for example, —CH$_2$-cyclopropyl, cyclopentyl, —CH$_2$-cyclopentyl, -cyclohexyl, and —CH$_2$-cyclohexyl.

R$^7$ is H or is taken together with R$^6$ to form —C$_{3-8}$cycloalkyl. In one embodiment, R$^7$ is H. In another embodiment, R$^7$ is taken together with R$^6$ to form —C$_{3-8}$cycloalkyl, for example cyclopentyl.

One particular embodiment of the invention provides for an active compound of formula I where Ar**—COOH represents Ar—R$^1$ and R$^5$ is —C$_{0-3}$alkylene-SH. One corresponding prodrug (prodrug A) can contain a thioester linkage, which can be cleaved in vivo to form the —COOH(R$^1$) and —C$_{0-3}$alkylene-SH(R$^5$) moieties. Another corresponding prodrug (prodrug B, where Z is —C$_{1-6}$alkylene, optionally substituted with one or more moieties such as hydroxyl, phenyl, carboxyl, and so forth), contains both an ester and a thioester group, which can be similarly cleaved in vivo, but which also releases a physiologically acceptable acid such as α-hydroxy acid (Z is —CH$_2$—), β-hydroxy acid (Z is —(CH$_2$)$_2$—), (R)-2-hydroxypropionic or lactic acid (Z is —CH(CH$_3$)—), (R)-hydroxyphenyl acetic or mandelic acid (Z is —CH(phenyl)-), salicylic acid (Z is -phenylene-), 2,3-dihydroxysuccinic or tartaric acid (Z is —CH[CH(OH)(COOH)]—), citric acid (Z is —C[CH$_2$COOH]$_2$—), hydroxy bis- and hydroxy-tris acids, and so forth.

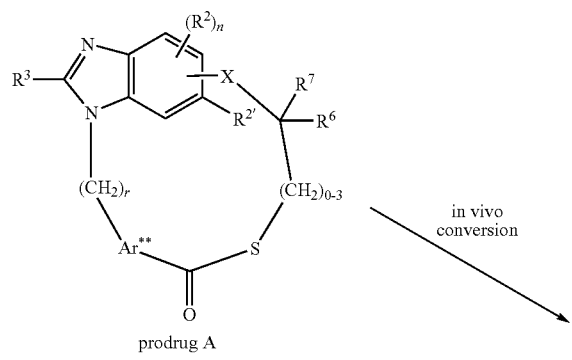

prodrug A

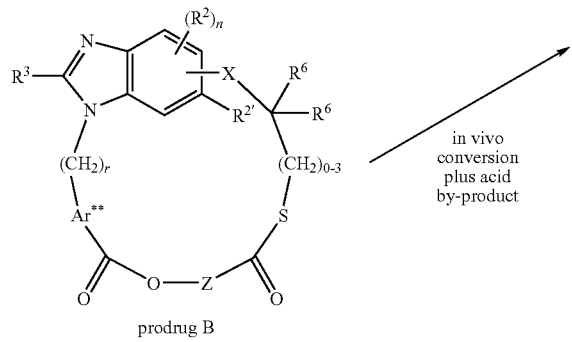

prodrug B

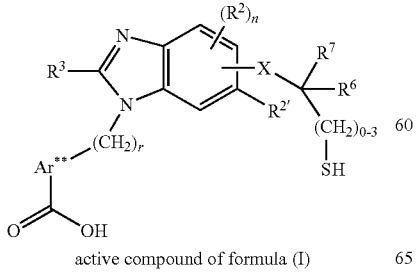

active compound of formula (I)

Yet another corresponding prodrug (prodrug C) is a dimer form of prodrug A, thus containing two thioester linkages, which can both be cleaved in vivo to form two active moieties, each containing the —COOH(R$^1$) and —C$_{0-3}$alkylene-SH (R$^5$) moieties.

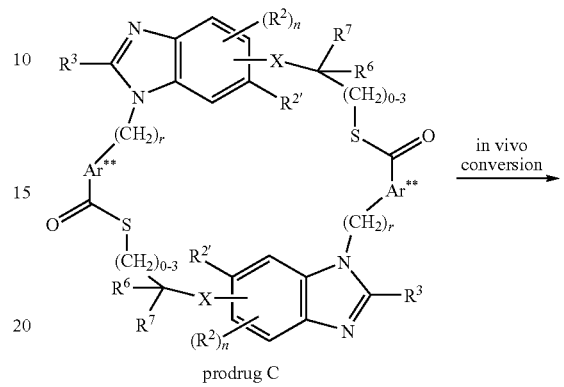

prodrug C

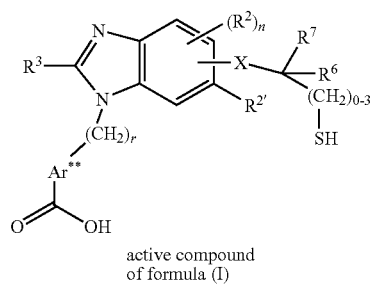

active compound of formula (I)

Another embodiment of the invention provides for an active compound of formula I where R$^5$ is —C$_{0-3}$alkylene-SH, and the prodrug (prodrug D) is a dimer form of the compound:

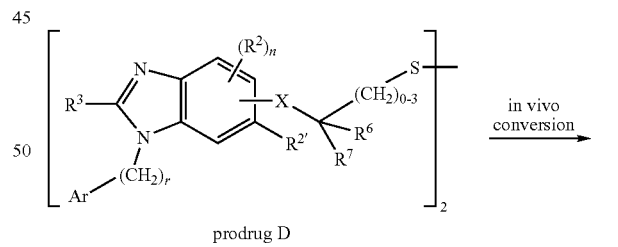

prodrug D

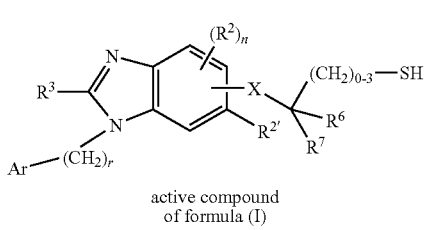

active compound of formula (I)

In one particular embodiment, the compound of formula I is the species embodied in formula Ia, Ib, or Ic:

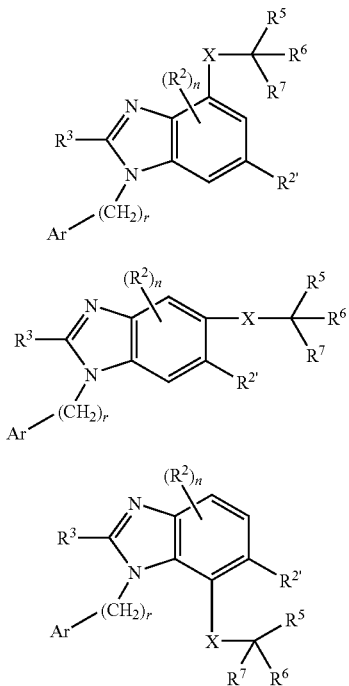

where Ar, r, n, $R^2$, $R^{2'}$, $R^3$, X, and $R^{5-7}$ are as defined for formula I.

In one particular embodiment, the compound of formula I is the species embodied in formula II:

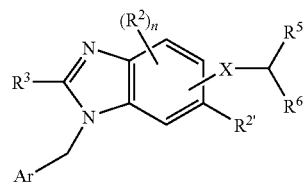

where: Ar is an aryl group selected from:

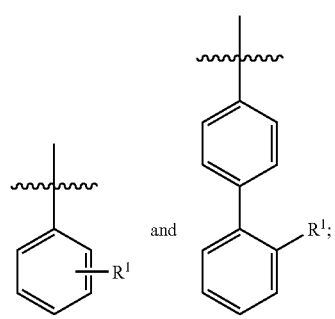

$R^1$ is selected from —COOH and tetrazol-5-yl; n is 0, or n is 1 and $R^2$ is —$C_{1-6}$alkyl; $R^{2'}$ is selected from H and —C(O)— $C_{1-6}$alkyl; $R^3$ is selected from —$C_{1-10}$alkyl and —$C_{0-5}$alkylene-O—$C_{1-5}$alkylene-H; X is —$C_{1-2}$alkylene-, where one —$CH_2$— moiety in the alkylene is replaced with a —$NR^{4a}$—C(O)— or —C(O)—$NR^{4a}$— moiety, where $R^{4a}$ is selected from H, —OH, and —$C_{1-4}$alkyl; $R^5$ is selected from —$C_{0-3}$alkylene-$SR^{5a}$ and —$C_{0-3}$alkylene-C(O)$NR^{5b}R^{5c}$; where $R^{5a}$ is selected from H and —C(O)—$C_{1-6}$alkyl; $R^{5b}$ is selected from H, —OH, and —OC(O)—$C_{1-6}$alkyl; and $R^{5c}$ is selected from H and —$C_{1-6}$alkyl; and $R^6$ is selected from —$C_{1-6}$alkyl and —$C_{0-3}$alkylenearyl. Any of these moieties may be optionally substituted as set forth in the description for formula I.

In one particular embodiment, the compound of formula II is the species embodied in formula IIa, IIb, or IIc:

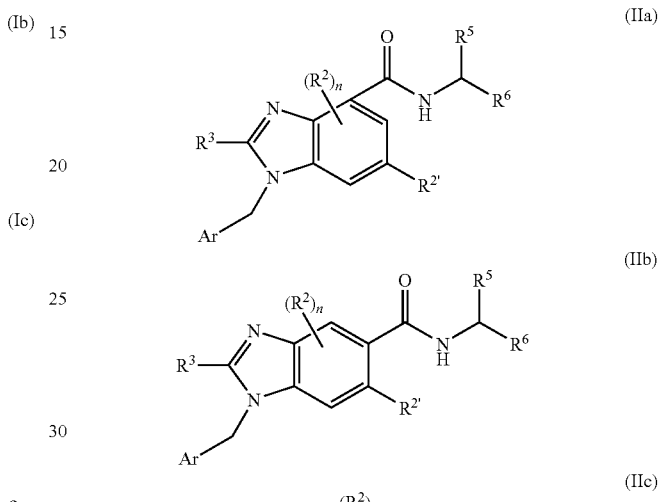

where Ar, n, $R^2$, $R^{2'}$, $R^3$, and $R^{5-6}$ are as defined for formula II.

In one particular embodiment, X is —C(O)—NH—. In another aspect, this embodiment has formula Ia, Ib, Ic, II, IIa, IIb, or IIc.

In another particular embodiment, $R^1$ is selected from —COOH, —$NHSO_2R^{1b}$, —$SO_2NHR^{1d}$, —$SO_2OH$, —C(O)NH—$SO_2R^{1c}$, —$P(O)(OH)_2$, —CN, —O—$CH(R^{1e})$—COOH, tetrazol-5-yl,

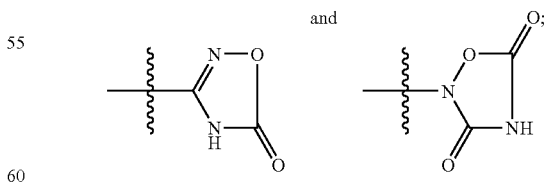

where $R^{1b}$, $R^{1c}$, $R^{1d}$, and $R^{1e}$, are as defined for formula I. In one particular embodiment, $R^1$ is selected from —$COOR^{1a}$, —$SO_2NHR^{1d}$, and tetrazol-5-yl. In another embodiment, $R^1$ is selected from —COOH, —$SO_2NHC(O)$—$C_{1-6}$alkyl, and tetrazol-5-yl. In another aspect, this embodiment has formula Ia, Ib, Ic, II, IIa, IIb, or IIc.

In one particular embodiment, $R^1$ is —COOR$^{1a}$, where $R^{1a}$ is —C$_{1-6}$alkyl, —C$_{1-3}$alkylenearyl, —C$_{1-3}$alkyleneheteroaryl, —C$_{3-7}$cycloalkyl, —CH(C$_{1-4}$alkyl)OC(O)R$^{1aa}$, —C$_{0-6}$alkylenemorpholine,

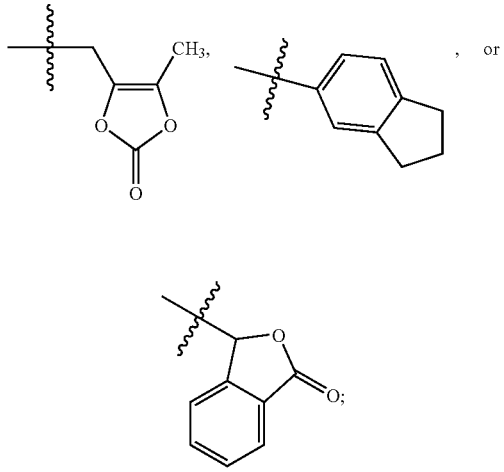

where $R^{1aa}$ is as defined for formula I. In one aspect of the invention, these compounds may find particular utility as prodrugs or as intermediates in the synthetic procedures described herein. In one particular embodiment, $R^1$ is —COO—C$_{1-6}$alkyl. In another aspect, these embodiments have formula Ia, Ib, Ic, II, IIa, IIb, or IIc.

In one embodiment, $R^5$ is selected from —C$_{0-3}$alkylene-SR$^{5a}$, —C$_{0-3}$alkylene-C(O)NR$^{5b}$R$^{5c}$, —C$_{0-3}$alkylene-NR$^{5b}$—C(O)R$^{5d}$, —NH—C$_{0-1}$alkylene-P(O)(OR$^{5e}$)$_2$, C$_{0-3}$alkylene-P(O)OR$^{5e}$R$^{5f}$, —C$_{0-2}$alkylene-CHR$^{5g}$—COOH, and —C$_{0-3}$alkylene-C(O)NR$^{5h}$—CHR$^{5i}$COOH; where $R^{5a}$ is H, $R^{5b}$ is —OH, $R^{5c}$ is H, $R^{5d}$ is H, $R^{5e}$ is H; and $R^{5f}$, $R^{5g}$ $R^{5h}$, $R^{5i}$ are as defined for formula I. More particularly, in one embodiment, $R^5$ is selected from —C$_{0-1}$alkylene-SH, —C$_{0-1}$alkylene-C(O)—N(OH)H, and —C$_{0-3}$alkylene-N(OH)—C(O)H. In another aspect, $R^5$ is selected from —C$_{0-3}$alkylene-SR$^{5a}$ and —C$_{0-3}$alkylene-C(O)NR$^{5b}$R$^{5c}$, where $R^{5a}$ is H; $R^{5b}$ is —OH. In one particular embodiment, $R^{5c}$ is H. In another aspect, this embodiment has formula Ia, Ib, Ic, II, IIa, IIb, or IIc.

In yet another embodiment, $R^5$ is selected from —C$_{0-3}$alkylene-SR$^{5a}$, —C$_{0-3}$alkylene-C(O)NR$^{5b}$R$^{5c}$, —C$_{0-3}$alkylene-NR$^{5b}$—C(O)R$^{5d}$, —NH—C$_{0-1}$alkylene-P(O)(OR$^{5e}$)$_2$, —C$_{0-3}$alkylene-P(O)OR$^{5e}$R$^{5f}$, and —C$_{0-3}$alkylene-S—SR$^{5j}$; where $R^{5a}$ is —C(O)—R$^{5aa}$; $R^{5b}$ is H, —OC(O)R$^{5ba}$, —CH$_2$COOH, —O-benzyl, -pyridyl, or —OC(S)NR$^{5bb}$R$^{5bc}$; $R^{5e}$ is —C$_{1-6}$alkyl, —C$_{1-3}$alkylenearyl, —C$_{1-3}$alkyleneheteroaryl, —C$_{3-7}$cycloalkyl, —CH(CH$_3$)—O—C(O)R$^{5ea}$,

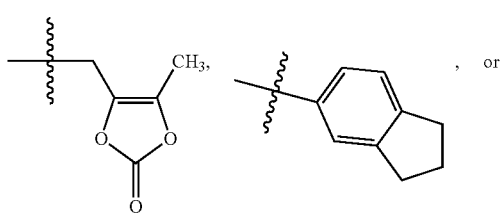

-continued

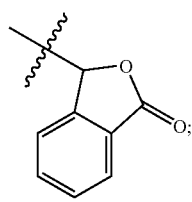

and where $R^{5aa}$, $R^{5ba}$, $R^{5bb}$, $R^{5bc}$, $R^{5c}$, $R^{5d}$, $R^{5ea}$, $R^{5f}$, and $R^{5j}$ are as defined for formula I. In one aspect of the invention, these compounds may find particular utility as prodrugs or as intermediates in the synthetic procedures described herein. In another aspect, these embodiments have formula Ia, Ib, Ic, II, IIa, IIb, or IIc.

In one particular embodiment, $R^5$ is selected from —C$_{0-3}$alkylene-SR$^{5a}$ and —C$_{0-3}$alkylene-C(O)NR$^{5b}$R$^{5c}$; where $R^{5a}$ is selected from H and —C(O)—C$_{1-6}$alkyl; $R^{5b}$ is selected from H, —OH, and —OC(O)—C$_{1-6}$alkyl; and $R^{5c}$ is selected from H and —C$_{1-6}$alkyl. In another aspect, this embodiment has formula Ia, Ib, Ic, II, IIa, IIb, or IIc.

In another embodiment, $R^1$ is selected from —COOR$^{1a}$ where $R^{1a}$ is H, —NHSO$_2$R$^{1b}$, —SO$_2$NHR$^{1d}$, —SO$_2$OH, —C(O)NH—SO$_2$R$^{1c}$, —P(O)(OH)$_2$, —CN, —O—CH(R$^{1e}$)—COOH, tetrazol-5-yl,

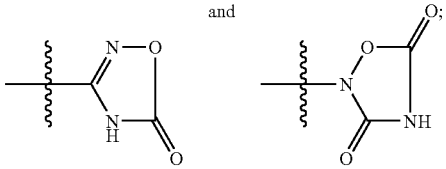

$R^5$ is selected from —C$_{0-3}$alkylene-SR$^{5a}$, —C$_{0-3}$alkylene-C(O)NR$^{5b}$R$^{5c}$, and —C$_{0-3}$alkylene-NR$^{5b}$—C(O)R$^{5d}$, —NH—C$_{0-1}$alkylene-P(O)(OR$^{5e}$)$_2$, —C$_{0-3}$alkylene-P(O)OR$^{5e}$R$^{5f}$, —C$_{0-2}$alkylene-CHR$^{5g}$—COOH, and —C$_{0-3}$alkylene-C(O)NR$^{5h}$—CHR$^{5i}$COOH; $R^{5a}$ is H, $R^{5b}$ is OH, $R^{5c}$ is H, $R^{5d}$ is H, $R^{5e}$ is H; and $R^{5f}$, $R^{5g}$, $R^{5h}$, $R^{5i}$ are as defined for formula I. In one particular embodiment, $R^1$ is selected from —COOH, —SO$_2$NHR$^{1d}$, and tetrazol-5-yl; and $R^5$ is selected from —C$_{0-3}$alkylene-SH, and —C$_{0-3}$alkylene-C(O)N(OH)H. In another aspect, these embodiments have formula Ia, Ib, Ic, II, IIa, IIb, or IIc.

In another embodiment, $R^1$ is —COOR$^{1a}$, where $R^{1a}$ is —C$_{1-6}$alkyl, —C$_{1-3}$alkylenearyl, —C$_{1-3}$alkyleneheteroaryl, —C$_{3-7}$cycloalkyl, —CH(C$_{1-4}$alkyl)OC(O)R$^{1aa}$, —C$_{0-6}$alkylenemorpholine,

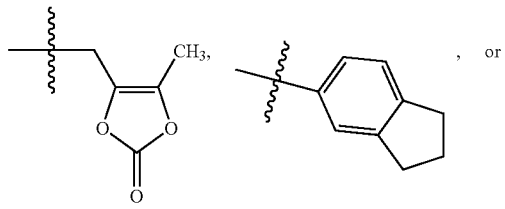

-continued

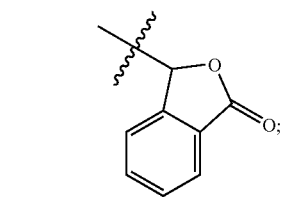

R⁵ is selected from —C₀₋₃alkylene-SR⁵ᵃ, —C₀₋₃alkylene-C(O)NR⁵ᵇR⁵ᶜ, —C₀₋₃alkylene-NR⁵ᵇ—C(O)R⁵ᵈ, —NH—C₀₋₁ alkylene-P(O)(OR⁵ᵉ)₂, —C₀₋₃alkylene-P(O)OR⁵ᵉR⁵ᶠ, and —C₀₋₃alkylene-S—SR⁵ʲ; where R⁵ᵃ is —C(O)—R⁵ᵃᵃ; R⁵ᵇ is H, —OC(O)R⁵ᵇᵃ, —CH₂COOH, —O-benzyl, -pyridyl, or —OC(S)NR⁵ᵇᵇR⁵ᵇᶜ; R⁵ᵉ is —C₁₋₆alkyl, —C₁₋₃alkylenearyl, —C₁₋₃alkyleneheteroaryl, —C₃₋₇cycloalkyl, —CH(CH₃)—O—C(O)R⁵ᵉᵃ,

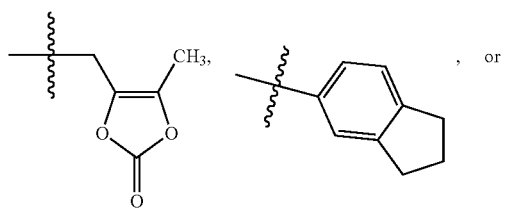

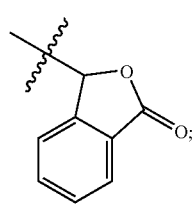

and where R⁵ᵃᵃ, R⁵ᵇᵃ, R⁵ᵇᵇ, R⁵ᵇᶜ, R⁵ᶜ, R⁵ᵈ, R⁵ᵉᵃ, R⁵ᶠ, and R⁵ʲ are as defined for formula I. In another aspect, this embodiment has formula Ia, Ib, Ic, II, IIa, IIb, or IIc.

A particular group of compounds of formula I are those disclosed in U.S. Provisional Application No. 61/007,129, filed on Dec. 11, 2007. This group includes compounds of formula (I'):

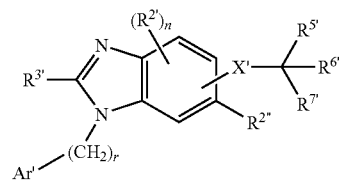

where: r is 0, 1 or 2; Ar' is an aryl group selected from:

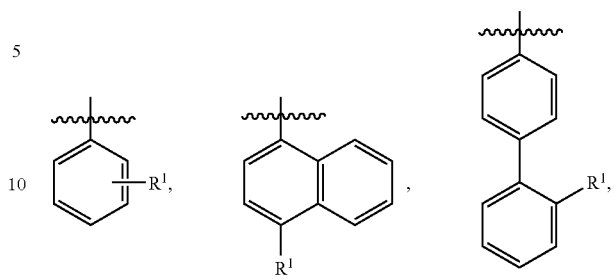

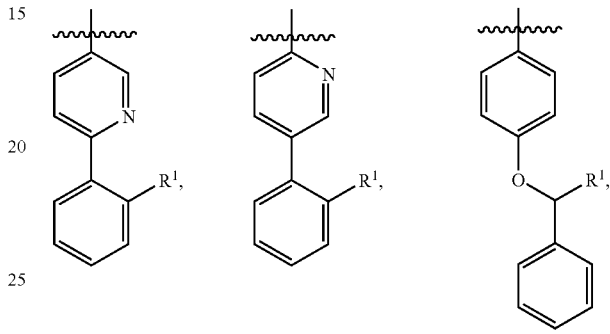

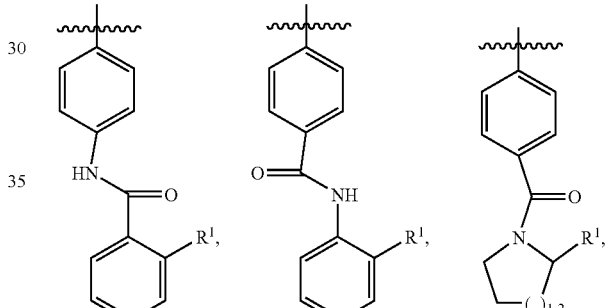

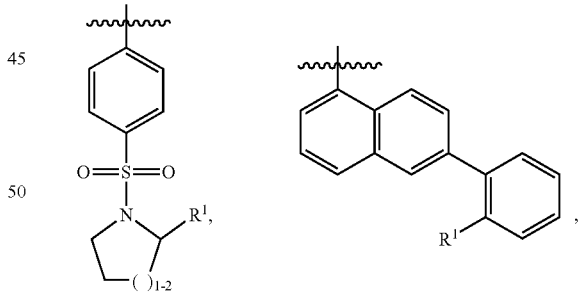

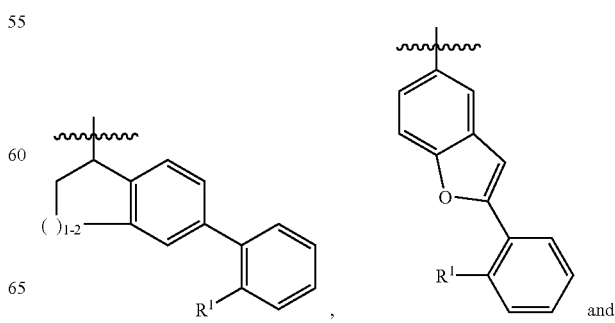

-continued

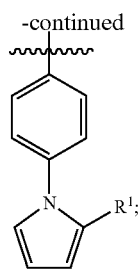

R[1t] is selected from —COOR[1a], —NHSO$_2$R[1b], —SO$_2$NHR[1d], —SO$_2$OH, —C(O)NH—SO$_2$R[1c], —P(O)(OH)$_2$, —CN, —OCH(R[1e])—COOH, tetrazol-5-yl,

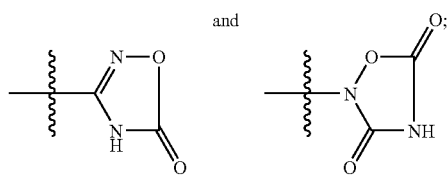

R[1a] is H, —C$_{1-6}$alkyl, —C$_{1-3}$alkylenearyl, —C$_{1-3}$alkyleneheteroaryl, —C$_{3-7}$cycloalkyl, —CH(C$_{1-4}$alkyl)OC(O)R[1a'], —C$_{0-6}$alkylenemorpholine,

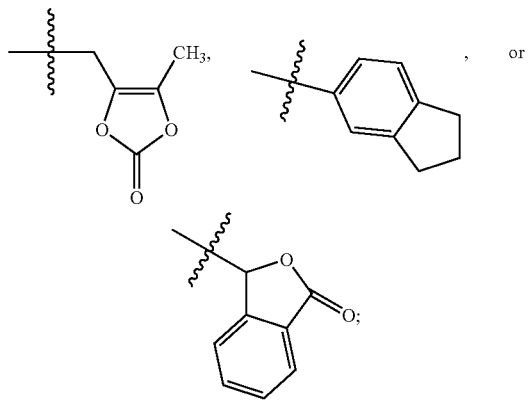

R[1a'] is —O—C$_{1-6}$alkyl, —O-cycloalkyl, —NR[1a"]R[1a'''], or —CH(NH$_2$)CH$_2$COOCH$_3$; R[1a"] and R[1a'''] are independently selected from H, —C$_{1-6}$alkyl, and benzyl, or are taken together as —(CH$_2$)$_{3-6}$—; R[1b] is R[1c] or —NHC(O)R[1c]; R[1c] is —C$_{1-6}$alkyl, —C$_{0-6}$alkylene-O—R[1c'], —C$_{1-5}$alkylene-NR[1c"]R[1c'''], or —C$_{0-4}$alkylenearyl; R[1c'] is H, —C$_{1-6}$alkyl, or —O—C$_{1-6}$alkyl; R[1c"] and R[1c'''] are independently selected from H and —C$_{1-6}$alkyl, or are taken together as —(CH$_2$)$_2$—O—(CH$_2$)$_2$— or —(CH$_2$)$_2$—N[C(O)CH$_3$]-(CH$_2$)$_2$—; R[1d] is H, R[1c], —C(O)R[1c], or —C(O)NHR[1c]; R[1e] is —C$_{1-4}$alkyl or aryl; n is 0, 1, 2 or 3; each R[2t] is independently selected from —CH$_2$OH, halo, —NO$_2$, —C$_{1-6}$alkyl, —C$_{2-6}$alkenyl, —C$_{3-6}$cycloalkyl, —CN, —C(O)R[2a], —C$_{0-5}$alkylene-OR[2b], —C$_{0-5}$alkylene-NR[2c]R[2d], —C$_{0-3}$alkylenearyl, and —C$_{0-3}$alkyleneheteroaryl; R[2a] is H, —C$_{1-6}$alkyl, —C$_{3-6}$cycloalkyl, —C$_{0-3}$alkylenearyl, OR[2b], or —NR[2c]R[2d]; R[2b] is H, —C$_{1-6}$alkyl, —C$_{3-6}$cycloalkyl, or —C$_{0-1}$alkylenearyl; and R[2c] and R[2d] are independently selected from H, —C$_{1-4}$alkyl, and —C$_{0-1}$alkylenearyl; R[2"] is selected from H and R[2]; R[3t] is selected from —C$_{1-10}$alkyl, —C$_{2-10}$alkenyl, —C$_{3-10}$alkynyl, —C$_{0-3}$alkylene-C$_{3-7}$cycloalkyl, —C$_{2-3}$alkenylene-C$_{3-7}$cycloalkyl, —C$_{2-3}$alkynylene-C$_{3-7}$cycloalkyl, —C$_{0-5}$alkylene-NR[3a]C$_{0-5}$alkylene-R[3b], —C$_{0-5}$alkylene-O—C$_{0-5}$alkylene-R[3b], —C$_{1-5}$alkylene-S—C$_{1-5}$alkylene-R[3b], and —C$_{0-3}$alkylenearyl; R[3a] is H, —C$_{1-6}$alkyl, —C$_{3-6}$cycloalkyl, or —C$_{0-3}$alkylenearyl; and R[3b] is H, —C$_{1-6}$alkyl, —C$_{3-6}$cycloalkyl, —C$_{2-4}$alkenyl, —C$_{2-4}$alkynyl, or aryl; X' is —C$_{1-12}$alkylene-, where at least one —CH$_2$— moiety in the alkylene is replaced with a —NR[4a]—C(O)— or —C(O)—NR[4a]— moiety, where R[4a] is selected from H, —OH, and —C$_{1-4}$alkyl; R[5t] is selected from —C$_{0-3}$alkylene-SR[5a], —C$_{0-3}$alkylene-C(O)NR[5e]R[5f], —C$_{0-3}$alkylene-NR[5b]—C(O)R[5d], —NH—C$_{0-1}$alkylene-P(O)(OR[5e])$_2$, —C$_{0-3}$alkylene-P(O)OR[5e]R[5f], —C$_{0-2}$alkylene-CHR[5g]—COOH and —C$_{0-3}$alkylene-C(O)NR[5h]—CHR[5i]—COOH; R[5a] is H or —C(O)—R[5a']; R[5a'] is —C$_{1-6}$alkyl, —C$_{0-6}$alkylene-C$_{3-7}$cycloalkyl, —C$_{0-6}$alkylenearyl, —C$_{0-6}$alkyleneheteroaryl, —C$_{0-6}$alkylenemorpholine, —C$_{0-6}$alkylenepiperazine-CH$_3$, —CH(NH$_2$)-aa where aa is an amino acid side chain, -2-pyrrolidine, —C$_{0-6}$alkylene-OR[5a"], —OC$_{0-6}$alkylenearyl, —C$_{1-2}$alkylene-OC(O)—C$_{1-6}$alkyl, —C$_{1-2}$alkylene-OC(O)—C$_{0-6}$alkylenearyl, or —C$_{1-2}$alkylene-OC(O)—OC$_{1-6}$alkyl; R[5a"] is H or —C$_{1-6}$alkyl; R[5b] is H, —OH, —OC(O)R[5b'], —CH$_2$COOH, —O-benzyl, -pyridyl, or —OC(S)NR[5b"]R[5b'''']; R[5b'] is —C$_{1-6}$alkyl, —OCH$_2$-aryl, —CH$_2$O-aryl, or —NR[5b"]R[5b'''']; R[5b"] and R[5b''''] are independently selected from H and —C$_{1-4}$alkyl; R[5c] is H, —C$_{1-6}$alkyl, or —C(O)—R[5c']; R[5c'] is —C$_{1-6}$alkyl, —C$_{3-7}$cycloalkyl, aryl, or heteroaryl; R[5d] is H, —C$_{1-4}$alkyl, —C$_{0-3}$alkylenearyl, —NR[5d']R[5d"], —CH$_2$SH, or —O—C$_{1-6}$alkyl; R[5d'] and R[5d"] are independently selected from H and —C$_{1-4}$alkyl; R[5e] is H, —C$_{1-6}$alkyl, —C$_{1-3}$alkylenearyl, —C$_{1-3}$alkyleneheteroaryl, —C$_{3-7}$cycloalkyl, —CH(CH$_3$)OC(O)R[5e'],

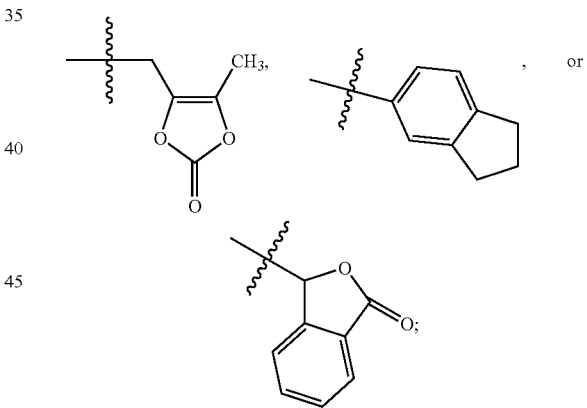

R[5e'] is —O—C$_{1-6}$alkyl, —O-cycloalkyl, —NR[5e"]R[5e'''], or —CH(NH$_2$)CH$_2$COOCH$_3$; R[5e"] and R[5e'''] are independently selected from H, —C$_{1-4}$alkyl, and —C$_{1-3}$alkylenearyl, or are taken together as —(CH$_2$)$_{3-6}$—; R[5f] is H, —C$_{1-4}$alkyl, —C$_{0-3}$alkylenearyl, —C$_{1-3}$alkylene-NR[5f']R[5f"], or —C$_{1-3}$alkylene(aryl)-C$_{0-3}$alkylene-NR[5f']R[5f"]; R[5f'] and R[5f"] are independently selected from H and —C$_{1-4}$alkyl; R[5g] is H, —C$_{1-6}$lkyl, —C$_{1-3}$alkylenearyl, or —CH$_2$—O—(CH$_2$)$_2$—OCH$_3$; R[5h] is H or —C$_{1-4}$alkyl; and R[5i] is H, —C$_{1-4}$alkyl, or —C$_{0-3}$alkylenearyl; R[6t] is selected from —C$_{1-6}$alkyl, —CH$_2$O(CH$_2$)$_2$OCH$_3$, —C$_{1-6}$alkylene-O—C$_{1-6}$alkyl, —C$_{0-3}$alkylenearyl, —C$_{0-3}$alkyleneheteroaryl, and —C$_{0-3}$alkylene-C$_{3-7}$cycloalkyl; and R[7t] is H or is taken together with R[6] to form —C$_{3-8}$cycloalkyl; wherein each —CH$_2$— group in —(CH$_2$)$_r$— is optionally substituted with 1 or 2 substituents independently selected from —C$_{1-4}$alkyl and fluoro; each carbon atom in the alkylene moiety in X is optionally substituted with one or more $R^{4b}$ groups and one —$CH_2$— moiety in X may be replaced with a group selected from —$C_{4-8}$cycloalkylene-, —$CR^{4d}$=CH—, and —CH=$CR^{4d}$—; wherein $R^{4b}$ is selected from —$C_{0-5}$alkylene-$COOR^{4c}$, —$C_{1-6}$alkyl, —$C_{0-1}$alkylene-$CONH_2$, —$C_{1-2}$alkylene-OH, —$C_{0-3}$alkylene-$C_{3-7}$cycloalkyl, 1H-indol-3-yl, benzyl, and hydroxybenzyl, where $R^{4c}$ is H or —$C_{1-4}$alkyl; and $R^{4d}$ is selected from —$CH_2$-thiophene and phenyl; each alkyl and each aryl in $R^1$, $R^2$, $R^{2'}$, $R^3$, $R^{4a-4d}$, and $R^{5-6}$ is optionally substituted with 1 to 7 fluoro atoms; each ring in Ar and each aryl in $R^1$, $R^2$, $R^{2'}$, $R^3$, and $R^{5-6}$ is optionally substituted with 1 to 3 substituents independently selected from —OH, —$C_{1-6}$alkyl, —$C_{2-4}$alkenyl, —$C_{2-4}$alkynyl, —CN, halo, —O—$C_{1-6}$alkyl, —S—$C_{1-6}$alkyl, —S(O)—$C_{1-6}$alkyl, —S(O)$_2$—$C_{1-4}$alkyl, -phenyl, —$NO_2$, —$NH_2$, —NH—$C_{1-6}$alkyl and —N($C_{1-6}$alkyl)$_2$, wherein each alkyl, alkenyl and alkynyl is optionally substituted with 1 to 5 fluoro atoms; and pharmaceutically acceptable salts thereof.

In addition, particular compounds of formula I that are of interest include those set forth in the Examples below, as well as the pharmaceutically acceptable salts thereof.

DEFINITIONS

When describing the compounds, compositions, methods and processes of the invention, the following terms have the following meanings unless otherwise indicated. Additionally, as used herein, the singular forms "a," "an," and "the" include the corresponding plural forms unless the context of use clearly dictates otherwise. The terms "comprising", "including," and "having" are intended to be inclusive and mean that there may be additional elements other than the listed elements. All numbers expressing quantities of ingredients, properties such as molecular weight, reaction conditions, and so forth used herein are to be understood as being modified in all instances by the term "about," unless otherwise indicated. Accordingly, the numbers set forth herein are approximations that may vary depending upon the desired properties sought to be obtained by the present invention. At least, and not as an attempt to limit the application of the doctrine of equivalents to the scope of the claims, each number should at least be construed in light of the reported significant digits and by applying ordinary rounding techniques.

The term "alkyl" means a monovalent saturated hydrocarbon group which may be linear or branched. Unless otherwise defined, such alkyl groups typically contain from 1 to 10 carbon atoms and include, for example, —$C_{1-4}$alkyl, —$C_{1-6}$alkyl, and —$C_{1-10}$alkyl. Representative alkyl groups include, by way of example, methyl, ethyl, n-propyl, isopropyl, n-butyl, s-butyl, isobutyl, t-butyl, n-pentyl, n-hexyl, n-heptyl, n-octyl, n-nonyl, n-decyl and the like.

When a specific number of carbon atoms is intended for a particular term used herein, the number of carbon atoms is shown preceding the term as subscript. For example, the term "—$C_{1-6}$alkyl" means an alkyl group having from 1 to 6 carbon atoms, and the term "—$C_{3-7}$cycloalkyl" means a cycloalkyl group having from 3 to 7 carbon atoms, respectively, where the carbon atoms are in any acceptable configuration.

The term "alkylene" means a divalent saturated hydrocarbon group that may be linear or branched. Unless otherwise defined, such alkylene groups typically contain from 0 to 12 carbon atoms and include, for example, —$C_{0-1}$alkylene-, —$C_{0-2}$alkylene-, —$C_{0-3}$alkylene-, —$C_{0-5}$alkylene-, —$C_{0-6}$alkylene-, —$C_{1-2}$alkylene- and —$C_{1-12}$alkylene-. Representative alkylene groups include, by way of example, methylene, ethane-1,2-diyl ("ethylene"), propane-1,2-diyl, propane-1,3-diyl, butane-1,4-diyl, pentane-1,5-diyl and the like. It is understood that when the alkylene term include zero carbons such as —$C_{0-1}$alkylene- or —$C_{0-5}$alkylene-, such terms are intended to include the absence of carbon atoms, that is, the alkylene group is not present except for a covalent bond attaching the groups separated by the alkylene term.

The term "alkylthio" means a monovalent group of the formula —S-alkyl, where alkyl is as defined herein. Unless otherwise defined, such alkylthio groups typically contain from 2 to 10 carbon atoms and include, for example, —S—$C_{1-4}$alkyl and —S—$C_{1-6}$alkyl. Representative alkylthio groups include, by way of example, ethylthio, propylthio, isopropylthio, butylthio, s-butylthio and t-butylthio.

The term "alkenyl" means a monovalent unsaturated hydrocarbon group which may be linear or branched and which has at least one, and typically 1, 2 or 3, carbon-carbon double bonds. Unless otherwise defined, such alkenyl groups typically contain from 2 to 10 carbon atoms and include, for example, —$C_{2-4}$alkenyl and —$C_{2-10}$alkenyl. Representative alkenyl groups include, by way of example, ethenyl, n-propenyl, isopropenyl, n-but-2-enyl, n-hex-3-enyl and the like. The term "alkenylene" means a divalent alkenyl group, and includes groups such as —$C_{2-3}$alkenylene-.

The term "alkoxy" means a monovalent group of the formula —O-alkyl, where alkyl is as defined herein. Unless otherwise defined, such alkoxy groups typically contain from 2 to 10 carbon atoms and include, for example, —O—$C_{1-4}$alkyl and —O—$C_{1-6}$alkyl. Representative alkoxy groups include, by way of example, methoxy, ethoxy, n-propoxy, isopropoxy, n-butoxy, sec-butoxy, isobutoxy, t-butoxy and the like.

The term "alkynyl" means a monovalent unsaturated hydrocarbon group which may be linear or branched and which has at least one, and typically 1, 2 or 3, carbon-carbon triple bonds. Unless otherwise defined, such alkynyl groups typically contain from 2 to 10 carbon atoms and include, for example, —$C_{2-4}$alkynyl and —$C_{3-10}$alkynyl. Representative alkynyl groups include, by way of example, ethynyl, n-propynyl, n-but-2-ynyl, n-hex-3-ynyl and the like. The term "alkynylene" means a divalent alkynyl group and includes groups such as —$C_{2-3}$alkynylene-.

Amino acid residues are often designated as —C(O)—CHR—NH—, where the R moiety is referred to as the "amino acid side chain." Thus, for the amino acid valine, HO—C(O)—CH[—CH($CH_3$)$_2$]—$NH_2$, the side chain is —CH($CH_3$)$_2$. The term "amino acid side chain" is intended to include side chains of the twenty common naturally occurring amino acids: alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine. Of particular interest are the side chains of non-polar amino acids such as isoleucine, leucine, and valine.

The term "aryl" means a monovalent aromatic hydrocarbon having a single ring (e.g., phenyl) or fused rings. Fused ring systems include those that are fully unsaturated (e.g., naphthalene) as well as those that are partially unsaturated (e.g., 1,2,3,4-tetrahydronaphthalene). Unless otherwise defined, such aryl groups typically contain from 6 to 10 carbon ring atoms and include, for example, —$C_{6-10}$aryl. Representative aryl groups include, by way of example, phenyl and naphthalene-1-yl, naphthalene-2-yl, and the like. The term "arylene" means a divalent aryl group such as phenylene.

The term "cycloalkyl" means a monovalent saturated carbocyclic hydrocarbon group. Unless otherwise defined, such cycloalkyl groups typically contain from 3 to 10 carbon atoms and include, for example, —$C_{3-5}$cycloalkyl, —$C_{3-6}$cycloalkyl and —$C_{3-7}$cycloalkyl. Representative cycloalkyl groups include, by way of example, cyclopropyl, cyclobutyl, cyclopentyl, cyclohexyl and the like. The term "cycloalkylene" means a divalent aryl group such as —$C_{4-8}$cycloalkylene.

The term "halo" means fluoro, chloro, bromo and iodo.

As used herein, the phrase "having the formula" or "having the structure" is not intended to be limiting and is used in the same way that the term "comprising" is commonly used.

The term "heteroaryl" means a monovalent aromatic group having a single ring or two fused rings and containing in the ring(s) at least one heteroatom (typically 1 to 3 heteroatoms) selected from nitrogen, oxygen or sulfur. Unless otherwise defined, such heteroaryl groups typically contain from 5 to 10 total ring atoms and include, for example, —$C_{2-9}$heteroaryl. Representative heteroaryl groups include, by way of example, monovalent species of pyrrole, imidazole, thiazole, oxazole, furan, thiophene, triazole, pyrazole, isoxazole, isothiazole, pyridine, pyrazine, pyridazine, pyrimidine, triazine, indole, benzofuran, benzothiophene, benzoimidazole, benzthiazole, quinoline, isoquinoline, quinazoline, quinoxaline and the like, where the point of attachment is at any available carbon or nitrogen ring atom.

The term "optionally substituted" means that group in question may be unsubstituted or it may be substituted one or several times, such as 1 to 3 times or 1 to 5 times. For example, an alkyl group that is "optionally substituted" with 1 to 5 fluoro atoms, may be unsubstituted, or it may contain 1, 2, 3, 4, or 5 fluoro atoms.

The term "pharmaceutically acceptable" refers to a material that is not biologically or otherwise unacceptable when used in the invention. For example, the term "pharmaceutically acceptable carrier" refers to a material that can be incorporated into a composition and administered to a patient without causing unacceptable biological effects or interacting in an unacceptable manner with other components of the composition. Such pharmaceutically acceptable materials typically have met the required standards of toxicological and manufacturing testing, and include those materials identified as suitable inactive ingredients by the U.S. Food and Drug administration.

The term "pharmaceutically acceptable salt" means a salt prepared from a base or an acid which is acceptable for administration to a patient, such as a mammal (e.g., salts having acceptable mammalian safety for a given dosage regime). However, it is understood that the salts covered by the invention are not required to be pharmaceutically acceptable salts, such as salts of intermediate compounds that are not intended for administration to a patient. Pharmaceutically acceptable salts can be derived from pharmaceutically acceptable inorganic or organic bases and from pharmaceutically acceptable inorganic or organic acids. In addition, when a compound of formula I contains both a basic moiety, such as an amine, pyridine or imidazole, and an acidic moiety such as a carboxylic acid or tetrazole, zwitterions may be formed and are included within the term "salt" as used herein. Salts derived from pharmaceutically acceptable inorganic bases include ammonium, calcium, copper, ferric, ferrous, lithium, magnesium, manganic, manganous, potassium, sodium, and zinc salts, and the like. Salts derived from pharmaceutically acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine and the like. Salts derived from pharmaceutically acceptable inorganic acids include salts of boric, carbonic, hydrohalic (hydrobromic, hydrochloric, hydrofluoric or hydroiodic), nitric, phosphoric, sulfamic and sulfuric acids. Salts derived from pharmaceutically acceptable organic acids include salts of aliphatic hydroxyl acids (e.g., citric, gluconic, glycolic, lactic, lactobionic, malic, and tartaric acids), aliphatic monocarboxylic acids (e.g., acetic, butyric, formic, propionic and trifluoroacetic acids), amino acids (e.g., aspartic and glutamic acids), aromatic carboxylic acids (e.g., benzoic, p-chlorobenzoic, diphenylacetic, gentisic, hippuric, and triphenylacetic acids), aromatic hydroxyl acids (e.g., o-hydroxybenzoic, p-hydroxybenzoic, 1-hydroxynaphthalene-2-carboxylic and 3-hydroxynaphthalene-2-carboxylic acids), ascorbic, dicarboxylic acids (e.g., fumaric, maleic, oxalic and succinic acids), glucoronic, mandelic, mucic, nicotinic, orotic, pamoic, pantothenic, sulfonic acids (e.g., benzenesulfonic, camphosulfonic, edisylic, ethanesulfonic, isethionic, methanesulfonic, naphthalenesulfonic, naphthalene-1,5-disulfonic, naphthalene-2,6-disulfonic and p-toluenesulfonic acids), xinafoic acid, and the like.

As used herein, the term "prodrug" is intended to mean an inactive (or significantly less active) precursor of a drug that is converted into its active form in the body under physiological conditions, e.g., by normal metabolic processes. The term is also intended to include certain protected derivatives of compounds of formula I that may be made prior to a final deprotection stage. Such compounds may not possess pharmacological activity at $AT_1$ and/or NEP, but may be administered orally or parenterally and thereafter metabolized in the body to form compounds of the invention which are pharmacologically active at $AT_1$ and/or NEP. Thus, all protected derivatives and prodrugs of compounds formula I are included within the scope of the invention. Prodrugs of compounds of formula I having a free carboxyl, sulfhydryl or hydroxy group can be readily synthesized by techniques that are well known in the art. These prodrug derivatives are then converted by solvolysis or under physiological conditions to be the free carboxyl, sulfhydryl and/or hydroxy compounds. Exemplary prodrugs include: esters including $C_{1-6}$alkylesters and aryl-$C_{1-6}$alkylesters, carbonate esters, hemi-esters, phosphate esters, nitro esters, sulfate esters, sulfoxides, amides, carbamates, azo-compounds, phosphamides, glycosides, ethers, acetals, ketals, and disulfides. In one embodiment, the compounds of formula I have a free sulfhydryl or a free carboxyl and the prodrug is an ester derivative.

The term "protected derivatives thereof" means a derivative of the specified compound in which one or more functional groups of the compound are protected or blocked from undergoing undesired reactions with a protecting or blocking group. Functional groups that may be protected include, by way of example, carboxy groups, amino groups, hydroxyl groups, thiol groups, carbonyl groups and the like. Representative protecting groups for carboxy groups include esters (such as a p-methoxybenzyl ester), amides and hydrazides; for amino groups, carbamates (such as t-butoxycarbonyl) and amides; for hydroxyl groups, ethers and esters; for thiol groups, thioethers and thioesters; for carbonyl groups, acetals and ketals; and the like. Such protecting groups are well-known to those skilled in the art and are described, for example, in T. W. Greene and G. M. Wuts, *Protective Groups in Organic Synthesis*, Third Edition, Wiley, New York, 1999, and references cited therein.

The term "solvate" means a complex or aggregate formed by one or more molecules of a solute, e.g., a compound of formula I or a pharmaceutically acceptable salt thereof, and one or more molecules of a solvent. Such solvates are typically crystalline solids having a substantially fixed molar ratio of solute and solvent. Representative solvents include, by way of example, water, methanol, ethanol, isopropanol, acetic acid and the like. When the solvent is water, the solvate formed is a hydrate.

The term "therapeutically effective amount" means an amount sufficient to effect treatment when administered to a patient in need thereof, i.e., the amount of drug needed to obtain the desired therapeutic effect. For example, a therapeutically effective amount for treating hypertension is an amount of compound needed to, for example, reduce, suppress, eliminate or prevent the symptoms of hypertension, or to treat the underlying cause of hypertension. In one embodiment, a therapeutically effective amount is that amount needed to reduce blood pressure or the amount needed to maintain normal blood pressure. On the other hand, the term "effective amount" means an amount sufficient to obtain a desired result, which may not necessary be a therapeutic result. For example, when studying a system comprising an $AT_1$ receptor, an "effective amount" may be the amount needed to antagonize the receptor.

The term "treating" or "treatment" as used herein means the treating or treatment of a disease or medical condition (such as hypertension) in a patient, such as a mammal (particularly a human) that includes one or more of the following: (a) preventing the disease or medical condition from occurring, such as by prophylactic treatment of a patient; (b) ameliorating the disease or medical condition, such as by eliminating or causing regression of the disease or medical condition in a patient; (c) suppressing the disease or medical condition, such as by slowing or arresting the development of the disease or medical condition in a patient; or (d) alleviating the symptoms of the disease or medical condition in a patient. For example, the term "treating hypertension" would include preventing hypertension from occurring, ameliorating hypertension, suppressing hypertension, and alleviating the symptoms of hypertension (e.g., lowering blood pressure). The term "patient" is intended to include those mammals, such as humans, that are in need of treatment or disease prevention, that are presently being treated for disease prevention or treatment of a specific disease or medical condition, as well as test subjects in which compounds of the invention are being evaluated or being used in a assay, for example an animal model.

All other terms used herein are intended to have their ordinary meaning as understood by those of ordinary skill in the art to which they pertain.

General Synthetic Procedures

Compounds of the invention can be prepared from readily available starting materials using the following general methods, the procedures set forth in the Examples, or by using other methods, reagents, and starting materials that are known to those of ordinary skill in the art. Although the following procedures may illustrate a particular embodiment of the invention, it is understood that other embodiments of the invention can be similarly prepared using the same or similar methods or by using other methods, reagents and starting materials known to those of ordinary skill in the art. It will also be appreciated that where typical or preferred process conditions (i.e., reaction temperatures, times, mole ratios of reactants, solvents, pressures, etc.) are given, other process conditions can also be used unless otherwise stated. While optimum reaction conditions will typically vary depending on various reaction parameters such as the particular reactants, solvents and quantities used, those of ordinary skill in the art can readily determine suitable reaction conditions using routine optimization procedures.

Additionally, as will be apparent to those skilled in the art, conventional protecting groups may be necessary or desired to prevent certain functional groups from undergoing undesired reactions. The choice of a suitable protecting group for a particular functional group as well as suitable conditions and reagents for protection and deprotection of such functional groups are well-known in the art. Protecting groups other than those illustrated in the procedures described herein may be used, if desired. For example, numerous protecting groups, and their introduction and removal, are described in T. W. Greene and G. M. Wuts, *Protective Groups in Organic Synthesis*, supra. More specifically, the following abbreviations and reagents are used in the schemes presented below:

$P^1$ represents an "amino-protecting group," a term used herein to mean a protecting group suitable for preventing undesired reactions at an amino group. Representative amino-protecting groups include, but are not limited to, t-butoxycarbonyl (BOC), trityl (Tr), benzyloxycarbonyl (Cbz), 9-fluorenylmethoxycarbonyl (Fmoc), formyl, trimethylsilyl (TMS), t-butyldimethylsilyl (TBDMS), and the like. Standard deprotection techniques are used to remove the $P^1$ group. For example, an N—BOC group can be removed using an acidic reagent such as TFA in DCM or HCl in 1,4-dioxane, while a Cbz group can be removed by employing catalytic hydrogenation conditions such as $H_2$ (1 atm) and 10% Pd/C in an alcoholic solvent ("$H_2$/Pd/C").

$P^2$ represents a "carboxy-protecting group," a term used herein to mean a protecting group suitable for preventing undesired reactions at a carboxy group. Representative carboxy-protecting groups include, but are not limited to, methyl, ethyl, t-butyl, benzyl (Bn), p-methoxybenzyl (PMB), 9-fluoroenylmethyl (Fm), trimethylsilyl (TMS), t-butyldimethylsilyl (TBDMS), diphenylmethyl (benzhydryl, DPM) and the like. Standard deprotection techniques and reagents are used to remove the $P^2$ group, and may vary depending upon which group is used. For example, NaOH is commonly used when $P^2$ is methyl, an acid such as TFA or HCl is commonly used when $P^2$ is t-butyl, and $H_2$/Pd/C may be used when $P^2$ is benzyl.

$P^3$ represents a "thiol-protecting group," a term used herein to mean a protecting group suitable for preventing undesired reactions at a thiol group. Representative thiol-protecting groups include, but are not limited to, ethers, esters such as —C(O)CH$_3$, and the like. Standard deprotection techniques and reagents such as NaOH, primary alkylamines, and hydrazine, may be used to remove the $P^3$ group.

$P^4$ represents a "tetrazole-protecting group," a term used herein to mean a protecting group suitable for preventing undesired reactions at a tetrazole group. Representative tetrazole-protecting groups include, but are not limited to trityl, benzoyl, and diphenylmethyl. Standard deprotection techniques and reagents such as TFA in DCM or HCl in 1,4-dioxane are used to remove the $P^4$ group.

$P^5$ represents a "hydroxyl-protecting group," a term used herein to mean a protecting group suitable for preventing undesired reactions at a hydroxyl group. Representative hydroxyl-protecting groups include, but are not limited to $C_{1-6}$alkyls, silyl groups including tri$C_{1-6}$alkylsilyl groups, such as trimethylsilyl (TMS), triethylsilyl (TES), and tert-butyldimethylsilyl (TBDMS); esters (acyl groups) including $C_{1-6}$alkanoyl groups, such as formyl, acetyl, and pivaloyl, and aromatic acyl groups such as benzoyl; arylmethyl groups such as benzyl (Bn), p-methoxybenzyl (PMB), 9-fluorenyl-methyl (Fm), and diphenylmethyl (benzhydryl, DPM); and the like. Standard deprotection techniques and reagents are used to remove the $P^5$ group, and may vary depending upon which group is used. For example, $H_2$/Pd/C is commonly used when $P^5$ is benzyl, while NaOH is commonly used when $P^5$ is an acyl group.

$P^6$ represents a "sulfonamide-protecting group," a term used herein to mean a protecting group suitable for preventing undesired reactions at a sulfonamide group. Representative sulfonamide-protecting groups include, but are not limited to t-butyl and acyl groups. Exemplary acyl groups include aliphatic lower acyl groups such as the formyl, acetyl, phenylacetyl, butyryl, isobutyryl, valeryl, isovaleryl and pivaloyl groups, and aromatic acyl groups such as the benzoyl and 4-acetoxybenzoyl. Standard deprotection techniques and reagents are used to remove the $P^6$ group, and may vary depending upon which group is used. For example, HCl is commonly used when $P^6$ is t-butyl, while NaOH is commonly used when $P^6$ is an acyl group.

$P^7$ represents a "phosphate-protecting group or phosphinate-protecting group," a term used herein to mean a protecting group suitable for preventing undesired reactions at a phosphate or phosphinate group. Representative phosphate and phosphinate protecting groups include, but are not limited to $C_{1-4}$alkyls, aryl (e.g., phenyl) and substituted aryls (e.g., chlorophenyl and methylphenyl). The protected group can be represented by —P(O)(OR)$_2$, where R is a group such as a $C_{1-6}$alkyl or phenyl. Standard deprotection techniques and reagents such as TMS-I/2,6-lutidine, and $H_2$/Pd/C are used to remove the $P^7$ group such as ethyl, and benzyl, respectively.

In addition, L is used to designate a "leaving group," a term used herein to mean a functional group or atom which can be displaced by another functional group or atom in a substitution reaction, such as a nucleophilic substitution reaction. By way of example, representative leaving groups include chloro, bromo and iodo groups; sulfonic ester groups, such as mesylate, triflate, tosylate, brosylate, nosylate and the like; and acyloxy groups, such as acetoxy, trifluoroacetoxy and the like.

Suitable bases for use in these schemes include, by way of illustration and not limitation, potassium carbonate, calcium carbonate, sodium carbonate, triethylamine, pyridine, 1,8-diazabicyclo-[5.4.0]undec-7-ene (DBU), N,N-diisopropylethylamine (DIPEA), sodium hydroxide, potassium hydroxide, potassium t-butoxide, and metal hydrides.

Suitable inert diluents or solvents for use in these schemes include, by way of illustration and not limitation, tetrahydrofuran (THF), acetonitrile (MeCN), N,N-dimethylformamide (DMF), dimethyl sulfoxide (DMSO), toluene, dichloromethane (DCM), chloroform (CHCl$_3$), carbon tetrachloride (CCl$_4$), 1,4-dioxane, methanol, ethanol, water, and the like.

Suitable carboxylic acid/amine coupling reagents include benzotriazol-1-yloxytris(dimethylamino)phosphonium hexafluorophosphate (BOP), benzotriazol-1-yloxytripyrrolidinophosphonium hexafluorophosphate (PyBOP), O-(7-azabenzotriazol-1-yl-N,N,N',N' tetramethyluronium hexafluorophosphate (HATU), dicyclohexylcarbodiimide (DCC), N-(3-dimethylaminopropyl)-N'-ethylcarbodiimide (EDC), carbonyldiimidazole (CDI), and the like. Coupling reactions are conducted in an inert diluent in the presence of a base, and are performed under conventional amide bond-forming conditions.

All reactions are typically conducted at a temperature within the range of about –78° C. to 100° C., for example at room temperature. Reactions may be monitored by use of thin layer chromatography (TLC), high performance liquid chromatography (HPLC), and/or LCMS until completion. Reactions may be complete in minutes, or may take hours, typically from 1-2 hours and up to 48 hours. Upon completion, the resulting mixture or reaction product may be further treated in order to obtain the desired product. For example, the resulting mixture or reaction product may be subjected to one or more of the following procedures: concentrating or partitioning (e.g., between EtOAc and water or between 5% THF in EtOAc and IM phosphoric acid); extraction (e.g., with EtOAc, CHCl$_3$, DCM, chloroform); washing (e.g., with saturated aqueous NaCl, saturated NaHCO$_3$, Na$_2$CO$_3$ (5%), CHCl$_3$ or 1M NaOH); drying (e.g., over MgSO$_4$, over Na$_2$SO$_4$, or in vacuo); filtering; crystallizing (e.g., from EtOAc and hexane); being concentrated (e.g., in vacuo); and/or purification (e.g., silica gel chromatography, flash chromatography, preparative HPLC, reverse phase-HPLC, or crystallization).

By way of illustration, compounds of formula I, as well as their salts, solvates, and prodrugs can be prepared by one or more of the following exemplary processes. One method of preparing compounds of the invention involves coupling compound (1) and (2), following by reacting with compound (4), with an optional deprotection step when $R^{1*}$ is a protected form of $R^1$ and/or $R^{5*}$ is a protected form of $R^5$, as depicted in Scheme I ($R^2$ is typically a moiety such as —CH$_3$ and $R^{2'}$ is typically H):

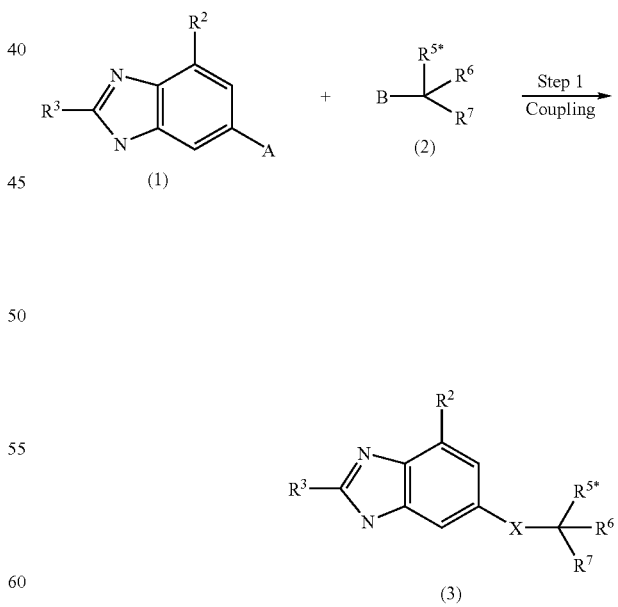

Another method of preparing compounds of the invention involves coupling compound (6) and (7), then reacting the product with compound (9), with an optional deprotection step, as depicted in Scheme II (n is typically 0 and $R^{2'}$ is typically H).

Scheme II

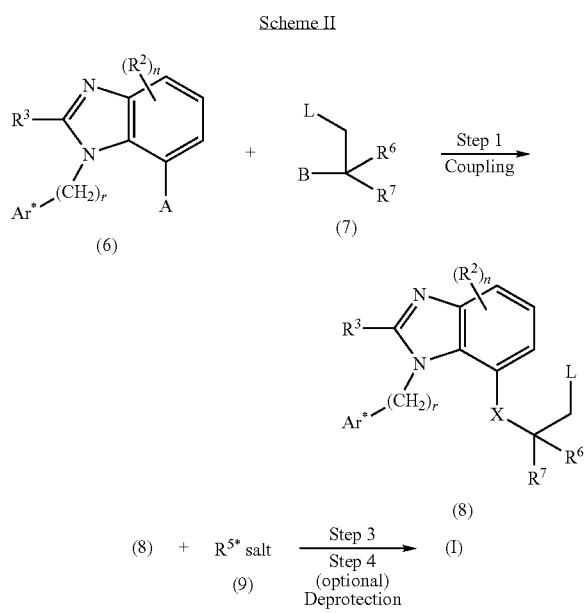

The X moiety contains one or more amide groups, and therefore the compounds of the invention may be formed by a coupling reaction under conventional amide bond-forming conditions, followed by a deprotection step if needed. In Schemes I and II, the A and B moieties couple to form X, and the sum of a and b is in the range of 0 to 11. Thus, one moiety comprises an amine group and one moiety comprises a carboxylic acid group, i.e., A is —$(CH_2)_a$—$NH_2$ and B is —$(CH_2)_b$—COOH or A is —$(CH_2)_a$—COOH and B is —$(CH_2)_b$—$NH_2$. For example, to synthesize a compound of formula I where X is —CONH—, A would be —COOH and B would be —$NH_2$. Similarly, A as —$NH_2$ and B as —COOH would couple to form —NHCO— as the X moiety. A and B can be readily modified if a longer X is desired, whether it contains an alkylene portion or additional amide groups. For example, A as —$CH_2NH_2$ and B as —COOH would couple to form —$CH_2$NHCO— as the X moiety.

It is understood that the carbon atoms in the —$(CH_2)_a$ and —$(CH_2)_b$ groups make up the "X" linker. Therefore, these carbon atoms may be substituted with one or more $R^{4b}$ groups. Furthermore, one —$CH_2$— group in the —$(CH_2)_a$ or the —$(CH_2)_b$ group may be replaced with a —$C_{4-8}$cycloalkylene-, —$CR^{4d}$=CH—, or —CH=$CR^{4d}$— group.

Ar* represents Ar—$R^{1*}$, where $R^{1*}$ may represent $R^1$ as defined herein, or a protected form of $R^1$ (e.g., -tetrazol-5-yl-$P^4$ or —C(O)O—$P^2$ such as —C(O)O—$C_{1-6}$alkyl), or a precursor of $R^1$ (e.g., —CN that is then converted to tetrazole, or nitro that is then converted to amino from which the desired $R^1$ is prepared). $R^{5*}$ represents $R^5$ as defined herein, or a protected form of $R^5$. Therefore, when $R^{1*}$ represents $R^1$ and $R^{5*}$ represents $R^5$, the reaction is complete after the coupling step.

On the other hand, when $R^{1*}$ represents a protected form of $R^1$ and/or $R^{5*}$ represents a protected form of $R^5$, a subsequent global or sequential deprotection step would yield the non-protected compound. Similarly, when $R^{1*}$ represents a precursor of $R^1$, a subsequent conversion step would yield the desired compound. Reagents and conditions for the deprotection vary with the nature of protecting groups in the compound. Typical deprotection conditions when $R^{5*}$ represents $C_{0-3}$alkylene-S—$P^3$, include treating the compound with NaOH in an alcoholic solvent at 0° C. or room temperature to yield the non-protected compound. Typical deprotection conditions when $R^{1*}$ represents C(O)O—$P^2$ where $P^2$ refers to t-butyl include treating the compound with TFA in DCM at room temperature to yield the non-protected compound. Thus, one method of preparing compounds of the invention involves coupling compounds (1) and (2), with an optional deprotection step when $R^{1*}$ is a protected form of $R^1$ and/or $R^5$ is a protected form of $R^5$, thus forming a compound of formula I or a pharmaceutically acceptable salt thereof.

Examples of compound (1) include the commercially available 7-methyl-2-propyl-3H-benzoimidazole-5-carboxylic acid. Examples of compound (2) include (R)-3-amino-N-benzyloxy-4-phenylbutyramide. Examples of compound (4) include 4-bromomethylbenzoic acid methyl ester and 5-(4'-bromomethylbiphenyl-2-yl)-1-trityl-1H-tetrazole. Examples of compound (6) include the commercially available 2-ethoxy-3-[2'-(1H-tetrazol-5-yl)-biphenyl-4-ylmethyl]-3H-benzimidazole-4-carboxylic acid. Examples of compound (7) include 1-chloromethyl-3-methylbutylamine hydrochloride. Compound 9 is a salt form of the $R^5$ or $R^{5*}$ substituent, for example, potassium thioacetate. Starting materials and reagents are commercially available or can be readily synthesized by techniques known in the art, as well as by the methods described below and in the Examples.

Preparation of Compound (2)

Compound (2) is readily synthesized by following techniques described in the literature, for example, Neustadt et al. (1994) *J. Med. Chem.* 37:2461-2476 and Moree et al. (1995) *J. Org. Chem.* 60: 5157-69, as well as by using the exemplary procedures described below. Examples of compound (2), depicted without chirality, include:

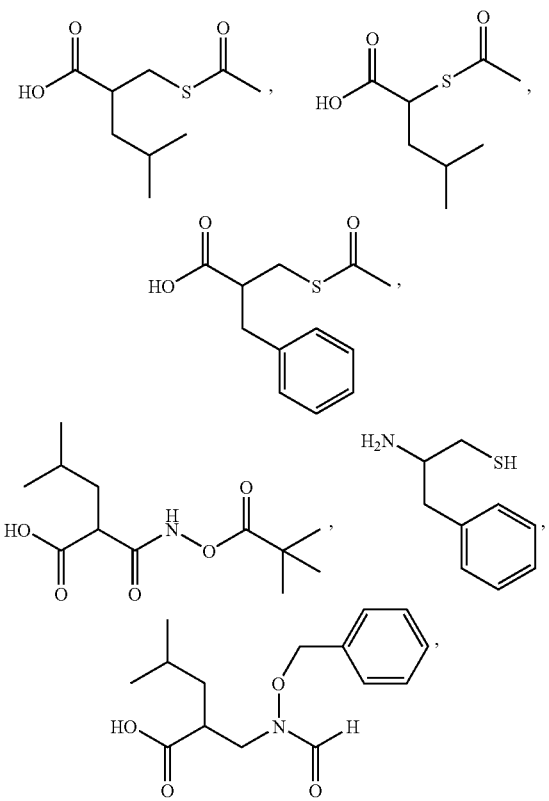

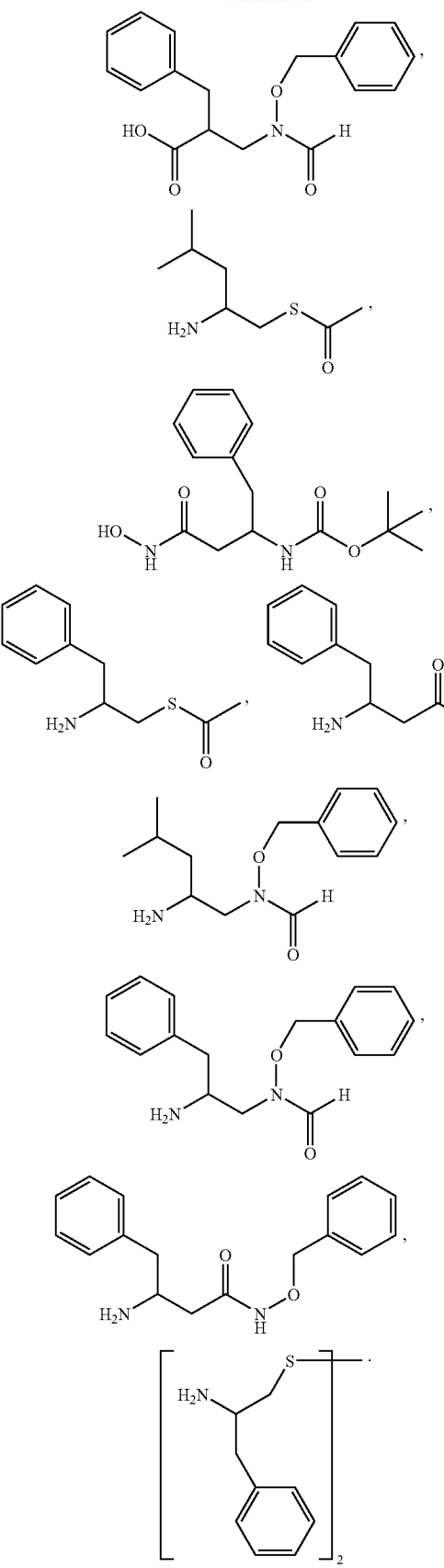

Since compound (2) has a chiral center, it may be desirable to synthesize a particular stereoisomer, and examples are as follows.

Preparation of Chiral Amino Hydroxamate Compound ($2^i$)

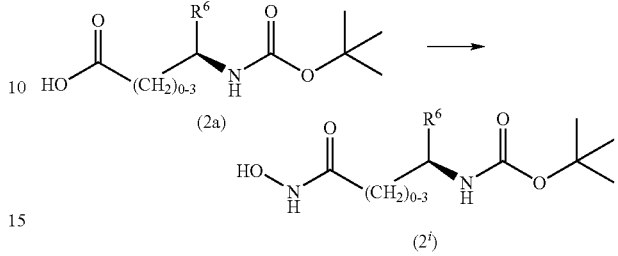

A base such as DIPEA and a coupling agent such as EDC are added to a solution of compound (2a) in DMF containing HOBt and hydroxylamine hydrochloride. The mixture is stirred at room temperature until the reaction is complete, then concentrated in vacuo. The resulting material is distributed between 5% THF in EtOAc and 1M phosphoric acid. The organic layer is collected and washed with a base such as 1M NaOH. The alkaline aqueous layer is then acidified (e.g., with 1M phosphoric acid), and extracted with EtOAc. The organic layer is evaporated and the residue purified by silica gel chromatography to afford compound ($2^i$). Examples of compound (2a) include (R)-3-t-butoxycarbonylamino-4-phenylbutyric acid.

Preparation of Sulfanyl Acid Compound ($2^{ii}$)

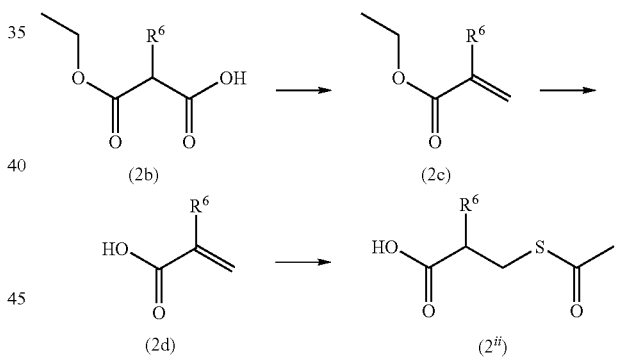

Compound (2b) is mixed with diethylamine and cooled in an ice bath. An aqueous formaldehyde solution (37%) is then added, and the mixture stirred at 0° C. for ~2 hours, warmed to room temperature and stirred overnight. The mixture is then extracted with ether, washed, dried, and evaporated to dryness, to provide compound (2c). Compound (2c) is then dissolved in 1,4-dioxane, and a 1M NaOH solution is added. The mixture is stirred at room temperature until the reaction is complete. The organic solvent is removed in vacuo, and the aqueous residue is rinsed with EtOAc and acidified to pH~1 with concentrated HCl. The product is extracted with EtOAc, dried, and evaporated to dryness to yield compound (2d). Compound (2d) is combined with thiolacetic acid (10 mL), and the mixture was stirred at 80° C. until the reaction is complete, then concentrated to dryness to yield Compound ($2^{ii}$), which is dissolved in toluene and concentrated to remove any trace of thiolacetic acid. Examples of (2b) include 2-benzylmalonic acid monoethyl ester ($R^6$=benzyl) and 2-isobutylmalonic acid monoethyl ester ($R^6$=isobutyl).

Preparation of Chiral Amino Sulfhydryl Dimer Compound (2$^{iii}$)

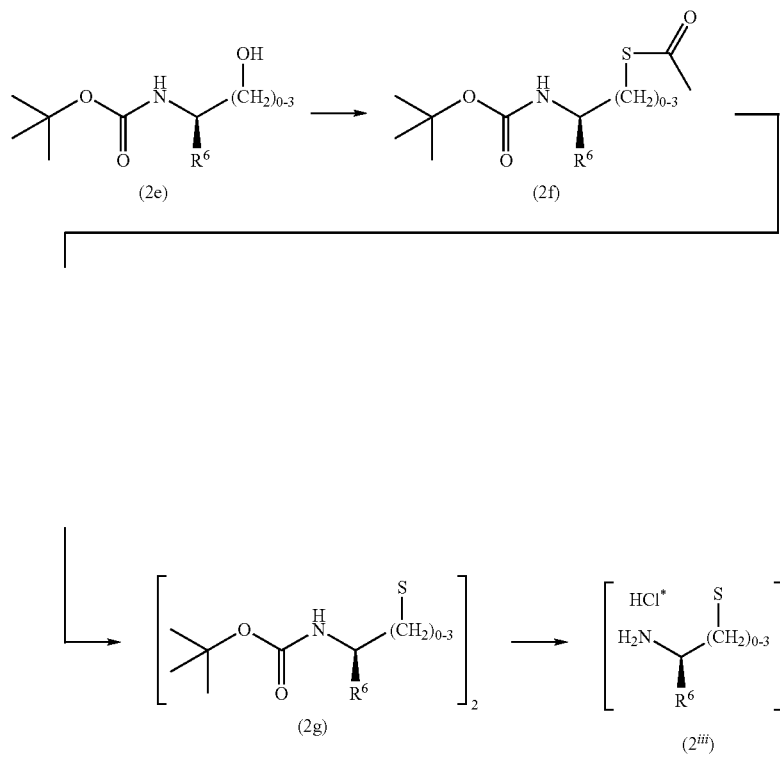

Diisopropyl azodicarboxylate is added to a solution of triphenylphosphine in a solvent such as THF, cooled in an ice bath. The solution is stirred and compound (2e) and thioacetic acid are added. The mixture is first stirred at 0° C., then at room temperature until the reaction is complete. The mixture is stripped, diluted with EtOAc, and washed. The organic layer is dried and the filtrate evaporated to dryness. The resulting material is flash chromatographed to provide compound (2f). Compound (2f) is dissolved in a suitable solvent, followed by the addition of a base such as 1M LiOH. Air is bubbled through the solution for 1 hour followed by the addition of solvent. The mixture is stirred at room temperature until the reaction is complete. The solution is then acidified to pH5, for example with acetic acid. The precipitate is filtered and rinsed producing compound (2g) as a solid, which is suspended in MeCN, then concentrated in vacuo. The recovered material is dissolved in 4M HCl in 1,4-dioxane and stirred at room temperature until the reaction is complete. The mixture is then concentrated under reduced pressure, and triturated with EtOAc. The product is filtered, washed, and dried in vacuo to provide compound (2$^{iii}$). Examples of compound (2e) include ((R)-1-benzyl-2-hydroxyethyl)carbamic acid t-butyl ester.

Preparation of Chiral Sulfanyl Acid Compound (2$^{iv}$)

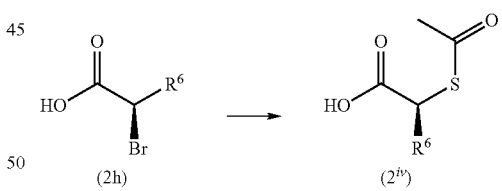

Compound (2h) is formed by dissolving a compound such as D-leucine (for R$^6$=isobutyl, for example) in 3M HBr (aqueous) and cooled to 0° C. A solution of sodium nitrite in water is added, and the mixture is stirred at 0° C. until the reaction is complete (~2.5 hours). The mixture is then extracted with EtOAc, washed, dried, filtered, and concentrated to afford compound (2h). Compound (2h) is combined with potassium thioacetate and DMF, and the mixture stirred at room temperature until the reaction is complete. Water is added, and the mixture is then extracted, washed, dried, filtered, and concentrated to provide compound (2$^{iv}$). The product is purified by silica gel chromatography. Examples of compound (2h) include (R)-2-bromo-4-methylpentanoic acid. Examples of compound (2$^{iv}$) include (S)-2-acetylsulfanyl-4-methylpentanoic acid.

Preparation of Chiral Sulfanyl Acid Compound (2ᵛ)

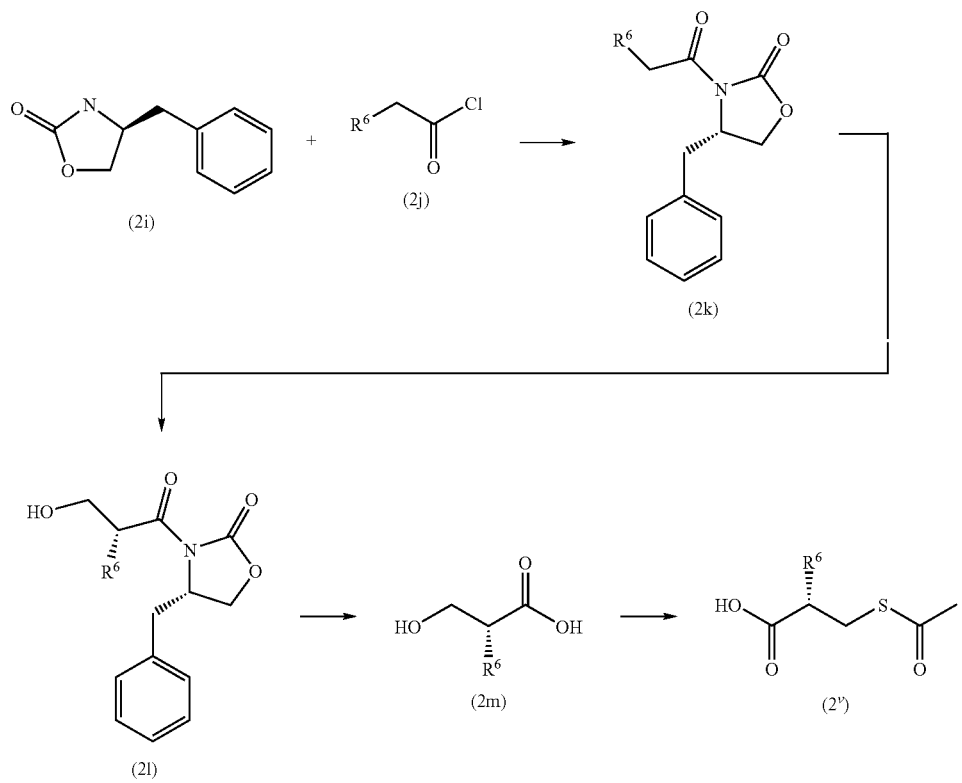

Compound (2i), (S)-4-benzyl-2-oxazolidinone, is typically commercially available. Compound (2j) is also typically commercially available or can be readily synthesized. For example, $R^6$—$CH_2$—COOH (e.g., isocaproic acid or 3-phenylpropionic acid) is dissolved in methylene chloride and thionyl chloride is added. The mixture is stirred at room temperature until the reaction is complete, and then concentrated to provide compound (2j). Examples of compound (2j) include 4-methylpentanoyl chloride and 3-phenylpropionyl chloride.

Compound (2i) is dissolved in a suitable solvent and cooled (−78° C.) under nitrogen. n-Butyllithium in hexane is added dropwise and stirred, followed by the addition of compound (2j) dropwise. The mixture is stirred at −78° C., then warmed to 0° C. Saturated $NaHCO_3$ is added and the mixture warmed to room temperature. The mixture is extracted, washed, dried, filtered and concentrated to afford compound (2k). Compound (2k) is dissolved in DCM and stirred at 0° C. under nitrogen. 1M Titanium tetrachloride is added, followed by 1,3,5-trioxane, all in appropriate solvents. A second equivalent of 1M titanium tetrachloride is added and the mixture stirred at 0° C. until the reaction is complete. The mixture is then quenched with saturated ammonium chloride. Appropriate solvents are added, the aqueous phase is extracted, and the organic layers are combined, dried, filtered and concentrated to provide (2l), which is then purified by silica gel chromatography or used in the next step without further purification. Compound (2l) is dissolved in a solvent, to which is added 9 M hydrogen peroxide in water, followed by the dropwise addition of 1.5 M lithium hydroxide monohydrate in water. The mixture is warmed to room temperature and stirred. Optionally, potassium hydroxide may be added and the mixture heated at 60° C. then cooled at room temperature. To this is added an aqueous solution of sodium sulfite followed by water and chloroform. The aqueous layer is extracted, acidified and extracted again. The organic layer is washed, dried, filtered, and rotovaped to provide (2m). Triphenylphosphine is dissolved in an appropriate solvent and cooled at 0° C. (ice bath). Diisopropyl azodicarboxylate is added dropwise and the mixture stirred. Compound (2m) and thioacetic acid, dissolved in an appropriate solvent, are added dropwise to the mixture. After the addition, the mixture is removed from the ice bath and stirred at room temperature until the reaction is complete (~3.5 hours), concentrated, and then partitioned. The organic layer is extracted and the combined aqueous extracts washed, acidified and extracted. The organic layer is washed again, dried, filtered, and rotovaped to provide compound (2V). Examples of compound (2V) include (S)-2-acetylsulfanylmethyl-4-methylpentanoic acid.

Preparation of Compound (4)

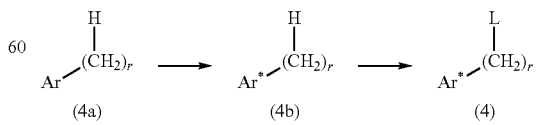

The starting material (4a) can be prepared using synthetic methods that are reported in the literature, for example Duncia et al. (1991) *J. Org. Chem.* 56: 2395-400, and references cited therein. Alternatively, the starting material in protected form (4b) may be commercially available. Using a commercially available non-protected starting material (4a), the $R^1$ group is first protected to form protected intermediate (4b), then the leaving group (L) is added to form compound (4), for example, by a halogenation reaction. For example, a bromination reaction of a methyl group of N-triphenylmethyl-5-[4'-methylbiphenyl-2-yl]tetrazole is described in Chao et al (2005) *J. Chinese Chem. Soc.* 52:539-544. In addition, when Ar* has a —CN group, it can be subsequently converted to the desired tetrazolyl group, which may be protected. Conversion of the nitrile group is readily achieved by reaction with a suitable azide such as sodium azide, trialkyltin azide (particularly tributyltin azide) or triaryltin azide. Compound (4) when Ar has one of the remaining formulas is readily synthesized using similar techniques or other methods as are well known in the art.

Exemplary methods of preparing compound (4) include the following. A solution of the starting material (4a) and thionyl chloride are stirred at room temperature. After completion, the mixture is concentrated in vacuo to afford a solid, which is dissolved in an appropriate solvent and cooled (~0° C.). Potassium t-butoxide is then added. Upon completion, the mixture is partitioned, the organic layer washed, dried, filtered, and concentrated to afford compound (4b). Alternately, HCl is added to a solution of starting material (4a) and a solvent such as methanol. The mixture is heated to reflux, stirred until completion (~48 hours), then cooled and concentrated. The recovered material is dried in vacuo to obtain intermediate (4b). Intermediate (4b), benzoyl peroxide, and N-bromosuccinimide, are dissolved in $CCl_4$ or benzene, and heated to reflux. The mixture is stirred until the reaction is complete, cooled to room temperature, filtered, and concentrated in vacuo. The resulting residue is crystallized from diethyl ether and hexane or flash chromatographed to give compound (4).

Examples of (4a) include 4'-methylbiphenyl-2-carboxylic acid, 2-fluoro-4-methylbenzoic acid, and 2,3-difluoro-4-methyl-benzoic acid. Examples of (4b) include N-triphenylmethyl-5-[4'-methylbiphenyl-2-yl]tetrazole.

Compound (4) where $R^1$ is —$SO_2NHR^{1d}$ may be synthesized as follows:

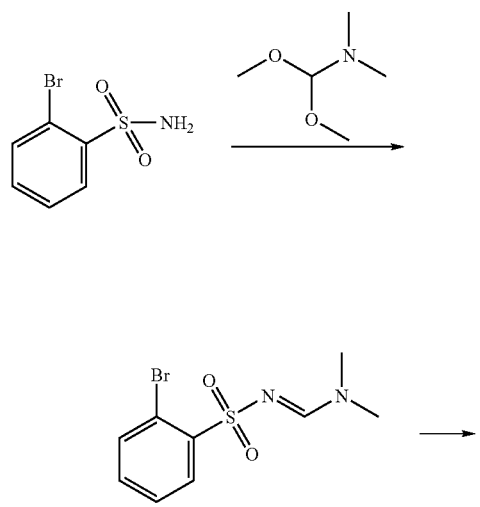

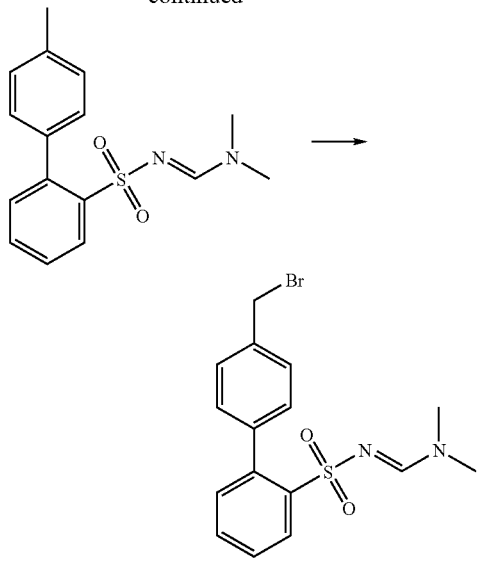

The starting material, 2-bromobenzene-1-sulfonamide, is commercially available. Reaction of 2-bromobenzene-1-sulfonamide in a solvent such as DMF, with 1,1-dimethoxy-N,N-dimethylmethanamine, followed by the addition of sodium hydrogen sulfate in water, yields 2-bromo-N-[1-dimethylaminometh-(E)-ylidene]benzenesulfonamide. This compound is reacted with 4-methylphenylboronic acid to yield 4'-methylbiphenyl-2-sulfonic acid 1-dimethylaminometh-(E)-ylideneamide, then the —$(CH_2)_r$-L moiety is added, for example, by a halogenation reaction, to form compound (4).

Compound (4) where the Ar moiety is substituted may be synthesized as follows:

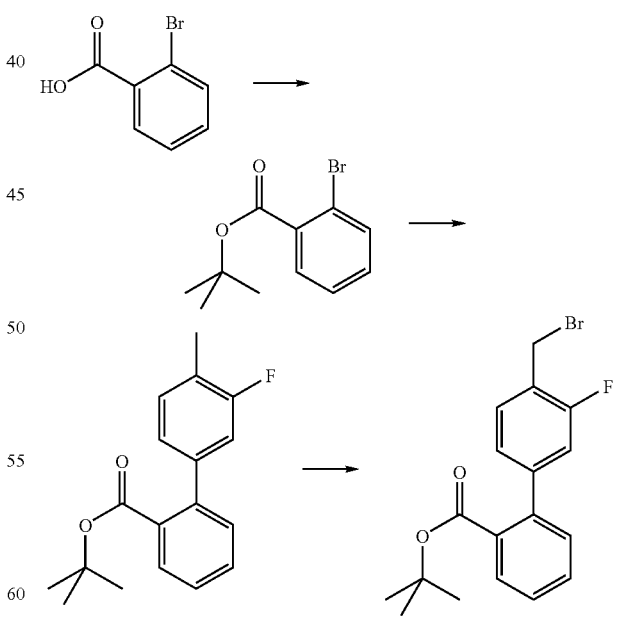

The starting material, 2-bromobenzoic acid, is commercially available. Reaction of 2-bromobenzoic acid in a suitable solvent, with t-butyl alcohol, DCC and DMAP, yields 2-bromobenzoic acid t-butyl ester. This compound is reacted with 3-fluoro-4-methylphenylboronic acid to yield 3'-fluoro-4'- methyl-biphenyl-2-carboxylic acid t-butyl ester, then the —(CH$_2$)$_r$-L moiety is added, for example, by a halogenation reaction, to form compound (4).

Examples of (4) include 4'-bromomethylbiphenyl-2-carboxylic acid t-butyl ester, 4-bromomethyl-2-fluorobenzoic acid methyl ester, 5-(4'-bromomethylbiphenyl-2-yl)-1-trityl-1H-tetrazole, 4-bromomethylbenzoic acid methyl ester; and 4-bromomethyl-2,3-difluorobenzoic acid methyl ester; 4'-formyl-biphenyl-2-sulfonic acid t-butylamide; 4'-aminomethylbiphenyl-2-carboxylic acid t-butyl ester; and 4'-bromomethyl-3'-fluorobiphenyl-2-carboxylic acid t-butyl ester.

If desired, pharmaceutically acceptable salts of the compounds of formula I can be prepared by contacting the free acid or base form of a compound of formula I with a pharmaceutically acceptable base or acid.

Certain intermediates described herein are believed to be novel and accordingly, such compounds are provided as further aspects of the invention including, for example, the compounds of formulas III, IV, and V, and salts thereof:

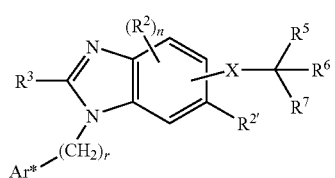
(III)

where Ar* is Ar—R$^{1*}$; Ar, r, n, R$^2$, R$^{2'}$, R$^3$, X, and R$^{5-7}$ are as defined for formula I; and R$^{1*}$ is selected from —C(O)O—P$^2$, —SO$_2$O—P$^5$, —SO$_2$NH—P$^6$, —P(O)(O—P$^7$)$_2$, —OCH(CH$_3$)—C(O)O—P$^2$, —OCH(aryl)-C(O)O—P$^2$, and tetrazol-5-yl-P$^4$; where P$^2$ is a carboxy-protecting group, P$^4$ is a tetrazole-protecting group, P$^5$ is a hydroxyl-protecting group, P$^6$ is a sulfonamide-protecting group, and P$^7$ is a phosphate-protecting group or phosphinate-protecting group;

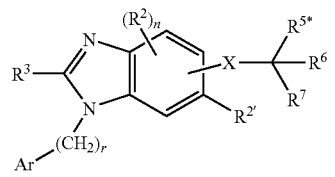
(IV)

where Ar, r, n, R$^2$, R$^{2'}$, R$^3$, X, and R$^{6-7}$ are as defined for formula I; R$^{5*}$ is selected from —C$_{0-3}$alkylene-S—P$^3$, —C$_{0-3}$ alkylene-C(O)NH(O—P$^5$), —C$_{0-3}$alkylene-N(O—P$^5$)—C(O)R$^{5d}$, —C$_{0-1}$alkylene-NHC(O)CH$_2$S—P$^3$, —NH—C$_{0-1}$alkylene-P(O)(O—P$^7$)$_2$, —C$_{0-3}$alkylene-P(O)(O—P$^7$)—R$^{5f}$, —C$_{0-2}$alkylene-CHR$^{5g}$—C(O)O—P$^2$ and —C$_{0-3}$alkylene-C(O)NR$^{5h}$CHR$^{5i}$—C(O)O—P$^2$, and —C$_{0-3}$ alkylene-S—S—P$^3$; and R$^{5d-i}$ are as defined for formula I; where P$^2$ is a carboxy-protecting group, P$^3$ is a thiol-protecting group, P$^5$ is a hydroxyl-protecting group, and P$^7$ is a phosphate-protecting group or phosphinate-protecting group; and

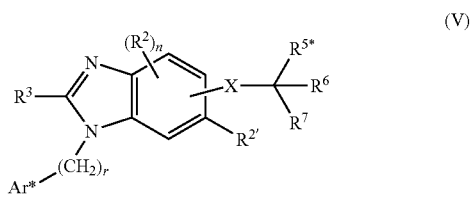
(V)

where Ar* is Ar—R$^{1*}$; Ar, r, n, R$^2$, R$^{2'}$, R$^3$, X, and R$^{6-7}$ are as defined for formula I; R$^{1*}$ is selected from —C(O)O—P$^2$, —SO$_2$O—P$^5$, —SO$_2$NH—P$^6$, —P(O)(O—P$^7$)$_2$, —OCH(CH$_3$)—C(O)O—P$^2$, —OCH(aryl)-C(O)O—P$^2$, and tetrazol-5-yl-P$^4$; R$^{5*}$ is selected from —C$_{0-3}$alkylene-S—P$^3$, —C$_{0-3}$alkylene-C(O)NH(O—P$^5$), —C$_{0-3}$alkylene-N(O—P$^5$)—C(O)R$^{5d}$, —C$_{0-1}$alkylene-NHC(O)CH$_2$S—P$^3$, —NH—C$_{0-1}$ alkylene-P(O)(O—P$^7$)$_2$, —C$_{0-3}$alkylene-P(O)(O—P$^7$)—R$^{5f}$, —C$_{0-2}$alkylene-CHR$^{5g}$—C(O)O—P$^2$ and —C$_{0-3}$alkylene-C(O)NR$^{5h}$CHR$^{5i}$—C(O)O—P$^2$, and —C$_{0-3}$ alkylene-S—S—P$^3$; and R$^{5d-i}$ are as defined for formula I; where P$^2$ is a carboxy-protecting group, P$^3$ is a thiol-protecting group, P$^4$ is a tetrazole-protecting group, P$^5$ is a hydroxyl-protecting group, P$^6$ is a sulfonamide-protecting group, and P$^7$ is a phosphate-protecting group or phosphinate-protecting group. Thus, another method of preparing compounds of the invention involves deprotecting a compound of formula III, IV, or V.

Further details regarding specific reaction conditions and other procedures for preparing representative compounds of the invention or intermediates thereof are described in the Examples set forth below.

Utility

Compounds of the invention possess angiotensin II type 1 (AT$_1$) receptor antagonist activity. In one embodiment, compounds of the invention are selective for inhibition of the AT$_1$ receptor over the AT$_2$ receptor. Compounds of the invention also possess neprilysin (NEP) inhibition activity, i.e., the compounds are able to inhibit enzyme-substrate activity. In another embodiment, the compounds do not exhibit significant inhibitory activity at the angiotensin-converting enzyme. Compounds of formula I may be active drugs as well as prodrugs. Thus, when discussing the activity of compounds of the invention, it is understood that any such prodrugs have the expected AT$_1$ and NEP activity once metabolized.

One measure of the affinity of a compound for the AT$_1$ receptor is the inhibitory constant (K$_i$) for binding to the AT$_1$ receptor. The pK$_i$ value is the negative logarithm to base 10 of the K$_i$. One measure of the ability of a compound to inhibit NEP activity is the inhibitory concentration (IC$_{50}$), which is the concentration of compound that results in half-maximal inhibition of substrate conversion by the NEP enzyme. The pIC$_{50}$ value is the negative logarithm to base 10 of the IC$_{50}$. Compounds of the invention that have both AT$_1$ receptor-antagonizing activity and NEP enzyme-inhibiting activity are of particular interest, including those that exhibit a pK$_i$ at the AT$_1$ receptor greater than or equal to about 5.0, and exhibit a pIC$_{50}$ for NEP greater than or equal to about 5.0.

In one embodiment, compounds of interest have a pK$_i$ at the AT$_1$ receptor≧about 6.0, a pK$_i$ at the AT$_1$ receptor≧about 7.0, or a pK$_i$ at the AT$_1$ receptor≧about 8.0. Compounds of interest also include those having a pIC$_{50}$ for NEP≧about 6.0 or a pIC$_{50}$ for NEP≧about 7.0. In another embodiment, compounds of interest have a $pK_i$ at the $AT_1$ receptor within the range of about 8.0-10.0 and a $pIC_{50}$ for NEP within the range of about 7.0-10.0.

In another embodiment, compounds of particular interest have a $pK_i$ for binding to an $AT_1$ receptor greater than or equal to about 7.5 and a NEP enzyme $pIC_{50}$ greater than or equal to about 7.0. In another embodiment, compounds of interest have a $pK_i$ greater than or equal to about 8.0 and a $pIC_{50}$ greater than or equal to about 8.0.

It is noted that in some cases, compounds of the invention, while still having dual activity, may possess either weak $AT_1$ receptor antagonist activity or weak NEP inhibition activity. In such cases, those of skill in the art will recognize that these compounds still have utility as primarily either a NEP inhibitor or an $AT_1$ receptor antagonist, respectively, or have utility as research tools.

Exemplary assays to determine properties of compounds of the invention, such as the $AT_1$ receptor binding and/or NEP inhibiting activity, are described in the Examples and include by way of illustration and not limitation, assays that measure $AT_1$ and $AT_2$ binding (described in Assay 1), and NEP inhibition (described in Assay 2). Useful secondary assays include assays to measure ACE inhibition (also described in Assay 2) and aminopeptidase P (APP) inhibition (described in Sulpizio et al. (2005) *JPET* 315:1306-1313). A pharmacodynamic assay to assess the in vivo inhibitory potencies for ACE, $AT_1$, and NEP in anesthetized rats is described in Assay 3 (see also Seymour et al. *Hypertension* 7(Suppl I):I-35-I-42, 1985 and Wigle et al. *Can. J. Physiol. Pharmacol.* 70:1525-1528, 1992), where $AT_1$ inhibition is measured as the percent inhibition of the angiotensin II pressor response, ACE inhibition is measured as the percent inhibition of the angiotensin I pressor response, and NEP inhibition is measured as increased urinary cyclic guanosine 3', 5'-monophosphate (cGMP) output. Useful in vivo assays include the conscious spontaneously hypertensive rat (SHR) model, which is a renin dependent hypertension model that is useful for measuring $AT_1$ receptor blocking (described in Assay 4; see also Intengan et al. (1999) *Circulation* 100(22):2267-2275 and Badyal et al. (2003) *Indian Journal of Pharmacology* 35:349-362), and the conscious desoxycorticosterone acetate-salt (DOCA-salt) rat model, which is a volume dependent hypertension model that is useful for measuring NEP activity (described in Assay 5; see also Trapani et al. (1989) *J. Cardiovasc. Pharmacol.* 14:419-424, Intengan et al. (1999) *Hypertension* 34(4):907-913, and Badyal et al. (2003) supra). Both the SHR and DOCA-salt models are useful for evaluating the ability of a test compound to reduce blood pressure. The DOCA-salt model is also useful to measure a test compound's ability to prevent or delay a rise in blood pressure. Compounds of the invention are expected to antagonize the $AT_1$ receptor and/or inhibit the NEP enzyme in any of the assays described herein, or assays of a similar nature. Thus, the aforementioned assays are useful in determining the therapeutic utility of compounds of the invention, for example, their utility as antihypertensive agents. Other properties and utilities of compounds of the invention can be demonstrated using various in vitro and in vivo assays well-known to those skilled in the art.

Compounds of the invention are expected to be useful for the treatment and/or prevention of medical conditions responsive to $AT_1$ receptor antagonism and/or NEP inhibition. Thus it is expected that patients suffering from a disease or disorder that is treated by antagonizing the $AT_1$ receptor and/or by inhibiting the NEP enzyme can be treated by administering a therapeutically effective amount of a compound of the invention. For example, by antagonizing the $AT_1$ receptor and thus interfering with the action of angiotensin II on its receptors, these compounds are expected to find utility in preventing the increase in blood pressure produced by angiotensin II, a potent vasopressor. In addition, by inhibiting NEP, the compounds are also expected to potentiate the biological effects of endogenous peptides that are metabolized by NEP, such as the natriuretic peptides, bombesin, bradykinins, calcitonin, endothelins, enkephalins, neurotensin, substance P and vasoactive intestinal peptide. For example, by potentiating the effects of the natriuretic peptides, compounds of the invention are expected to be useful to treat glaucoma. These compounds are also expected to have other physiological actions, for example, on the renal, central nervous, reproductive and gastrointestinal systems.

Compounds of the invention are expected to find utility in treating and/or preventing medical conditions such as cardiovascular and renal diseases. Cardiovascular diseases of particular interest include heart failure such as congestive heart failure, acute heart failure, chronic heart failure, and acute and chronic decompensated heart failure. Renal diseases of particular interest include diabetic nephropathy and chronic kidney disease. One embodiment of the invention relates to a method for treating hypertension, comprising administering to a patient a therapeutically effective amount of a compound of the invention. Typically, the therapeutically effective amount is the amount that is sufficient to lower the patient's blood pressure. In one embodiment, the compound is administered as an oral dosage form.

Another embodiment of the invention relates to a method for treating heart failure, comprising administering to a patient a therapeutically effective amount of a compound of the invention. Typically, the therapeutically effective amount is the amount that is sufficient to lower blood pressure and/or improve renal functions. In one embodiment, the compound is administered as an intravenous dosage form. When used to treat heart failure, the compound may be administered in combination with other therapeutic agents such as diuretics, natriuretic peptides, and adenosine receptors antagonist.

Compounds of the invention are also expected to be useful in preventative therapy, for example in preventing the progression of cardiac insufficiency after myocardial infarction, preventing arterial restenosis after angioplasty, preventing thickening of blood vessel walls after vascular operations, preventing atherosclerosis, and preventing diabetic angiopathy.

In addition, as NEP inhibitors, compounds of the invention are expected to inhibit enkephalinase, which will inhibit the degradation of endogenous enkephalins. Thus, such compounds may also find utility as analgesics. Due to their NEP inhibition properties, compounds of the invention are also expected to be useful as antitussive agents and antidiarrheal agents (for example, for the treatment of watery diarrhea), as well as find utility in the treatment of menstrual disorders, preterm labor, pre-eclampsia, endometriosis, reproductive disorders (e.g., male and female infertility, polycystic ovarian syndrome, implantation failure), and male and female sexual dysfunction, including male erectile dysfunction and female sexual arousal disorder. More specifically, the compounds of the invention are expected to be useful in treating female sexual dysfunction, which is often defined as a female patient's difficulty or inability to find satisfaction in sexual expression. This covers a variety of diverse female sexual disorders including, by way of illustration and not limitation, hypoactive sexual desire disorder, sexual arousal disorder, orgasmic disorders and sexual pain disorders. When used to treat such disorders, especially female sexual dysfunction, the compounds of the invention may be combined with one or more of the following secondary agents: PDE5 inhibitors, dopamine agonists, estrogen receptor agonists and/or antagonists, androgens, and estrogens.

The amount of the compound of the invention administered per dose or the total amount administered per day may be predetermined or it may be determined on an individual patient basis by taking into consideration numerous factors, including the nature and severity of the patient's condition, the condition being treated, the age, weight, and general health of the patient, the tolerance of the patient to the active agent, the route of administration, pharmacological considerations such as the activity, efficacy, pharmacokinetics and toxicology profiles of the compound and any secondary agents being administered, and the like. Treatment of a patient suffering from a disease or medical condition (such as hypertension) can begin with a predetermined dosage or a dosage determined by the treating physician, and will continue for a period of time necessary to prevent, ameliorate, suppress, or alleviate the symptoms of the disease or medical condition. Patients undergoing such treatment will typically be monitored on a routine basis to determine the effectiveness of therapy. For example, in treating hypertension, blood pressure measurements may be used to determine the effectiveness of treatment. Similar indicators for other diseases and conditions described herein, are well-known and are readily available to the treating physician. Continuous monitoring by the physician will insure that the optimal amount of the compound of the invention will be administered at any given time, as well as facilitating the determination of the duration of treatment. This is of particular value when secondary agents are also being administered, as their selection, dosage, and duration of therapy may also require adjustment. In this way, the treatment regimen and dosing schedule can be adjusted over the course of therapy so that the lowest amount of active agent that exhibits the desired effectiveness is administered and, further, that administration is continued only so long as is necessary to successfully treat the disease or medical condition.

Since compounds of the invention possess $AT_1$ receptor antagonist activity and/or NEP enzyme inhibition activity, such compounds are also useful as research tools for investigating or studying biological systems or samples having $AT_1$ receptors or a NEP enzyme, for example to study diseases where the $AT_1$ receptor or NEP enzyme plays a role. Any suitable biological system or sample having $AT_1$ receptors and/or a NEP enzyme may be employed in such studies which may be conducted either in vitro or in vivo. Representative biological systems or samples suitable for such studies include, but are not limited to, cells, cellular extracts, plasma membranes, tissue samples, isolated organs, mammals (such as mice, rats, guinea pigs, rabbits, dogs, pigs, humans, and so forth), and the like, with mammals being of particular interest. In one particular embodiment of the invention an $AT_1$ receptor in a mammal is antagonized by administering an $AT_1$-antagonizing amount of a compound of the invention. In another particular embodiment, NEP enzyme activity in a mammal is inhibited by administering a NEP-inhibiting amount of a compound of the invention. Compounds of the invention can also be used as research tools by conducting biological assays using such compounds.

When used as a research tool, a biological system or sample comprising an $AT_1$ receptor and/or a NEP enzyme is typically contacted with an $AT_1$ receptor-antagonizing or NEP enzyme-inhibiting amount of a compound of the invention. After the biological system or sample is exposed to the compound, the effects of antagonizing the $AT_1$ receptor and/or inhibiting the NEP enzyme are determined using conventional procedures and equipment, such as by measuring receptor binding in a binding assay or measuring ligand-mediated changes in a functional assay. Exposure encompasses contacting cells or tissue with the compound, administering the compound to a mammal, for example by i.p., i.v. or s.c. administration, and so forth. This determining step can involve measuring a response (a quantitative analysis) or can involve making an observation (a qualitative analysis). Measuring a response involves, for example, determining the effects of the compound on the biological system or sample using conventional procedures and equipment, such as radioligand binding assays and measuring ligand-mediated changes in functional assays. The assay results can be used to determine the activity level as well as the amount of compound necessary to achieve the desired result, i.e., an $AT_1$ receptor-antagonizing and/or a NEP enzyme-inhibiting amount. Typically, the determining step will involve determining the $AT_1$ receptor ligand-mediated effects and/or determining the effects of inhibiting the NEP enzyme.

Additionally, compounds of the invention can be used as research tools for evaluating other chemical compounds, and thus are also useful in screening assays to discover, for example, new compounds having $AT_1$ receptor-antagonizing activity and/or NEP-inhibiting activity. In this manner, a compound of the invention is used as a standard in an assay to allow comparison of the results obtained with a test compound and with compounds of the invention to identify those test compounds that have about equal or superior activity, if any. For example, $K_i$ data (as determined, for example, by a binding assay) for a test compound or a group of test compounds is compared to the $K_i$ data for a compound of the invention to identify those test compounds that have the desired properties, e.g., test compounds having a $K_i$ value about equal or superior to a compound of the invention, if any. This aspect of the invention includes, as separate embodiments, both the generation of comparison data (using the appropriate assays) and the analysis of the test data to identify test compounds of interest. Thus, a test compound can be evaluated in a biological assay, by a method comprising the steps of: (a) conducting a biological assay with a test compound to provide a first assay value; (b) conducting the biological assay with a compound of the invention to provide a second assay value; wherein step (a) is conducted either before, after or concurrently with step (b); and (c) comparing the first assay value from step (a) with the second assay value from step (b). Exemplary biological assays include an $AT_1$ receptor binding assay and a NEP enzyme inhibition assay.

Pharmaceutical Compositions and Formulations

Compounds of the invention are typically administered to a patient in the form of a pharmaceutical composition or formulation. Such pharmaceutical compositions may be administered to the patient by any acceptable route of administration including, but not limited to, oral, rectal, vaginal, nasal, inhaled, topical (including transdermal), ocular, and parenteral modes of administration. Further, the compounds of the invention may be administered, for example orally, in multiple doses per day (e.g., two, three, or four times daily), in a single daily dose or a single weekly dose. It will be understood that any form of the compounds of the invention, (i.e., free base, free acid, pharmaceutically acceptable salt, solvate, etc.) that is suitable for the particular mode of administration can be used in the pharmaceutical compositions discussed herein.

Accordingly, in one embodiment, the invention relates to a pharmaceutical composition comprising a pharmaceutically acceptable carrier and a compound of the invention. The compositions may contain other therapeutic and/or formulating agents if desired. When discussing compositions, the "compound of the invention" may also be referred to herein as the "active agent," to distinguish it from other components of the formulation, such as the carrier. Thus, it is understood that the term "active agent" includes compounds of formula I as well as pharmaceutically acceptable salts, solvates and prodrugs of that compound.

The pharmaceutical compositions of the invention typically contain a therapeutically effective amount of a compound of the invention. Those skilled in the art will recognize, however, that a pharmaceutical composition may contain more than a therapeutically effective amount such as in bulk compositions, or less than a therapeutically effective amount such as in individual unit doses designed for multiple administration to achieve a therapeutically effective amount. Typically, the composition will contain from about 0.01-95 wt % of active agent, including, from about 0.01-30 wt %, such as from about 0.01-10 wt %, with the actual amount depending upon the formulation itself, the route of administration, the frequency of dosing, and so forth. In one embodiment, a composition suitable for an oral dosage form, for example, may contain about 5-70 wt %, or from about 10-60 wt % of active agent.

Any conventional carrier or excipient may be used in the pharmaceutical compositions of the invention. The choice of a particular carrier or excipient, or combinations of carriers or excipients, will depend on the mode of administration being used to treat a particular patient or type of medical condition or disease state. In this regard, the preparation of a suitable composition for a particular mode of administration is well within the scope of those skilled in the pharmaceutical arts. Additionally, carriers or excipients used in such compositions are commercially available. By way of further illustration, conventional formulation techniques are described in *Remington: The Science and Practice of Pharmacy*, 20$^{th}$ Edition, Lippincott Williams & White, Baltimore, Md. (2000); and H. C. Ansel et al., *Pharmaceutical Dosage Forms and Drug Delivery Systems*, 7$^{th}$ Edition, Lippincott Williams & White, Baltimore, Md. (1999).

Representative examples of materials which can serve as pharmaceutically acceptable carriers include, but are not limited to, the following: sugars, such as lactose, glucose and sucrose; starches, such as corn starch and potato starch; cellulose, such as microcrystalline cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; compressed propellant gases, such as chlorofluorocarbons and hydrofluorocarbons; and other non-toxic compatible substances employed in pharmaceutical compositions.

Pharmaceutical compositions are typically prepared by thoroughly and intimately mixing or blending the active agent with a pharmaceutically acceptable carrier and one or more optional ingredients. The resulting uniformly blended mixture may then be shaped or loaded into tablets, capsules, pills, canisters, cartridges, dispensers and the like using conventional procedures and equipment.

In those formulations where the compound of the invention contains a thiol group, additional consideration may be given to minimize or eliminate oxidation of the thiol to form a disulfide. In solid formulations, this may be accomplished by reducing the drying time, decreasing the moisture content of the formulation, and including materials such as ascorbic acid, sodium ascorbate, sodium sulfite and sodium bisulfite, as well as materials such as a mixture of lactose and microcrystalline cellulose. In liquid formulations, stability of the thiol may be improved by the addition of amino acids, antioxidants, or a combination of disodium edetate and ascorbic acid.

In one embodiment, the pharmaceutical compositions are suitable for oral administration. Suitable compositions for oral administration may be in the form of capsules, tablets, pills, lozenges, cachets, dragees, powders, granules; solutions or suspensions in an aqueous or non-aqueous liquid; oil-in-water or water-in-oil liquid emulsions; elixirs or syrups; and the like; each containing a predetermined amount of the active agent.

When intended for oral administration in a solid dosage form (i.e., as capsules, tablets, pills and the like), the composition will typically comprise the active agent and one or more pharmaceutically acceptable carriers, such as sodium citrate or dicalcium phosphate. Solid dosage forms may also comprise: fillers or extenders, such as starches, microcrystalline cellulose, lactose, sucrose, glucose, mannitol, and/or silicic acid; binders, such as carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and/or sodium carbonate; solution retarding agents, such as paraffin; absorption accelerators, such as quaternary ammonium compounds; wetting agents, such as cetyl alcohol and/or glycerol monostearate; absorbents, such as kaolin and/or bentonite clay; lubricants, such as talc, calcium stearate, magnesium stearate, solid polyethylene glycols, sodium lauryl sulfate, and/or mixtures thereof, coloring agents; and buffering agents.

Release agents, wetting agents, coating agents, sweetening, flavoring and perfuming agents, preservatives and antioxidants may also be present in the pharmaceutical compositions. Exemplary coating agents for tablets, capsules, pills and like, include those used for enteric coatings, such as cellulose acetate phthalate, polyvinyl acetate phthalate, hydroxypropyl methylcellulose phthalate, methacrylic acid-methacrylic acid ester copolymers, cellulose acetate trimellitate, carboxymethyl ethyl cellulose, hydroxypropyl methyl cellulose acetate succinate, and the like. Examples of pharmaceutically acceptable antioxidants include: water-soluble antioxidants, such as ascorbic acid, cysteine hydrochloride, sodium bisulfate, sodium metabisulfate sodium sulfite and the like; oil-soluble antioxidants, such as ascorbyl palmitate, butylated hydroxyanisole, butylated hydroxytoluene, lecithin, propyl gallate, alpha-tocopherol, and the like; and metal-chelating agents, such as citric acid, ethylenediamine tetraacetic acid, sorbitol, tartaric acid, phosphoric acid, and the like.

Compositions may also be formulated to provide slow or controlled release of the active agent using, by way of example, hydroxypropyl methyl cellulose in varying proportions or other polymer matrices, liposomes and/or microspheres. In addition, the pharmaceutical compositions of the invention may contain opacifying agents and may be formulated so that they release the active agent only, or preferentially, in a certain portion of the gastrointestinal tract, optionally, in a delayed manner. Examples of embedding compositions which can be used include polymeric substances and waxes. The active agent can also be in microencapsulated form, if appropriate, with one or more of the above-described excipients.

Suitable liquid dosage forms for oral administration include, by way of illustration, pharmaceutically acceptable emulsions, microemulsions, solutions, suspensions, syrups and elixirs. Liquid dosage forms typically comprise the active agent and an inert diluent, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (e.g., cottonseed, groundnut, corn, germ, olive, castor and sesame oils), glycerol, tetrahydrofuryl alcohol, polyethylene glycols and fatty acid esters of sorbitan, and mixtures thereof. Suspensions may contain suspending agents such as, for example, ethoxylated isostearyl alcohols, polyoxyethylene sorbitol and sorbitan esters, microcrystalline cellulose, aluminium metahydroxide, bentonite, agar-agar and tragacanth, and mixtures thereof.

When intended for oral administration, the pharmaceutical compositions of the invention may be packaged in a unit dosage form. The term "unit dosage form" refers to a physically discrete unit suitable for dosing a patient, i.e., each unit containing a predetermined quantity of the active agent calculated to produce the desired therapeutic effect either alone or in combination with one or more additional units. For example, such unit dosage forms may be capsules, tablets, pills, and the like.

In another embodiment, the compositions of the invention are suitable for inhaled administration, and will typically be in the form of an aerosol or a powder. Such compositions are generally administered using well-known delivery devices, such as a nebulizer, dry powder, or metered-dose inhaler. Nebulizer devices produce a stream of high velocity air that causes the composition to spray as a mist that is carried into a patient's respiratory tract. An exemplary nebulizer formulation comprises the active agent dissolved in a carrier to form a solution, or micronized and combined with a carrier to form a suspension of micronized particles of respirable size. Dry powder inhalers administer the active agent as a free-flowing powder that is dispersed in a patient's air-stream during inspiration. An exemplary dry powder formulation comprises the active agent dry-blended with an excipient such as lactose, starch, mannitol, dextrose, polylactic acid, polylactide-co-glycolide, and combinations thereof. Metered-dose inhalers discharge a measured amount of the active agent using compressed propellant gas. An exemplary metered-dose formulation comprises a solution or suspension of the active agent in a liquefied propellant, such as a chlorofluorocarbon or hydrofluoroalkane. Optional components of such formulations include co-solvents, such as ethanol or pentane, and surfactants, such as sorbitan trioleate, oleic acid, lecithin, glycerin, and sodium lauryl sulfate. Such compositions are typically prepared by adding chilled or pressurized hydrofluoroalkane to a suitable container containing the active agent, ethanol (if present) and the surfactant (if present). To prepare a suspension, the active agent is micronized and then combined with the propellant. Alternatively, a suspension formulation can be prepared by spray drying a coating of surfactant on micronized particles of the active agent. The formulation is then loaded into an aerosol canister, which forms a portion of the inhaler.

Compounds of the invention can also be administered parenterally (e.g., by subcutaneous, intravenous, intramuscular, or intraperitoneal injection). For such administration, the active agent is provided in a sterile solution, suspension, or emulsion. Exemplary solvents for preparing such formulations include water, saline, low molecular weight alcohols such as propylene glycol, polyethylene glycol, oils, gelatin, fatty acid esters such as ethyl oleate, and the like. Parenteral formulations may also contain one or more anti-oxidants, solubilizers, stabilizers, preservatives, wetting agents, emulsifiers, and dispersing agents. Surfactants, additional stabilizing agents or pH-adjusting agents (acids, bases or buffers) and anti-oxidants are particularly useful to provide stability to the formulation, for example, to minimize or avoid hydrolysis of ester and amide linkages, or dimerization of thiols that may be present in the compound. These formulations may be rendered sterile by use of a sterile injectable medium, a sterilizing agent, filtration, irradiation, or heat. In one particular embodiment, the parenteral formulation comprises an aqueous cyclodextrin solution as the pharmaceutically acceptable carrier. Suitable cyclodextrins include cyclic molecules containing six or more α-D-glucopyranose units linked at the 1,4 positions by a linkages as in amylase, β-cyclodextrin or cycloheptaamylose. Exemplary cyclodextrins include cyclodextrin derivatives such as hydroxypropyl and sulfobutyl ether cyclodextrins such as hydroxypropyl-β-cyclodextrin and sulfobutyl ether β-cyclodextrin. Exemplary buffers for such formulations include carboxylic acid-based buffers such as citrate, lactate and maleate buffer solutions.

Compounds of the invention can also be administered transdermally using known transdermal delivery systems and excipients. For example, the compound can be admixed with permeation enhancers, such as propylene glycol, polyethylene glycol monolaurate, azacycloalkan-2-ones and the like, and incorporated into a patch or similar delivery system. Additional excipients including gelling agents, emulsifiers and buffers, may be used in such transdermal compositions if desired.

If desired, the compounds of the invention may be administered in combination with one or more other therapeutic agents. Thus, in one embodiment, pharmaceutical compositions of the invention contain other drugs that are co-administered with a compound of the invention. For example, the composition may further comprise one or more drugs (also referred to as "secondary agents(s)") selected from the group of diuretics, $\beta_1$ adrenergic receptor blockers, calcium channel blockers, angiotensin-converting enzyme inhibitors, $AT_1$ receptor antagonists, neprilysin inhibitors, non-steroidal anti-inflammatory agents, prostaglandins, anti-lipid agents, anti-diabetic agents, anti-thrombotic agents, renin inhibitors, endothelin receptor antagonists, endothelin converting enzyme inhibitors, aldosterone antagonists, angiotensin-converting enzyme/neprilysin inhibitors, and combinations thereof. Such therapeutic agents are well known in the art, and specific examples are described herein. By combining a compound of the invention with a secondary agent, triple therapy can be achieved, i.e., $AT_1$ receptor antagonist activity, NEP inhibition activity and activity associated with the secondary agent (e.g., $\beta_1$ adrenergic receptor blocker), using only two active components. Since compositions containing two active components are typically easier to formulate than compositions containing three active components, such two-component compositions provide a significant advantage over compositions containing three active components. Accordingly, in yet another aspect of the invention, a pharmaceutical composition comprises a compound of the invention, a second active agent, and a pharmaceutically acceptable carrier. Third, fourth, etc., active agents may also be included in the composition. In combination therapy, the amount of compound of the invention that is administered, as well as the amount of secondary agents, may be less than the amount typically administered in monotherapy.

Compounds of the invention may be physically mixed with the second active agent to form a composition containing both agents; or each agent may be present in separate and distinct compositions which are administered to the patient simultaneously or at separate times. For example, a compound of the invention can be combined with a second active agent using conventional procedures and equipment to form a combination of active agents comprising a compound of the invention and a second active agent. Additionally, the active agents may be combined with a pharmaceutically acceptable carrier to form a pharmaceutical composition comprising a compound of the invention, a second active agent and a pharmaceutically acceptable carrier. In this embodiment, the components of the composition are typically mixed or blended to create a physical mixture. The physical mixture is then administered in a therapeutically effective amount using any of the routes described herein.

Alternatively, the active agents may remain separate and distinct before administration to the patient. In this embodiment, the agents are not physically mixed together before administration but are administered simultaneously or at separate times as separate compositions. Such compositions can be packaged separately or may be packaged together in a kit. When administered at separate times, the secondary agent will typically be administered less than 24 hours after administration of the compound of the invention, ranging anywhere from concurrent with administration of the compound of the invention to about 24 hours post-dose. This is also referred to as sequential administration. Thus, a compound of the invention can be orally administered simultaneously or sequentially with another active agent using two tablets, with one tablet for each active agent, where sequential may mean being administered immediately after administration of the compound of the invention or at some predetermined time later (e.g., one hour later or three hours later). Alternatively, the combination may be administered by different routes of administration, i.e., one orally and the other by inhalation.

In one embodiment, the kit comprises a first dosage form comprising a compound of the invention and at least one additional dosage form comprising one or more of the secondary agents set forth herein, in quantities sufficient to carry out the methods of the invention. The first dosage form and the second (or third, etc,) dosage form together comprise a therapeutically effective amount of active agents for the treatment or prevention of a disease or medical condition in a patient.

Secondary agent(s), when included, are present in a therapeutically effective amount such that they produce a therapeutically beneficial effect when co-administered with a compound of the invention. The secondary agent can be in the form of a pharmaceutically acceptable salt, solvate, optically pure stereoisomer, and so forth. The secondary agent may also be in the form of a prodrug, for example, a compound having a carboxylic acid group that has been esterified. Thus, secondary agents listed herein are intended to include all such forms, and are commercially available or can be prepared using conventional procedures and reagents.

In one embodiment, a compound of the invention is administered in combination with a diuretic. Representative diuretics include, but are not limited to: carbonic anhydrase inhibitors such as acetazolamide and dichlorphenamide; loop diuretics, which include sulfonamide derivatives such as acetazolamide, ambuside, azosemide, bumetanide, butazolamide, chloraminophenamide, clofenamide, clopamide, clorexolone, disulfamide, ethoxolamide, furosemide, mefruside, methazolamide, piretanide, torsemide, tripamide, and xipamide, as well as non-sulfonamide diuretics such as ethacrynic acid and other phenoxyacetic acid compounds such as tienilic acid, indacrinone and quincarbate; osmotic diuretics such as mannitol; potassium-sparing diuretics, which include aldosterone antagonists such as spironolactone, and $Na^+$ channel inhibitors such as amiloride and triamterene; thiazide and thiazide-like diuretics such as althiazide, bendroflumethiazide, benzylhydrochlorothiazide, benzthiazide, buthiazide, chlorthalidone, chlorothiazide, cyclopenthiazide, cyclothiazide, epithiazide, ethiazide, fenquizone, flumethiazide, hydrochlorothiazide, hydroflumethiazide, indapamide, methylclothiazide, meticrane, metolazone, paraflutizide, polythiazide, quinethazone, teclothiazide, and trichloromethiazide; and combinations thereof. In a particular embodiment, the diuretic is selected from amiloride, bumetanide, chlorothiazide, chlorthalidone, dichlorphenamide, ethacrynic acid, furosemide, hydrochlorothiazide, hydroflumethiazide, indapamide, methylclothiazide, metolazone, torsemide, triamterene, and combinations thereof. The diuretic will be administered in an amount sufficient to provide from about 5-50 mg per day, more typically 6-25 mg per day, with common dosages being 6.25 mg, 12.5 mg or 25 mg per day.

Compounds of the invention may also be administered in combination with a $\beta_1$ adrenergic receptor blocker. Representative $\beta_1$ adrenergic receptor blockers include, but are not limited to, acebutolol, alprenolol, amosulalol, arotinolol, atenolol, befunolol, betaxolol, bevantolol, bisoprolol, bopindolol, bucindolol, bucumolol, bufetolol, bufuralol, bunitrolol, bupranolol, bubridine, butofilolol, carazolol, carteolol, carvedilol, celiprolol, cetamolol, cloranolol, dilevalol, epanolol, esmolol, indenolol, labetolol, levobunolol, mepindolol, metipranolol, metoprolol such as metoprolol succinate and metoprolol tartrate, moprolol, nadolol, nadoxolol, nebivalol, nipradilol, oxprenolol, penbutolol, perbutolol, pindolol, practolol, pronethalol, propranolol, sotalol, sufinalol, talindol, tertatolol, tilisolol, timolol, toliprolol, xibenolol, and combinations thereof. In one particular embodiment, the $\beta_1$ adrenergic receptor blocker is selected from atenolol, bisoprolol, metoprolol, propranolol, sotalol, and combinations thereof.

In one embodiment, a compound of the invention is administered in combination with a calcium channel blocker. Representative calcium channel blockers include, but are not limited to, amlodipine, anipamil, aranipine, barnidipine, bencyclane, benidipine, bepridil, clentiazem, cilnidipine, cinnarizine, diltiazem, efonidipine, elgodipine, etafenone, felodipine, fendiline, flunarizine, gallopamil, isradipine, lacidipine, lercanidipine, lidoflazine, lomerizine, manidipine, mibefradil, nicardipine, nifedipine, niguldipine, niludipine, nilvadipine, nimodipine, nisoldipine, nitrendipine, nivaldipine, perhexyline, prenylamine, ryosidine, semotiadil, terodiline, tiapamil, verapamil, and combinations thereof. In a particular embodiment, the calcium channel blocker is selected from amlodipine, bepridil, diltiazem, felodipine, isradipine, lacidipine, nicardipine, nifedipine, niguldipine, niludipine, nimodipine, nisoldipine, ryosidine, verapamil, and combinations thereof.

Compounds of the invention can also be administered in combination with an angiotensin-converting enzyme (ACE) inhibitor. Representative ACE inhibitors include, but are not limited to, accupril, alacepril, benazepril, benazeprilat, captopril, ceranapril, cilazapril, delapril, enalapril, enalaprilat, fosinopril, fosinoprilat, imidapril, lisinopril, moexipril, monopril, moveltopril, pentopril, perindopril, quinapril, quinaprilat, ramipril, ramiprilat, saralasin acetate, spirapril, temocapril, trandolapril, zofenopril, and combinations thereof. In a particular embodiment, the ACE inhibitor is selected from: benazepril, enalapril, lisinopril, ramipril, and combinations thereof.

In one embodiment, a compound of the invention is administered in combination with an $AT_1$ receptor antagonist, also known as angiotensin II type 1 receptor blockers (ARBs). Representative ARBs include, but are not limited to, abitesartan, benzyllosartan, candesartan, candesartan cilexetil, elisartan, embusartan, enoltasosartan, eprosartan, fonsartan, forasartan, glycyllosartan, irbesartan, isoteoline, losartan, medoximil, milfasartan, olmesartan, opomisartan, pratosartan, ripisartan, saprisartan, saralasin, sarmesin, tasosartan, telmisartan, valsartan, zolasartan, and combinations thereof. In a particular embodiment, the ARB is selected from candesartan, eprosartan, irbesartan, losartan, olmesartan, saprisartan, tasosartan, telmisartan, valsartan, and combinations thereof. Exemplary salts include eprosartan mesylate, losartan potassium salt, and olmesartan medoxomil. Typically, the ARB will be administered in an amount sufficient to provide from about 4-600 mg per dose, with exemplary daily dosages ranging from 20-320 mg per day.

In another embodiment, a compound of the invention is administered in combination with a neprilysin (NEP) inhibitor. Representative NEP inhibitors include, but are not limited to: candoxatril; candoxatrilat; dexecadotril ((+)-N-[2(R)-(acetylthiomethyl)-3-phenylpropionyl]glycine benzyl ester); CGS-24128 (3-[3-(biphenyl-4-yl)-2-(phosphonomethylamino)propionamido]propionic acid); CGS-24592 ((S)-3-[3-(biphenyl-4-yl)-2-(phosphonomethylamino)propionamido]propionic acid); CGS-25155 (N-[9(R)-(acetylthiomethyl)-10-oxo-1-azacyclodecan-2 (S)-ylcarbonyl]-4(R)-hydroxy-L-proline benzyl ester); 3-(1-carbamoylcyclohexyl)propionic acid derivatives described in WO 2006/027680 to Hepworth et al. (Pfizer Inc.); JMV-390-1 (2(R)-benzyl-3-(N-hydroxycarbamoyl)propionyl-L-isoleucyl-L-leucine); ecadotril; phosphoramidon; retrothiorphan; RU-42827 (2-(mercaptomethyl)-N-(4-pyridinyl)benzenepropionamide); RU-44004 (N-(4-morpholinyl)-3-phenyl-2-(sulfanylmethyl)propionamide); SCH-32615 ((S)—N—[N-(1-carboxy-2-phenylethyl)-L-phenylalanyl]-β-alanine) and its prodrug SCH-34826 ((S)—N—[N-[1-[[(2,2-dimethyl-1,3-dioxolan-4-yl)methoxy]carbonyl]-2-phenylethyl]-L-phenylalanyl]-β-alanine); sialorphin; SCH-42495 (N-[2(S)-(acetylsulfanylmethyl)-3-(2-methylphenyl)propionyl]-L-methionine ethyl ester); spinorphin; SQ-28132 (N-[2-(mercaptomethyl)-1-oxo-3-phenylpropyl]leucine); SQ-28603 (N-[2-(mercaptomethyl)-1-oxo-3-phenylpropyl]-β-alanine); SQ-29072 (7-[[2-(mercaptomethyl)-1-oxo-3-phenylpropyl]amino]heptanoic acid); thiorphan and its prodrug racecadotril; UK-69578 (cis-4-[[[1-[2-carboxy-3-(2-methoxyethoxy)propyl]cyclopentyl]carbonyl]amino]cyclohexanecarboxylic acid); UK-447,841 (2-{1-[3-(4-chlorophenyl)propylcarbamoyl]-cyclopentylmethyl}-4-methoxybutyric acid); UK-505,749 ((R)-2-methyl-3-{1-[3-(2-methylbenzothiazol-6-yl)propylcarbamoyl]cyclopentyl}propionic acid); 5-biphenyl-4-yl-4-(3-carboxypropionylamino)-2-methylpentanoic acid and 5-biphenyl-4-yl-4-(3-carboxypropionylamino)-2-methylpentanoic acid ethyl ester (WO 2007/056546); and combinations thereof. In a particular embodiment, the NEP inhibitor is selected from candoxatril, candoxatrilat, CGS-24128, phosphoramidon, SCH-32615, SCH-34826, SQ-28603, thiorphan, and combinations thereof. The NEP inhibitor will be administered in an amount sufficient to provide from about 20-800 mg per day, with typical daily dosages ranging from 50-700 mg per day, more commonly 100-600 or 100-300 mg per day.

In yet another embodiment, a compound of the invention is administered in combination with a non-steroidal anti-inflammatory agent (NSAID). Representative NSAIDs include, but are not limited to: acemetacin, acetyl salicylic acid, alclofenac, alminoprofen, amfenac, amiprilose, amoxiprin, anirolac, apazone, azapropazone, benorilate, benoxaprofen, bezpiperylon, broperamole, bucloxic acid, carprofen, clidanac, diclofenac, diflunisal, diftalone, enolicam, etodolac, etoricoxib, fenbufen, fenclofenac, fenclozic acid, fenoprofen, fentiazac, feprazone, flufenamic acid, flufenisal, fluprofen, flurbiprofen, furofenac, ibufenac, ibuprofen, indomethacin, indoprofen, isoxepac, isoxicam, ketoprofen, ketorolac, lofemizole, lornoxicam, meclofenamate, meclofenamic acid, mefenamic acid, meloxicam, mesalamine, miroprofen, mofebutazone, nabumetone, naproxen, niflumic acid, oxaprozin, oxpinac, oxyphenbutazone, phenylbutazone, piroxicam, pirprofen, pranoprofen, salsalate, sudoxicam, sulfasalazine, sulindac, suprofen, tenoxicam, tiopinac, tiaprofenic acid, tioxaprofen, tolfenamic acid, tolmetin, triflumidate, zidometacin, zomepirac, and combinations thereof. In a particular embodiment, the NSAID is selected from etodolac, flurbiprofen, ibuprofen, indomethacin, ketoprofen, ketorolac, meloxicam, naproxen, oxaprozin, piroxicam, and combinations thereof.

In yet another embodiment, a compound of the invention is administered in combination with an anti-lipid agent. Representative anti-lipid agents include, but are not limited to, statins such as atorvastatin, fluvastatin, lovastatin, pravastatin, rosuvastatin and simvastatin; cholesteryl ester transfer proteins (CETPs); and combinations thereof.

In yet another embodiment, a compound of the invention is administered in combination with an anti-diabetic agent. Representative anti-diabetic agents include injectable drugs as well as orally effective drugs, and combinations thereof. Examples of injectable drugs include, but are not limited to, insulin and insulin derivatives. Examples of orally effective drugs include, but are not limited to: biguanides such as metformin; glucagon antagonists; α-glucosidase inhibitors such as acarbose and miglitol; meglitinides such as repaglinide; oxadiazolidinediones; sulfonylureas such as chlorpropamide, glimepiride, glipizide, glyburide, and tolazamide; thiazolidinediones such as pioglitazone and rosiglitazone; and combinations thereof.

In one embodiment, a compound of the invention is administered in combination with an anti-thrombotic agent. Representative anti-thrombotic agents include, but are not limited to, aspirin, anti-platelet agents, heparin, and combinations thereof. Compounds of the invention may also be administered in combination with a renin inhibitor, examples of which include, but are not limited to, aliskiren, enalkiren, remikiren, and combinations thereof. In another embodiment, a compound of the invention is administered in combination with an endothelin receptor antagonist, representative examples of which include, but are not limited to, bosentan, darusentan, tezosentan, and combinations thereof. Compounds of the invention may also be administered in combination with an endothelin converting enzyme inhibitor, examples of which include, but are not limited to, phosphoramidon, CGS 26303, and combinations thereof. In yet another embodiment, a compound of the invention is administered in combination with an aldosterone antagonist. Representative aldosterone antagonists include, but are not limited to, eplerenone, spironolactone, and combinations thereof.

Combined therapeutic agents may also be helpful in further combination therapy with compounds of the invention. For example, a combination of the ACE inhibitor enalapril (in the maleate salt form) and the diuretic hydrochlorothiazide, which is sold under the mark Vaseretic®, or a combination of the calcium channel blocker amlodipine (in the besylate salt form) and the ARB olmesartan (in the medoxomil prodrug form), or a combination of a calcium channel blocker and a statin, all may also be used with the compounds of the invention. Dual-acting agents may also be helpful in combination therapy with compounds of the invention. For example, angiotensin-converting enzyme/neprilysin (ACE/NEP) inhibitors such as: AVE-0848 ((4S,7S,12bR)-7-[3-methyl-2 (S)-sulfanylbutyramido]-6-oxo-1,2,3,4,6,7,8,12b-octahydropyrido[2,1-a][2]benzazepine-4-carboxylic acid); AVE-7688 (ilepatril) and its parent compound; BMS-182657 (2-[2-oxo-3(S)-[3-phenyl-2(S)-sulfanylpropionamido]-2,3, 4,5-tetrahydro-1H-1-benzazepin-1-yl]acetic acid); CGS-26303 ([N-[2-(biphenyl-4-yl)-1(S)-(1H-tetrazol-5-yl) ethyl]amino]methylphosphonic acid); CGS-35601 (N-[1-[4-methyl-2(S)-sulfanylpentanamido]cyclopentylcarbonyl]-L-tryptophan); fasidotril; fasidotrilate; enalaprilat; ER-32935 ((3R,6S,9aR)-6-[3(S)-methyl-2 (S)-sulfanylpentanamido]-5-oxoperhydrothiazolo[3,2-a]azepine-3-carboxylic acid); gempatrilat; MDL-101264 ((4S,7S,12bR)-7-[2(S)-(2-morpholinoacetylthio)-3-phenylpropionamido]-6-oxo-1,2,3,4,6, 7,8,12b-octahydropyrido[2,1-a][2]benzazepine-4-carboxylic acid); MDL-101287 ([4S-[4α,7α(R*), 12bβ]]-7-[2-(carboxymethyl)-3-phenylpropionamido]-6-oxo-1,2,3,4,6,7, 8,12b-octahydropyrido[2,1-a][2]benzazepine-4-carboxylic acid); omapatrilat; RB-105 (N-[2 (S)-(mercaptomethyl)-3 (R)-phenylbutyl]-L-alanine); sampatrilat; SA-898 ((2R, 4R)—N-[2-(2-hydroxyphenyl)-3-(3-mercaptopropionyl) thiazolidin-4-ylcarbonyl]-L-phenylalanine); Sch-50690 (N-[1(S)-carboxy-2-[N2-(methanesulfonyl)-L-lysylamino] ethyl]-L-valyl-L-tyrosine); and combinations thereof, may also be included. In one particular embodiment, the ACE/NEP inhibitor is selected from: AVE-7688, enalaprilat, fasidotril, fasidotrilate, omapatrilat, sampatrilat, and combinations thereof.

Other therapeutic agents such as $\alpha_2$-adrenergic receptor agonists and vasopressin receptor antagonists may also be helpful in combination therapy. Exemplary $\alpha_2$-adrenergic receptor agonists include clonidine, dexmedetomidine, and guanfacine. Exemplary vasopressin receptor antagonists include tolvaptan.

The following formulations illustrate representative pharmaceutical compositions of the invention.

Exemplary Hard Gelatin Capsules for Oral Administration

A compound of the invention (50 g), spray-dried lactose (440 g) and magnesium stearate (10 g) are thoroughly blended. The resulting composition is then loaded into hard gelatin capsules (500 mg of composition per capsule). Alternately, a compound of the invention (20 mg) is thoroughly blended with starch (89 mg), microcrystalline cellulose (89 mg) and magnesium stearate (2 mg). The mixture is then passed through a No. 45 mesh U.S. sieve and loaded into a hard gelatin capsule (200 mg of composition per capsule).

Exemplary Gelatin Capsule Formulation for Oral Administration

A compound of the invention (100 mg) is thoroughly blended with polyoxyethylene sorbitan monooleate (50 mg) and starch powder (250 mg). The mixture is then loaded into a gelatin capsule (300 mg of composition per capsule). Alternately, a compound of the invention (40 mg) is thoroughly blended with microcrystalline cellulose (Avicel PH 103; 260 mg) and magnesium stearate (0.8 mg). The mixture is then loaded into a gelatin capsule (Size #1, White, Opaque) (300 mg of composition per capsule).

Exemplary Tablet Formulation for Oral Administration

A compound of the invention (10 mg), starch (45 mg) and microcrystalline cellulose (35 mg) are passed through a No. 20 mesh U.S. sieve and mixed thoroughly. The granules so produced are dried at 50-60° C. and passed through a No. 16 mesh U.S. sieve. A solution of polyvinylpyrrolidone (4 mg as a 10% solution in sterile water) is mixed with sodium carboxymethyl starch (4.5 mg), magnesium stearate (0.5 mg), and talc (1 mg), and this mixture is then passed through a No. 16 mesh U.S. sieve. The sodium carboxymethyl starch, magnesium stearate and talc are then added to the granules. After mixing, the mixture is compressed on a tablet machine to afford a tablet weighing 100 mg.

Alternately, a compound of the invention (250 mg) is thoroughly blended with microcrystalline cellulose (400 mg), silicon dioxide fumed (10 mg), and stearic acid (5 mg). The mixture is then compressed to form tablets (665 mg of composition per tablet).

Alternately, a compound of the invention (400 mg) is thoroughly blended with cornstarch (50 mg), croscarmellose sodium (25 mg), lactose (120 mg), and magnesium stearate (5 mg). The mixture is then compressed to form a single-scored tablet (600 mg of composition per tablet).

Alternately, a compound of the invention (100 mg) is thoroughly blended with cornstarch (100 mg) with an aqueous solution of gelatin (20 mg). The mixture is dried and ground to a fine powder Microcrystalline cellulose (50 mg) and magnesium stearate (5 mg) are the admixed with the gelatin formulation, granulated and the resulting mixture compressed to form tablets (100 mg of active per tablet).

Exemplary Suspension Formulation for Oral Administration

The following ingredients are mixed to form a suspension containing 100 mg of active agent per 10 mL of suspension:

| Ingredients | Amount | |
|---|---|---|
| Compound of the invention | 1.0 | g |
| Fumaric acid | 0.5 | g |
| Sodium chloride | 2.0 | g |
| Methyl paraben | 0.15 | g |
| Propyl paraben | 0.05 | g |
| Granulated sugar | 25.5 | g |
| Sorbitol (70% solution) | 12.85 | g |
| Veegum ® K (magnesium aluminum silicate) | 1.0 | g |
| Flavoring | 0.035 | mL |
| Colorings | 0.5 | mg |
| Distilled water | q.s. to 100 | mL |

Exemplary Liquid Formulation for Oral Administration

A suitable liquid formulation is one with a carboxylic acid-based buffer such as citrate, lactate and maleate buffer solutions. For example, a compound of the invention (which may be pre-mixed with DMSO) is blended with a 100 mM ammonium citrate buffer and the pH adjusted to pH 5, or with is blended with a 100 mM citric acid solution and the pH adjusted to pH 2. Such solutions may also include a solubilizing excipient such as a cyclodextrin, for example the solution may include 10 wt % hydroxypropyl-β-cyclodextrin.

Exemplary Injectable Formulation for Administration by Injection

A compound of the invention (0.2 g) is blended with 0.4 M sodium acetate buffer solution (2.0 mL). The pH of the resulting solution is adjusted to pH 4 using 0.5 N aqueous hydrochloric acid or 0.5 N aqueous sodium hydroxide, as necessary, and then sufficient water for injection is added to provide a total volume of 20 mL. The mixture is then filtered through a sterile filter (0.22 micron) to provide a sterile solution suitable for administration by injection.

Exemplary Compositions for Administration by Inhalation

A compound of the invention (0.2 mg) is micronized and then blended with lactose (25 mg). This blended mixture is then loaded into a gelatin inhalation cartridge. The contents of the cartridge are administered using a dry powder inhaler, for example.

Alternately, a micronized compound of the invention (10 g) is dispersed in a solution prepared by dissolving lecithin (0.2 g) in demineralized water (200 mL). The resulting suspension is spray dried and then micronized to form a micronized composition comprising particles having a mean diameter less than about 1.5 µm. The micronized composition is then loaded into metered-dose inhaler cartridges containing pressurized 1,1,1,2-tetrafluoroethane in an amount sufficient to provide about 10 µg to about 500 µg of the compound of the invention per dose when administered by the inhaler.

Alternately, a compound of the invention (25 mg) is dissolved in citrate buffered (pH 5) isotonic saline (125 mL). The mixture is stirred and sonicated until the compound is dissolved. The pH of the solution is checked and adjusted, if necessary, to pH 5 by slowly adding aqueous 1N sodium hydroxide. The solution is administered using a nebulizer device that provides about 10 µg to about 500 µg of the compound of the invention per dose.

EXAMPLES

The following Preparations and Examples are provided to illustrate specific embodiments of the invention. These specific embodiments, however, are not intended to limit the scope of the invention in any way unless specifically indicated.

The following abbreviations have the following meanings unless otherwise indicated and any other abbreviations used herein and not defined have their standard meaning:

| | |
|---|---|
| ACE | angiotensin converting enzyme |
| APP | aminopeptidase P |
| $AT_1$ | angiotensin II type 1 (receptor) |
| $AT_2$ | angiotensin II type 2 (receptor) |
| BCA | bicinchoninic acid |
| BSA | bovine serum albumin |
| DCM | dichloromethane |
| DMF | N, N-dimethylformamide |
| DMSO | dimethyl sulfoxide |
| Dnp | 2,4-dinitrophenyl |
| DOCA | deoxycorticosterone acetate |
| EDC | N-(3-dimethylaminopropyl)-N'-ethylcarbodiimide |
| EDTA | ethylenediaminetetraacetic acid |
| EGTA | ethylene glycol bis(β-aminoethyl ether)-N,N,N'N'-tetraacetic acid |
| EtOAc | ethyl acetate |
| EtOH | ethanol |
| HOBt | 1-hydroxybenzotriazole |
| Mca | (7-methoxycoumarin-4-yl)acyl |
| MeCN | acetonitrile |
| MeOH | methanol |
| NBS | N-bromosuccinimide |
| NEP | neprilysin (EC 3.4.24.11) |
| PBS | phosphate buffered saline |
| SHR | spontaneously hypertensive rat |
| TFA | trifluoroacetic acid |
| THF | tetrahydrofuran |
| Tris | tris(hydroxymethyl)aminomethane |
| Tween-20 | polyethylene glycol sorbitan monolaurate |

Unless noted otherwise, all materials, such as reagents, starting materials and solvents, were purchased from commercial suppliers (such as Sigma-Aldrich, Fluka Riedel-de Haën, and the like) and were used without further purification.

Reactions were run under nitrogen atmosphere, unless noted otherwise. The progress of reactions were monitored by thin layer chromatography (TLC), analytical high performance liquid chromatography (anal. HPLC), and mass spectrometry, the details of which are given in specific examples. Solvents used in analytical HPLC were as follows: solvent A was 98% water/2% MeCN/1.0 mL/L TFA; solvent B was 90% MeCN/10% water/1.0 mL/L TFA.

Reactions were worked up as described specifically in each preparation or example; commonly reaction mixtures were purified by extraction and other purification methods such as temperature-, and solvent-dependent crystallization, and precipitation. In addition, reaction mixtures were routinely purified by preparative HPLC, typically using Microsorb C18 and Microsorb BDS column packings and conventional eluents. Characterization of reaction products was routinely carried out by mass and $^1$H-NMR spectrometry. For NMR measurement, samples were dissolved in deuterated solvent ($CD_3OD$, $CDCl_3$, or DMSO-$d_6$), and $^1$H-NMR spectra were acquired with a Varian Gemini 2000 instrument (400 MHz) under standard observation conditions. Mass spectrometric identification of compounds was typically conducted using an electrospray ionization method (ESMS) with an Applied Biosystems (Foster City, Calif.) model API 150 EX instrument or an Agilent (Palo Alto, Calif.) model 1200 LC/MSD instrument.

Preparation 1

7-Methyl-2-propyl-3H-benzoimidazole-5-carboxylic acid ((R)-1-benzyl-2-benzyloxycarbamoylethyl) amide

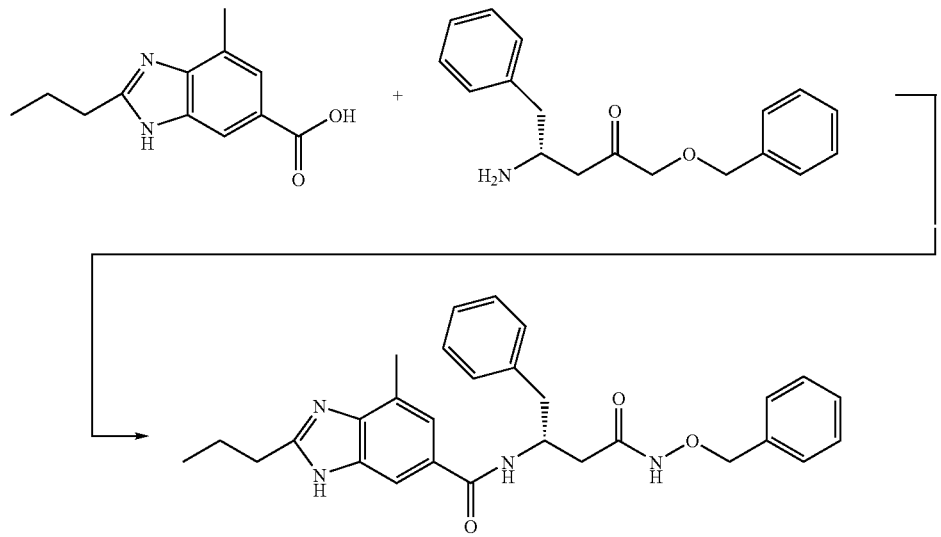

To a solution of 7-methyl-2-propyl-3H-benzoimidazole-5-carboxylic acid (164 mg, 752 µmol) and (R)-3-amino-N-benzyloxy-4-phenylbutyramide (TFA salt: 300 mg, 754 µmol) in DMF (10 mL) containing triethylamine (210 µL), was added HOBt (151 µg, 755 µmol) and EDC (151 mg, 788 µmol). The mixture was stirred at room temperature overnight and concentrated in vacuo, yielding a pale brown residue. The residue was dissolved in DCM (100 mL) and washed sequentially with 1M $H_3PO_4$, a saturated $NaHCO_3$ solution, and saturated aqueous NaCl. The organic layer was collected, dried over $MgSO_4$, and concentrated to afford the title compound as a pale yellow oil (150 mg; 41% yield), which was used without further treatment. ESMS $[M+H]^+$ calcd for $C_{29}H_{32}N_4O_3$, 485.26. found 485.5.

Preparation 2

4-[6-((R)-1-Benzyl-2-benzyloxycarbamoylethylcarbamoyl)-4-methyl-2-propylbenzoimidazol-1-ylmethyl]benzoic Acid Methyl Ester (2a) and 4-[5-((R)-1-Benzyl-2-benzyloxycarbamoylethylcarbamoyl-7-methyl-2-propylbenzoimidazol-1-ylmethyl]benzoic Acid Methyl Ester (2b)

(2a)

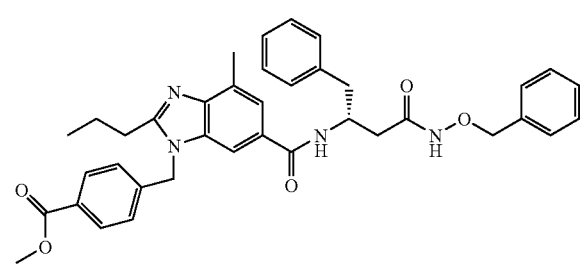

(2b)

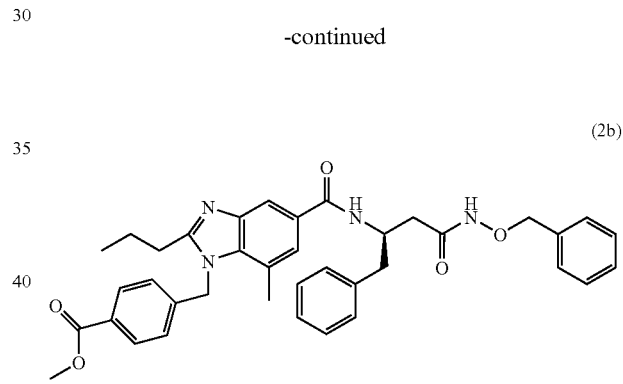

To a cold solution of 7-methyl-2-propyl-3H-benzoimidazole-5-carboxylic acid ((R)-1-benzyl-2-benzyloxycarbamoylethyl)amide (150 mg, 310 µmol) in DMF (10 mL) in an ice bath, was added NaH (60% dispersion in mineral oil; 56 mg) under nitrogen. After stirring the mixture for 20 minutes, 4-bromomethylbenzoic acid methyl ester (71 mg, 310 µmol) was added. The final mixture was stirred at room temperature for 2 hours, then at 80° C. for 12 hours. The mixture was cooled, and concentrated in vacuo. The resulting residue was washed with hexane (10 mL), dissolved in DCM (50 mL), and sequentially washed with 1M $H_3PO_4$, a saturated $NaHCO_3$ solution, and saturated aqueous NaCl. The organic layer was collected and dried over $MgSO_4$, and concentrated in vacuo, to afford a pale yellow oil. The crude oil contained a mixture of two alkylation products, compound 2a (a major product) and compound 2b (a minor desired product). ESMS $[M+H]^+$ calcd for $C_{38}H_{40}N_4O_5$, 632.30. found 633.4.

Preparation 3

4-[6-((R)-1-Benzyl-2-benzyloxycarbamoylethylcarbamoyl)-4-methyl-2-propylbenzoimidazol-1-ylmethyl]benzoic Acid (3a) and 4-[5-((R)-1-Benzyl-2-benzyloxycarbamoylethylcarbamoyl)-7-methyl-2-propylbenzoimidazol-1-ylmethyl]benzoic Acid (3b)

Example 1

4-[6-((R)-1-Benzyl-2-hydroxycarbamoylethylcarbamoyl)-4-methyl-2-propylbenzoimidazol-1-ylmethyl]benzoic Acid (1-a) and 4-[5-((R)-1-Benzyl-2-hydroxycarbamoylethylcarbamoyl)-7-methyl-2-propylbenzoimidazol-1-ylmethyl]benzoic Acid (1-b)

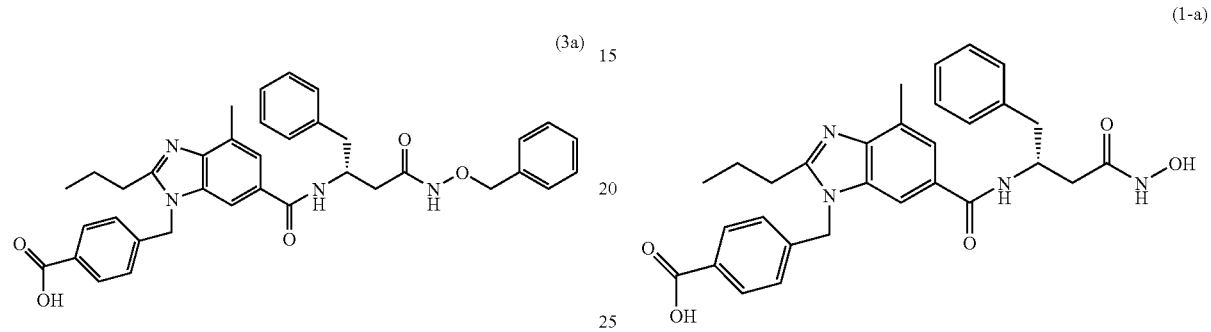

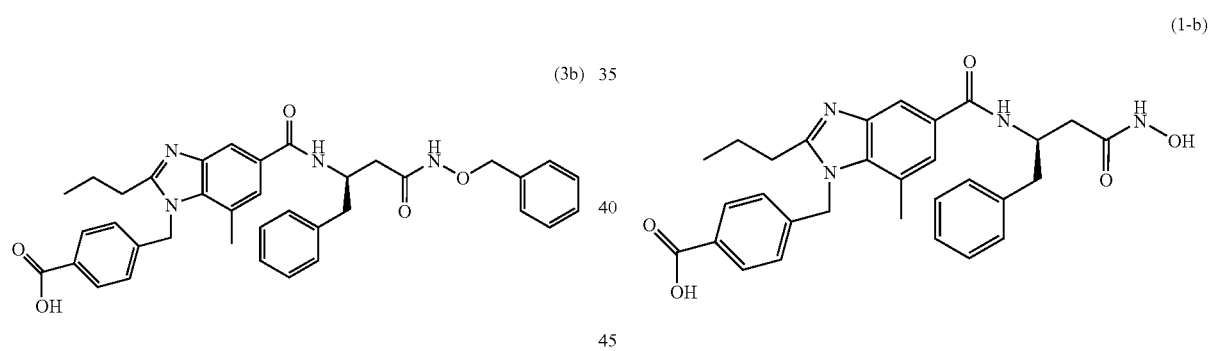

A mixture of 4-[6-((R)-1-benzyl-2-benzyloxycarbamoylethylcarbamoyl)-4-methyl-2-propylbenzoimidazol-1-ylmethyl]benzoic acid methyl ester and 4-[5-((R)-1-benzyl-2-benzyloxycarbamoylethylcarbamoyl)-7-methyl-2-propylbenzoimidazol-1-ylmethyl]benzoic acid methyl ester was dissolved in a mixture of MeOH (20 mL) and THF (5 mL), to which an aqueous NaOH solution (33 mg, 825 µmol; 1 mL) was added. The mixture was stirred at room temperature for 24 hours, and concentrated in vacuo to yield a pale brown residue. The residue was suspended in water, followed by the addition of 1M $H_3PO_4$ until the pH of the solution reached 3. The precipitated solid was collected, dissolved in MeOH and evaporated to dryness to yield the title compounds as a pale yellow oil, which was used without further purification. ESMS [M+H]$^+$ calcd for $C_{37}H_{38}N_4O_5$, 619.29. found 619.0.

To a nitrogen-saturated solution of a mixture of 4-[6-((R)-1-benzyl-2-benzyloxycarbamoylethylcarbamoyl)-4-methyl-2-propylbenzoimidazol-1-ylmethyl]benzoic acid and 4-[5-((R)-1-benzyl-2-benzyloxycarbamoylethylcarbamoyl)-7-methyl-2-propylbenzoimidazol-1-ylmethyl]benzoic acid, was added 10% Pd/C (200 mg). The mixture was degassed and stirred under hydrogen (1 atm) overnight at room temperature. The mixture was filtered through Celite®, concentrated to dryness, and purified by preparative reversed phase HPLC. The desired product, compound 1-b, was isolated as colorless solid (TFA salt; 30 mg).

Compound 1-a: ESMS [M+H]$^+$ calcd for $C_{30}H_{32}N_4O_5$, 529.25. found 529.2. Retention time (anal. HPLC: 10-70% MeCN/$H_2O$ over 5 min)=2.26 min.

Compound 1-b: ESMS [M+H]$^+$ calcd for $C_{30}H_{32}N_4O_5$, 529.25. found 529.2. Retention time (anal. HPLC: 10-70% MeCN/$H_2O$ over 5 min)=2.36 min.

Preparation 4

5-(4'-Bromomethylbiphenyl-2-yl)-1-trityl-1H-tetrazole

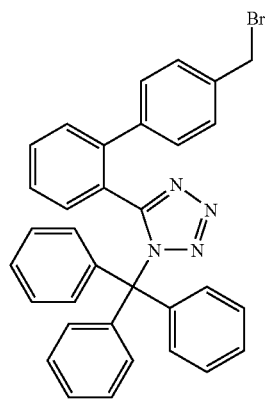

To a nitrogen-saturated suspension of N-triphenylmethyl-5-[4'-methylbiphenyl-2-yl]tetrazole (10 g, 20.9 mmol) in DCM was added NBS (3.7 g, 20.9 mmol) and a catalytic amount of benzoyl peroxide (60 mg, 240 μmol). The mixture was stirred at reflux for 15 hours. After cooling to room temperature, the precipitate was filtered and the organic solution was concentrated in vacuo. Silica gel chromatography (EtOAc/hexane) gave the title compound as a white solid.

$^1$H-NMR (400 MHz, DMSO-$d_6$): δ (ppm) 4.61 (s, 2H), 6.80 (d, 6H), 7.01 (d, 2H), 7.24 (d, 2H), 7.28-7.35 (m, 9H), 7.43-7.45 (dd, 1H), 7.50-7.56 (td, 1H), 7.58-7.60 (td, 1H), 7.77-7.79 (dd, 1H).

Preparation 5

7-Methyl-2-propyl-3-[2'-(1H-tetrazol-5-yl)biphenyl-4-ylmethyl]-3H-benzoimidazole-5-carboxylic acid ((R)-1-benzyl-2-benzyloxycarbamoylethyl)amide (5a) and 7-Methyl-2-propyl-1-[2'-(1H-tetrazol-5-yl)biphenyl-4-ylmethyl]-1H-benzoimidazole-5-carboxylic acid ((R)-1-benzyl-2-benzyloxycarbamoylethyl)amide (5b)

(5a)
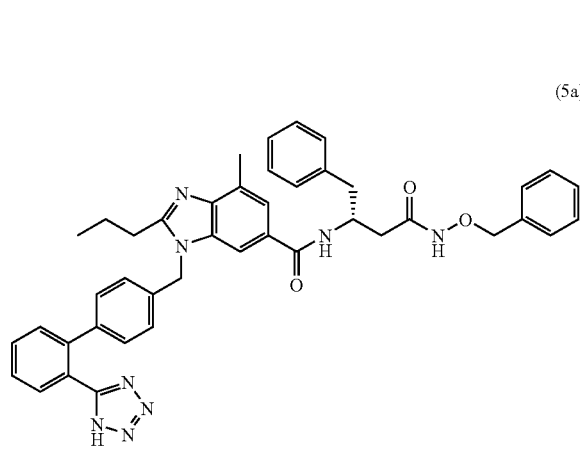

(5b)
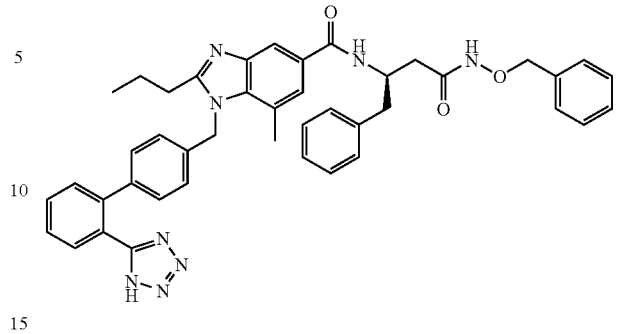

To a cold solution of 7-methyl-2-propyl-3H-benzoimidazole-5-carboxylic acid ((R)-1-benzyl-2-benzyloxycarbamoylethyl)amide (800 mg, 825 μmol) in DMF (50 mL) in ice bath was added NaH (60% dispersion in oil; 99 mg, 2.5 mmol) in small portions. After stirring for 30 minutes at the same temperature, 5-(4'-bromomethylbiphenyl-2-yl)-1-trityl-1H-tetrazole (460 mg, 825 μmol) was added to the mixture, and the final mixture was stirred at room temperature for 12 hours, then at 70° C. for 6 hours. The mixture was concentrated in vacuo. The residue was dissolved in EtOAc (200 mL) and washed with saturated aqueous NaCl. The organic layer was dried over MgSO$_4$, and evaporated in vacuo, affording a pale yellow oil. The oil was dissolved in DCM (10 mL), followed by the addition of TFA (10 mL). The final mixture was stirred at room temperature for 1 hour, and concentrated to dryness, yielding a pale yellow oil. The oil was rinsed with ether and dried. The crude material was found to contain two regioisomeric N-alkylation products, compound 5a (a major product) and compound 5b (a minor desired product). ESMS [M+H]$^+$ calcd for $C_{43}H_{42}N_8O_3$, 719.35. found 719.3.

Example 2

7-Methyl-2-propyl-3-[2'-(1H-tetrazol-5-yl)biphenyl-4-ylmethyl]-3H-benzoimidazole-5-carboxylic acid ((R)-1-benzyl-2-hydroxycarbamoylethyl)amide (2-a) and 7-Methyl-2-propyl-1-[2'-(1H-tetrazol-5-yl)biphenyl-4-ylmethyl]-1H-benzoimidazole-5-carboxylic acid ((R)-1-benzyl-2-hydroxycarbamoylethyl)amide (2-b)

(2-a)
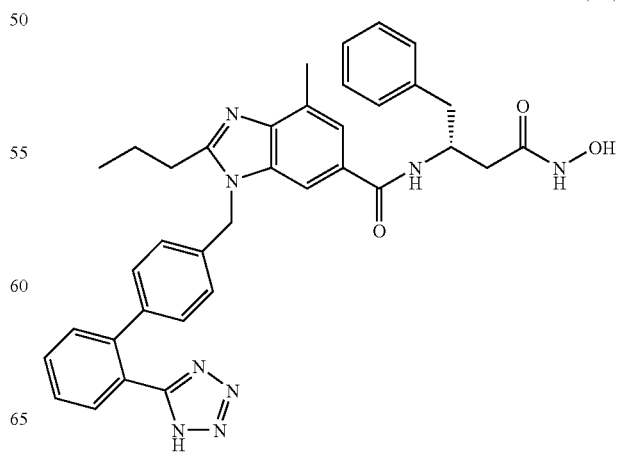

(2-b)

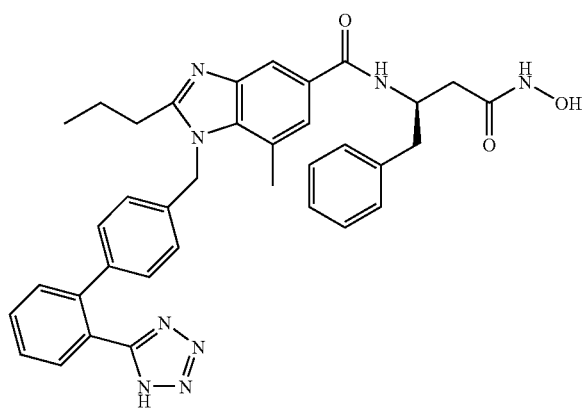

A mixture of 7-methyl-2-propyl-3-[2'-(1H-tetrazol-5-yl) biphenyl-4-ylmethyl]-3H-benzoimidazole-5-carboxylic acid ((R)-1-benzyl-2-benzyloxycarbamoylethyl)amide and 7-methyl-2-propyl-1-[2'-(1H-tetrazol-5-yl)biphenyl-4-ylmethyl]-1H-benzoimidazole-5-carboxylic acid ((R)-1-benzyl-2-benzyloxycarbamoylethyl)amide were dissolved in EtOH (50 mL), followed by the addition of 10% Pd/C (200 mg). The final mixture was bubbled with nitrogen gas for 5 minutes, and degassed. The reaction mixture was stirred under hydrogen (1 atm) for 12 hours, and filtered through Celite®. The filtrate was concentrated to afford a pale brown oil. The oil was dissolved in 50% aqueous acetic acid, and purified by reversed phase preparative HPLC. The desired product, compound 2-b (minor component), was isolated as a colorless solid.

Compound 2-a: ESMS [M+H]$^+$ calcd for $C_{36}H_{36}N_8O_3$, 629.30. found 629.4. Retention time (anal. HPLC: 10-70% MeCN/H$_2$O over 5 min)=2.66 min.

Compound 2-b: ESMS [M+H]$^+$ calcd for $C_{36}H_{36}N_8O_3$, 629.30. found 629.4. Retention time (anal. HPLC: 10-70% MeCN/H$_2$O over 5 min)=2.75 min.

Preparation 6

2-Ethoxy-3-[2'-(1H-tetrazol-5-yl)-biphenyl-4-ylmethyl]-3H-benzoimidazole-4-carboxylic acid (1-chloromethyl-3-methylbutyl)amide

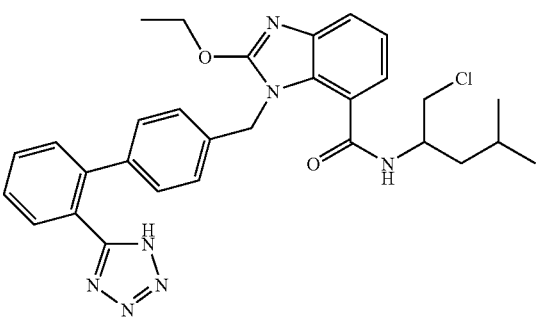

1-Chloromethyl-3-methylbutylamine hydrochloride (39 mg, 230 µmol) and triethylamine (31.6 µL, 1 equiv) were dissolved in DCM (2.00 mL). 2-Ethoxy-3-[2'-(1H-tetrazol-5-yl)-biphenyl-4-ylmethyl]-3H-benzimidazole-4-carboxylic acid (100 mg, 1 equiv) was added, followed by HOBt (31 mg, 1 equiv) and EDC HCl (51 mg, 1.1 equiv). The reaction was stirred overnight at room temperature, then diluted with DCM (10 mL), washed (H$_2$O, 10 mL), dried over NaSO$_4$, decanted, and the solvent evaporated. The residue was purified by flash chromatography (5% MeOH/DCM) to afford the title compound as a white solid (19 mg, 15%). ESMS [M+H]$^+$ calcd for $C_{30}H_{32}ClN_7O_2$ 557.3. found 558.3.

Preparation 7

Thioacetic Acid S-[2-({2-ethoxy-3-[2'-(1H-tetrazol-5-yl) biphenyl-4-ylmethyl]-3H-benzoimidazole-4-carbonyl}amino)-4-methylpentyl]ester

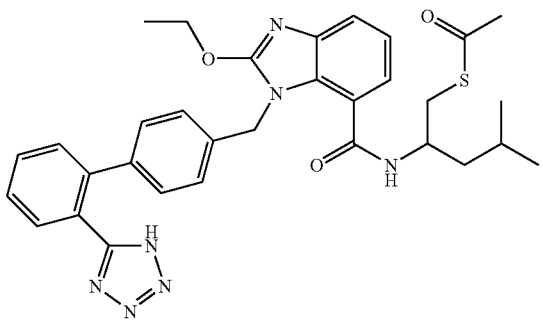

2-Ethoxy-3-[2'-(1H-tetrazol-5-yl)-biphenyl-4-ylmethyl]-3H-benzoimidazole-4-carboxylic acid (1-chloromethyl-3-methylbutyl)amide (100 mg, 180 µmol) and potassium thioacetate (31 mg, 15 equiv) were dissolved in MeCN (5 mL) and heated at 90° C. overnight. The solvent was evaporated and the residue partitioned between water (10 mL) and EtOAc (10 mL). The aqueous phase was discarded, the organic layer washed with saturated aqueous NaCl, dried over NaSO$_4$, decanted, and the solvent evaporated. The crude product (80 mg, 70%) was used without further purification. ESMS [M+H]$^+$ calcd for $C_{32}H_{35}N_7O_3S$, 597.3. found 598.3.

Example 3

2-Ethoxy-3-[2'-(1H-tetrazol-5-yl)-biphenyl-4-ylmethyl]-3H-benzoimidazole-4-carboxylic acid (1-mercaptomethyl-3-methylbutyl)amide

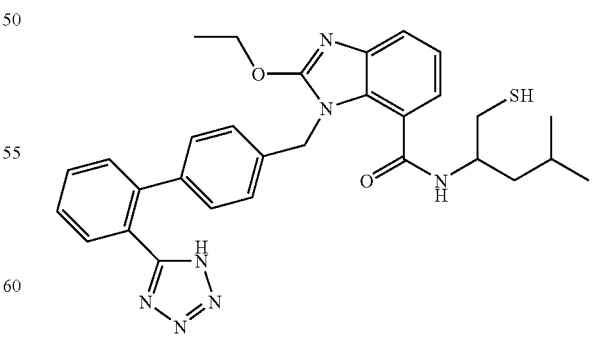

Thioacetic acid S-[2-({2-ethoxy-3-[2'-(1H-tetrazol-5-yl) biphenyl-4-ylmethyl]-3H-benzoimidazole-4-carbonyl}amino)-4-methylpentyl]ester (80 mg, 0.1 mmol) was dissolved in MeOH (5 mL) and 1M NaOH (5 mL). The mixture was stirred for 1 hour with nitrogen gas bubbling through the solution. The reaction was quenched with acetic acid (5 mL) and the mixture evaporated to dryness. The residue was purified using reverse phase preparative HPLC to afford the title compound (540 μg). ESMS [M+H]+ calcd for $C_{30}H_{33}N_7O_2S$, 555.3. found 556.4.

Example 4

Following the procedures described in Examples above, and substituting the appropriate starting materials and reagents, compounds 4-1 to 4-4, having the following formula, were also prepared:

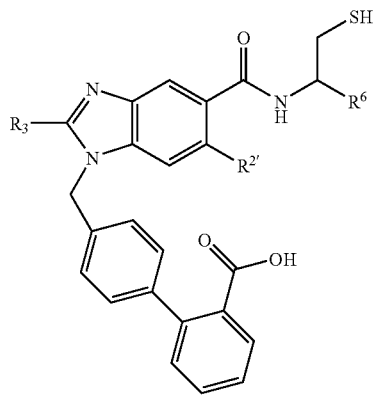

| Ex. | $R^{2'}$ | $R^3$ | $R^6$ |
|---|---|---|---|
| 4-1 | H | —(CH$_2$)$_2$—CH$_3$ | benzyl |
| 4-2 | H | —(CH$_2$)$_2$—CH$_3$ | —CH$_2$—CH(CH$_3$)$_2$ |
| 4-3 | H | —O—CH$_2$CH$_3$ | benzyl |
| 4-4 | —O—CH$_3$ | —(CH$_2$)$_2$—CH$_3$ | benzyl |

(4-1) 4'-[5-((R)-1-benzyl-2-mercaptoethylcarbamoyl)-2-propylbenzoimidazol-1-ylmethyl]biphenyl-2-carboxylic acid. MS m/z: [M+H]+ calcd for $C_{34}H_{33}N_3O_3S$, 564.22. found 564.6.

(4-2) 4'-[5-((R)-1-mercaptomethyl-3-methylbutylcarbamoyl)-2-propylbenzoimidazol-1-ylmethyl]biphenyl-2-carboxylic acid. MS m/z: [M+H]+ calcd for $C_{31}H_{35}N_3O_3S$, 530.24. found 530.6.

(4-3) 4'-[5-((R)-1-benzyl-2-mercaptoethylcarbamoyl)-2-ethoxybenzoimidazol-1-ylmethyl]biphenyl-2-carboxylic acid. MS m/z: [M+H]+ calcd for $C_{33}H_{31}N_3O_4S$, 566.20. found 566.4.

(4-4) 4'-[5-((R)-1-benzyl-2-mercaptoethylcarbamoyl)-6-methoxy-2-propylbenzoimidazol-1-ylmethyl]biphenyl-2-carboxylic acid. MS m/z: [M+H]+ calcd for $C_{35}H_{35}N_3O_4S$, 594.24. found 594.4.

Assay 1

AT$_1$ and AT$_2$ Radioligand Binding Assays

These in vitro assays were used to assess the ability of test compounds to bind to the AT$_1$ and the AT$_2$ receptors.

Membrane Preparation from Cells Expressing Human AT$_1$ or AT$_2$ Receptors

Chinese hamster ovary (CHO-K1) derived cell lines stably expressing the cloned human AT$_1$ or AT$_2$ receptors, respectively, were grown in HAM's-F12 medium supplemented with 10% fetal bovine serum, 10 μg/ml penicillin/streptomycin, and 500 μg/ml geneticin in a 5% CO$_2$ humidified incubator at 37° C. AT$_2$ receptor expressing cells were grown in the additional presence of 100 nM PD123,319 (AT$_2$ antagonist). When cultures reached 80-95% confluence, the cells were washed thoroughly in PBS and lifted with 5 mM EDTA. Cells were pelleted by centrifugation and snap frozen in MeOH-dry ice and stored at −80° C. until further use.

For membrane preparation, cell pellets were resuspended in lysis buffer (25 mM Tris/HCl pH 7.5 at 4° C., 1 mM EDTA, and one tablet of Complete Protease Inhibitor Cocktail Tablets with 2 mM EDTA per 50 mL buffer (Roche cat. #1697498, Roche Molecular Biochemicals, Indianapolis, Ind.)) and homogenized using a tight-fitting Dounce glass homogenizer (10 strokes) on ice. The homogenate was centrifuged at 1000×g, the supernatant was collected and centrifuged at 20,000×g. The final pellet was resuspended in membrane buffer (75 mM Tris/HCl pH 7.5, 12.5 mM MgCl$_2$, 0.3 mM EDTA, 1 mM EGTA, 250 mM sucrose at 4° C.) and homogenized by extrusion through a 20G gauge needle. Protein concentration of the membrane suspension was determined by the method described in Bradford (1976) *Anal Biochem.* 72:248-54. Membranes were snap frozen in MeOH-dry ice and stored at −80° C. until further use.

Ligand Binding Assay to Determine Compound Affinities for the Human AT$_1$ and AT$_2$ Angiotensin Receptors Binding assays were performed in 96-well Acrowell filter plates (Pall Inc., cat. #5020) in a total assay volume of 100 μL with 0.2 μg membrane protein for membranes containing the human AT$_1$ receptor, or 2 μg membrane protein for membranes containing the human AT$_2$ receptor in assay buffer (50 mM Tris/HCl pH 7.5 at 20° C., 5 mM MgCl$_2$, 25 μM EDTA, 0.025% BSA). Saturation binding studies for determination of K$_d$ values of the ligand were done using N-terminally Europium-labeled angiotensin-TI ([Eu]AngII, H-(Eu—N$^1$)-Ahx-Asp-Arg-Val-Tyr-Ile-His-Pro-Phe-OH; PerkinElmer, Boston, Mass.) at 8 different concentrations ranging from 0.1 nM to 30 nM. Displacement assays for determination of pK$_i$ values of test compounds were done with [Eu]AngII at 2 nM and 11 different concentrations of drug ranging from 1 pM to 10 μM. Drugs were dissolved to a concentration of 1 mM in DMSO and from there serially diluted into assay buffer. Nonspecific binding was determined in the presence of 10 μM unlabeled angiotensin-II. Assays were incubated for 120 minutes in the dark, at room temperature or 37° C., and binding reactions were terminated by rapid filtration through the Acrowell filter plates followed by three washes with 200 μL ice cold wash buffer (50 mM Tris/HCl pH 7.5 at 4° C., 5 mM MgCl$_2$) using a Waters filtration manifold. Plates were tapped dry and incubated with 50 μl DELFIA Enhancement Solution (PerkinElmer cat. #4001-0010) at room temperature for 5 minutes on a shaker. Filter-bound [Eu]AngII was quantitated immediately on a Fusion plate reader (PerkinElmer) using Time Resolved Fluorescence (TRF). Binding data were analyzed by nonlinear regression analysis with the GraphPad Prism Software package (GraphPad Software, Inc., San Diego, Calif.) using the 3-parameter model for one-site competition. The BOTTOM (curve minimum) was fixed to the value for nonspecific binding, as determined in the presence of 10 μM angiotensin II. K$_i$ values for drugs were calculated from observed IC$_{50}$ values and the K$_d$ value of [Eu]AngII according to the Cheng-Prusoff equation described in Cheng et al. (1973) *Biochem Pharmacol.* 22(23):3099-108. Selectivities of test compounds for the $AT_1$ receptor over the $AT_2$ receptor were calculated as the ratio of $AT_2K_i/AT_1K_i$. Binding affinities of test compounds were expressed as negative decadic logarithms of the $K_i$ values ($pK_i$).

In this assay, a higher $pK_i$ value indicates that the test compound has a higher binding affinity for the receptor tested. Exemplary compounds of the invention that were tested in this assay, typically were found to have a $pK_i$ at the $AT_1$ receptor greater than or equal to about 5.0.

Assay 2

In Vitro Assays for the Quantitation of Inhibitor Potencies ($IC_{50}$) at Human and Rat NEP, and Human ACE The inhibitory activities of compounds at human and rat NEP and human ACE were determined using in vitro assays as described below.

Extraction of NEP Activity from Rat Kidneys

Rat NEP was prepared from the kidneys of adult Sprague Dawley rats. Whole kidneys were washed in cold PBS and brought up in ice-cold lysis buffer (1% Triton X-114, 150 mM NaCl, 50 mM Tris pH 7.5; Bordier (1981) *J. Biol. Chem.* 256:1604-1607) in a ratio of 5 mL of buffer for every gram of kidney. Samples were homogenized using a polytron hand held tissue grinder on ice. Homogenates were centrifuged at 1000×g in a swinging bucket rotor for 5 minutes at 3° C. The pellet was resuspended in 20 mL of ice cold lysis buffer and incubated on ice for 30 minutes. Samples (15-20 mL) were then layered onto 25 mL of ice-cold cushion buffer (6% w/v sucrose, 50 mM pH 7.5 Tris, 150 mM NaCl, 0.06%, Triton X-114), heated to 37° C. for 3-5 minutes and centrifuged at 1000×g in a swinging bucket rotor at room temperature for 3 minutes. The two upper layers were aspirated off, leaving a viscous oily precipitate containing the enriched membrane fraction. Glycerol was added to a concentration of 50% and samples were stored at −20° C. Protein concentrations were quantitated using a BCA detection system with BSA as a standard.

Enzyme Inhibition Assays

Recombinant human NEP and recombinant human ACE were obtained commercially (R&D Systems, Minneapolis, Minn., catalog numbers 1182-ZN and 929-ZN, respectively). The fluorogenic peptide substrate Mca-BK2 (Mca-Arg-Pro-Pro-Gly-Phe-Ser-Ala-Phe-Lys(Dnp)-OH; Johnson et al. (2000) *Anal. Biochem.* 286: 112-118) was used for the human NEP and ACE assays, and Mca-RRL (Mca-DArg-Arg-Leu-(Dnp)-OH; Medeiros et al. (1997) *Braz. J. Med. Biol. Res.* 30:1157-1162) was used for the rat NEP assay (both from Anaspec, San Jose, Calif.).

The assays were performed in 384-well white opaque plates at room temperature using the respective fluorogenic peptides at a concentration of 10 μM in assay buffer (50 mM Tris/HCl at 25° C., 100 mM NaCl, 0.01% Tween-20, 1 μM Zn, 0.025% BSA). Human NEP and human ACE were used at concentrations that resulted in quantitative proteolysis of 5 μM of Mca-BK2 within 20 minutes at room temperature. The rat NEP enzyme preparation was used at a concentration that yielded quantitative proteolysis of 3 μM of Mca-RRL within 20 minutes at room temperature.

Assays were started by adding 25 μL of enzyme to 12.5 μL of test compound at 12 concentrations (10 μM to 20 pM). Inhibitors were allowed to equilibrate with the enzyme for 10 minutes before 12.5 μL of the fluorogenic substrates were added to initiate the reaction. Reactions were terminated by the addition of 10 μL of 3.6% glacial acetic acid after 20 minutes of incubation. Plates were read on a fluorometer with excitation and emission wavelengths set to 320 nm and 405 nm, respectively.

Raw data (relative fluorescence units) were normalized to % activity from the average high readings (no inhibition, 100% enzyme activity) and average low readings (full inhibition, highest inhibitor concentration, 0% enzyme activity) using three standard NEP and ACE inhibitors, respectively. Nonlinear regression of the normalized data was performed using a one site competition model (GraphPad Software, Inc., San Diego, Calif.). Data were reported as $pIC_{50}$ values.

Exemplary compounds of the invention that were tested in this assay, typically were found to have a $pIC_{50}$ for the NEP enzyme greater than or equal to about 5.0.

Assay 3

Pharmacodynamic (PD) Assay for ACE, $AT_1$, and NEP Activity in Anesthetized Rats Male, Sprague Dawley, normotensive rats are anesthetized with 120 mg/kg (i.p.) of inactin. Once anesthetized, the jugular vein, carotid artery (PE 50 tubing) and bladder (URI-1 urinary silicone catheter) are cannulated and a tracheotomy is performed (Teflon Needle, size 14 gauge) to facilitate spontaneous respiration. The animals are then allowed a 60 minute stabilization period and kept continuously infused with 5 mL/kg/h of saline (0.9%) throughout, to keep them hydrated and ensure urine production. Body temperature is maintained throughout the experiment by use of a heating pad. At the end of the 60 minute stabilization period, the animals are dosed intravenously (i.v.) with two doses of angiotensin (AngI, 1.0 μg/kg, for ACE inhibitor activity; AngII, 0.1 μg/kg, for $AT_1$ receptor antagonist activity) at 15 minutes apart. At 15 minutes post-second dose of angiotensin (AngI or AngII), the animals are treated with vehicle or test compound. Five minutes later, the animals are additionally treated with a bolus i.v. injection of atrial natriuretic peptide (ANP; 30 μg/kg). Urine collection (into pre-weighted eppendorf tubes) is started immediately after the ANP treatment and continued for 60 minutes. At 30 and 60 minutes into urine collection, the animals are re-challenged with angiotensin (AngI or AngII). Blood pressure measurements are done using the Notocord system (Kalamazoo, Mich.). Urine samples are frozen at −20° C. until used for the cGMP assay. Urine cGMP concentrations are determined by Enzyme Immuno Assay using a commercial kit (Assay Designs, Ann Arbor, Mich., Cat. No. 901-013). Urine volume is determined gravimetrically. Urinary cGMP output is calculated as the product of urine output and urine cGMP concentration. ACE inhibition or $AT_1$ antagonism is assessed by quantifying the % inhibition of pressor response to AngI or AngII, respectively. NEP inhibition is assessed by quantifying the potentiation of ANP-induced elevation in urinary cGMP output.

Assay 4

In Vivo Evaluation of Antihypertensive Effects in the Conscious SHR Model of Hypertension Spontaneously hypertensive rats (SHR, 14-20 weeks of age) are allowed a minimum of 48 hours acclimation upon arrival at the testing site. Seven days prior to testing, the animals are either placed on a restricted low-salt diet with food containing 0.11% of sodium for sodium depleted SHRs (SD-SHR) or are placed on a normal diet for sodium repleted SHRs (SR-SHR). Two days prior to testing, the animals are surgically implemented with catheters into a carotid artery and the jugular vein (PE50 polyethylene tubing) connected via a PE10 polyethylene tubing to a selected silicone tubing (size 0.020 ID×0.037 OD×0.008 wall) for blood pressure measurement and test compound delivery, respectively. The animals are allowed to recover with appropriate post operative care.

On the day of the experiment, the animals are placed in their cages and the catheters are connected via a swivel to a calibrated pressure transducer. After 1 hour of acclimation, a baseline measurement is taken over a period of at least five minutes. The animals are then dosed i.v. with vehicle or test compound in ascending cumulative doses every 60 minutes followed by a 0.3 mL saline to clear the catheter after each dose. Data is recorded continuously for the duration of the study using Notocord software (Kalamazoo, Mich.) and stored as electronic digital signals. In some studies, the effects of a single intravenous or oral (gavage) dose are monitored for at least 6 hours after dosing. Parameters measured are blood pressure (systolic, diastolic and mean arterial pressure) and heart rate.

Assay 5

In Vivo Evaluation of Antihypertensive Effects in the Conscious DOCA-Salt Rat Model of Hypertension CD rats (male, adult, 200-300 grams, Charles River Laboratory, USA) are allowed a minimum of 48 hours acclimation upon arrival at the testing site before they are placed on a high salt diet.

One week after the start of the high salt diet, a DOCA-salt pellet (100 mg, 21 days release time, Innovative Research of America, Sarasota, Fla.) is implanted subcutaneously and unilateral nephrectomy is performed. On 16 or 17 days post DOCA-salt pellet implantation, animals are implanted surgically with catheters into a carotid artery and the jugular vein with a PE50 polyethylene tubing, which in turn was connected via a PE10 polyethylene tubing to a selected silicone tubing (size 0.020 ID×0.037 OD×0.008 wall) for blood pressure measurement and test compound delivery, respectively. The animals are allowed to recover with appropriate post operative care.

On the day of the experiment, each animal is kept in its cage and connected via a swivel to a calibrated pressure transducer. After 1 hour of acclimation, a baseline measurement is taken over a period of at least five minutes. The animals are then dosed i.v. with a vehicle or test compound in escalating cumulative doses every 60 minutes followed by 0.3 mL of saline to flush the catheter after each dose. In some studies, the effects of a single intravenous or oral (gavage) dose is tested and monitored for at least 6 hours after dosing. Data is recorded continuously for the duration of the study using Notocord software (Kalamazoo, Mich.) and stored as electronic digital signals. Parameters measured are blood pressure (systolic, diastolic and mean arterial pressure) and heart rate. For cumulative and single dosing, the percentage change in mean arterial pressure (MAP, mmHg) or heart rate (HR, bpm) is determined as described for Assay 4.

While the present invention has been described with reference to specific aspects or embodiments thereof, it will be understood by those of ordinary skilled in the art that various changes can be made or equivalents can be substituted without departing from the true spirit and scope of the invention. Additionally, to the extent permitted by applicable patent statues and regulations, all publications, patents and patent applications cited herein are hereby incorporated by reference in their entirety to the same extent as if each document had been individually incorporated by reference herein.

What is claimed is:

1. A compound of formula I:

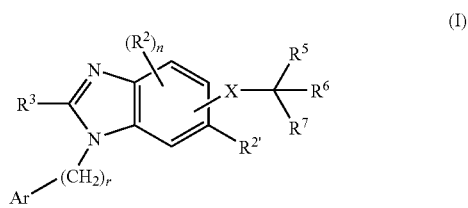

wherein:

r is 0, 1 or 2;

Ar is:

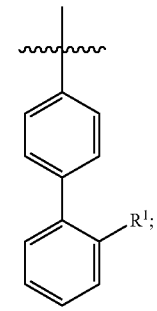

$R^1$ is selected from —COOR$^{1a}$, —NHSO$_2$R$^{1b}$, —SO$_2$NHR$^{1d}$, —SO$_2$OH, —C(O)NH—SO$_2$R$^{1c}$, —P(O)(OH)$_2$, —CN, —OCH(R$^{1e}$)—COOH, tetrazol-5-yl, and

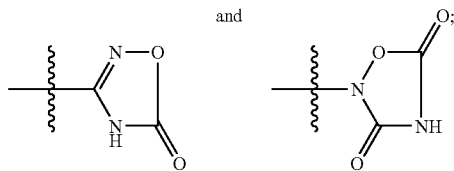

$R^{1a}$ is H, —C$_{1-6}$alkyl, —C$_{1-3}$alkylenearyl, —C$_{1-3}$alkyleneheteroaryl, —C$_{3-7}$cycloalkyl, —CH(C$_{1-4}$-alkyl)OC(O)R$^{1aa}$, —C$_{0-6}$alkylenemorpholine,

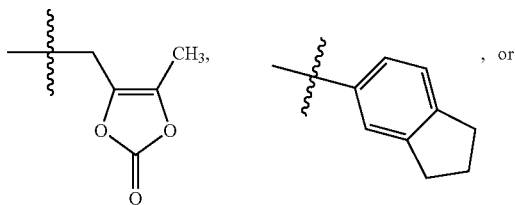

-continued

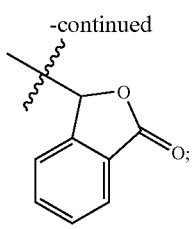

$R^{1aa}$ is —$C_{1-6}$alkyl, —O—$C_{3-7}$cycloalkyl, —NR$^{1ab}$R$^{1ac}$, or —CH(NH$_2$)CH$_2$COOCH$_3$; R$^{1ab}$ and R$^{1ac}$ are independently H, —$C_{1-6}$alkyl, or benzyl, or are taken together as —(CH$_2$)$_{3-6}$—; R$^{1b}$ is R$^{1c}$ or —NHC(O)R$^{1c}$; R$^{1c}$ is —$C_{1-6}$alkyl, —$C_{0-6}$alkylene-O—R$^{1ca}$, —$C_{1-5}$alkylene-NR$^{1cb}$R$^{1cc}$, —$C_{0-4}$alkylenearyl, or —$C_{0-4}$alkyleneheteroaryl; R$^{1ca}$ is H, —$C_{1-6}$alkyl, or —$C_{1-6}$alkylene-O—$C_{1-6}$alkyl; R$^{1cb}$ and R$^{1cc}$ are independently H or —$C_{1-6}$alkyl, or are taken together as —(CH$_2$)$_2$—O—(CH$_2$)$_2$— or —(CH$_2$)$_2$—N[C(O)CH$_3$]-(CH$_2$)$_2$—; R$^{1d}$ is H, R$^{1c}$, —C(O)R$^{1c}$, or —C(O)NHR$^{1c}$; R$^{1e}$ is —$C_{1-4}$alkyl or aryl;

n is 0, 1, or 2;

each R$^2$ is independently selected from halo, —NO$_2$, —$C_{1-6}$ alkyl, —$C_{2-6}$alkenyl, —$C_{3-7}$cycloalkyl, —CN, —C(O)R$^{2a}$, —$C_{0-5}$alkylene-OR$^{2b}$, —$C_{0-5}$alkylene-NR$^{2c}$R$^{2d}$, —$C_{0-3}$alkylenearyl, and —$C_{0-3}$alkyleneheteroaryl; R$^{2a}$ is H, —$C_{1-6}$alkyl, —$C_{3-7}$cycloalkyl, —OR$^{2b}$, or —NR$^{2c}$R$^{2d}$; R$^{2b}$ is H, —$C_{1-6}$alkyl, —$C_{3-7}$cycloalkyl, or —$C_{0-1}$alkylenearyl; and R$^{2c}$ and R$^{2d}$ are independently H, —$C_{1-4}$alkyl, or —$C_{0-1}$alkylenearyl;

R$^{2'}$ is selected from H and R$^2$;

R$^3$ is selected from —$C_{1-10}$alkyl, —$C_{2-10}$alkenyl, —$C_{3-10}$alkynyl, —$C_{0-3}$alkylene-$C_{3-7}$cycloalkyl, —$C_{2-3}$alkenylene-$C_{3-7}$cycloalkyl, —$C_{2-3}$alkynylene-$C_{3-7}$cycloalkyl, —$C_{0-5}$alkylene-NR$^{3a}$—$C_{0-5}$alkylene-R$^{3b}$, —$C_{0-5}$alkylene-O—$C_{0-5}$alkylene-R$^{3b}$, —$C_{1-5}$alkylene-S—$C_{1-5}$alkylene-R$^{3b}$, and —$C_{0-5}$alkylenearyl; R$^{3a}$ is H, —$C_{1-6}$alkyl, —$C_{3-7}$cycloalkyl, or —$C_{0-3}$alkylenearyl; and R$^{3b}$ is H, —$C_{1-6}$alkyl, —$C_{3-7}$cycloalkyl, —$C_{2-4}$alkenyl, —$C_{2-4}$alkynyl, or aryl;

X is —C(O)—NH—;

R$^5$ is selected from —$C_{0-3}$alkylene-SR$^{5a}$, —$C_{0-3}$alkylene-C(O)NR$^{5b}$R$^{5c}$, and —$C_{0-3}$alkylene-NR$^{5b}$—C(O)R$^{5d}$; R$^{5a}$ is H or —C(O)—R$^{5aa}$; R$^{5aa}$ is —$C_{1-6}$alkyl, —$C_{0-6}$alkylene-$C_{3-7}$cycloalkyl, —$C_{0-6}$alkylenearyl, —$C_{0-6}$alkyleneheteroaryl, —$C_{0-6}$alkylenemorpholine, —$C_{0-6}$alkylenepiperazine-CH$_3$, —CH[N(R$^{5ab}$)$_2$]-aa where aa is an amino acid side chain, -2-pyrrolidine, —$C_{0-6}$alkylene-OR$^{5ab}$, —OC$_{0-6}$alkylenearyl, —$C_{1-2}$alkylene-OC(O)—$C_{1-6}$alkyl, —$C_{1-2}$alkylene-OC(O)—$C_{0-6}$alkylenearyl, or —$C_{1-2}$alkylene-OC(O)—OC$_{1-6}$alkyl; R$^{5ab}$ is independently H or —$C_{1-6}$alkyl; R$^{5b}$ is H, —OH, —OC(O)R$^{5ba}$, —CH$_2$COOH, —O-benzyl, -pyridyl, or —OC(S)NR$^{5bb}$R$^{5bc}$; R$^{5ba}$ is H, —$C_{1-6}$alkyl, aryl, —OCH$_2$-aryl, —CH$_2$O-aryl, or —NR$^{5bb}$R$^{5bc}$; R$^{5bb}$ and R$^{5bc}$ are independently H or —$C_{1-4}$alkyl; R$^{5c}$ is H, —$C_{1-6}$alkyl, or —C(O)—R$^{5ca}$; R$^{5ca}$ is H, —$C_{1-6}$alkyl, —$C_{3-7}$cycloalkyl, aryl, or heteroaryl; and R$^{5d}$ is H, —$C_{1-4}$alkyl, —$C_{0-3}$alkylenearyl, —NR$^{5da}$R$^{5db}$, —CH$_2$SH, or —O—$C_{1-6}$alkyl; R$^{5da}$ and R$^{5db}$ are independently H or —$C_{1-4}$alkyl;

R$^6$ is selected from —$C_{1-6}$alkyl, —CH$_2$—O—(CH$_2$)$_2$OCH$_3$, —$C_{1-6}$alkylene-O—$C_{1-6}$alkyl, —$C_{0-3}$alkylenearyl, —$C_{0-3}$alkyleneheteroaryl, and —$C_{0-3}$alkylene-$C_{3-7}$ cycloalkyl; and R$^7$ is H or is taken together with R$^6$ to form —$C_{3-8}$cycloalkyl;

wherein each —CH$_2$— group in —(CH$_2$)$_r$— is optionally substituted with 1 or 2 substituents independently selected from —$C_{1-4}$alkyl and fluoro;

each alkyl and each aryl in R$^1$, R$^2$, R$^{2'}$, R$^3$, and R$^{5-6}$ is optionally substituted with 1 to 7 fluoro atoms;

each ring in Ar and each aryl and heteroaryl in R$^1$, R$^2$, R$^{2'}$, R$^3$, and R$^{5-6}$ is optionally substituted with 1 to 3 substituents independently selected from —OH, —$C_{1-6}$alkyl, —$C_{2-4}$alkenyl, —$C_{2-4}$alkynyl, —CN, halo, —O—$C_{1-6}$alkyl, —S—$C_{1-6}$alkyl, —S(O)—$C_{1-6}$alkyl, —S(O)$_2$—$C_{1-4}$alkyl, -phenyl, —NO$_2$, —NH$_2$, —NH—$C_{1-6}$alkyl, and —N($C_{1-6}$alkyl)$_2$, wherein each alkyl, alkenyl and alkynyl is optionally substituted with 1 to 5 fluoro atoms;

or a pharmaceutically acceptable salt thereof.

2. The compound of claim 1, wherein r is 1.

3. The compound of claim 1, wherein R$^1$ is —COOH, —NHSO$_2$R$^{1b}$, —SO$_2$NHR$^{1d}$, —SO$_2$OH, —C(O)NH—SO$_2$R$^{1c}$, —P(O)(OH)$_2$, —CN, —O—CH(R$^{1e}$)—COOH, tetrazol-5-yl,

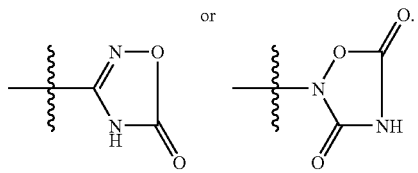

4. The compound of claim 3, wherein R$^1$ is —COOH or tetrazol-5-yl.

5. The compound of claim 1, wherein R$^1$ is —COOR$^{1a}$, and R$^{1a}$ is —$C_{1-6}$alkyl, —$C_{1-3}$alkylenearyl, —$C_{1-3}$alkyleneheteroaryl, —$C_{3-7}$cycloalkyl, —CH($C_{1-4}$alkyl)OC(O)R$^{1aa}$, —$C_{0-6}$alkylenemorpholine,

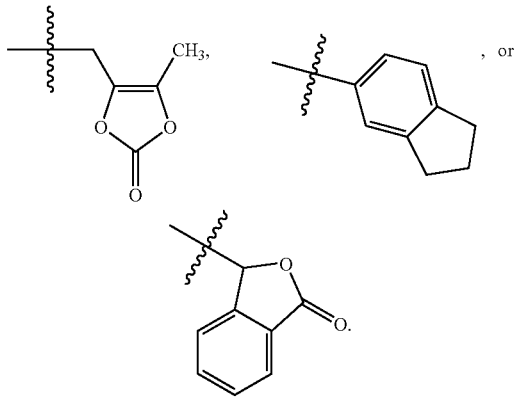

6. The compound of claim 1, wherein n is 0 or n is 1 and R$^2$ is —$C_{1-6}$alkyl.

7. The compound of claim 1, wherein R$^{2'}$ is H or —C(O)R$^{2a}$, where R$^{2a}$ is —$C_{1-6}$alkyl.

8. The compound of claim 1, wherein R$^3$ is —$C_{1-10}$alkyl or —$C_{0-5}$alkylene-O—$C_{0-5}$alkylene-R$^{3b}$, where R$^{3b}$ is H.

9. The compound of claim 1, wherein R$^{5a}$ is H, R$^{5b}$ is —OH, R$^{5c}$ is H, and R$^{5d}$ is H.

10. The compound of claim 1, wherein R$^{5a}$ is —C(O)—R$^{5aa}$; and R$^{5b}$ is H, —OC(O)R$^{5ba}$, —CH$_2$COOH, —O-benzyl, -pyridyl, or —OC(S)NR$^{5bb}$R$^{5bc}$.

11. The compound of claim 9, wherein R¹ is —COOH, —NHSO₂R¹ᵇ, —SO₂NHR¹ᵈ, —SO₂OH, —C(O)NH—SO₂R¹ᶜ, —P(O)(OH)₂, —CN, —O—CH(R¹ᵉ)—COOH, tetrazol-5-yl,

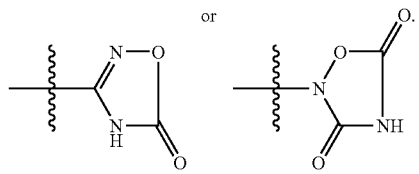

12. The compound of claim 10, wherein R¹ is —COOR¹ᵃ, and R¹ᵃ is —C₁₋₆alkyl, —C₁₋₃alkylenearyl, —C₁₋₃alkyleneheteroaryl, —C₃₋₇cycloalkyl, —CH(C₁₋₄alkyl)OC(O)R¹ᵃᵃ, —C₀₋₆alkylenemorpholine,

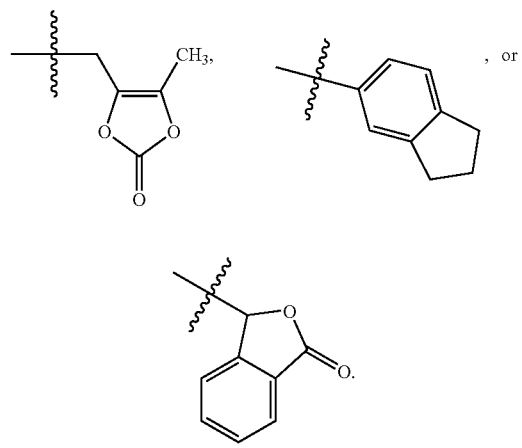

13. The compound of claim 9, wherein R¹ is —COOR¹ᵃ, and R¹ᵃ is —C₁₋₆alkyl, —C₁₋₃alkylenearyl, —C₁₋₃alkyleneheteroaryl, —C₃₋₇cycloalkyl, —CH(C₁₋₄alkyl)OC(O)R¹ᵃᵃ, —C₀₋₆alkylenemorpholine,

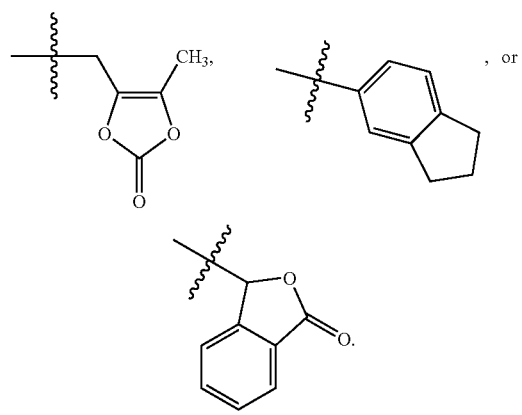

14. The compound of claim 10, wherein R¹ is —COOH, —NHSO₂R¹ᵇ, —SO₂NHR¹ᵈ, —SO₂OH, —C(O)NH—SO₂R¹ᶜ, —P(O)(OH)₂, —CN, —O—CH(R¹ᵉ)—COOH, tetrazol-5-yl,

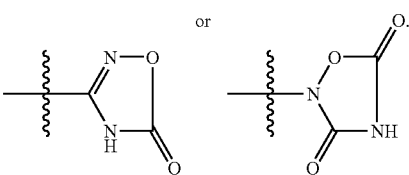

15. The compound of claim 1, wherein R⁶ is selected from —C₁₋₆alkyl and —C₀₋₃alkylenearyl.

16. The compound of claim 1, wherein R⁷ is H.

17. The compound of claim 1, wherein Ar is substituted with one fluoro atom.

18. The compound of claim 1, of the formula selected from:

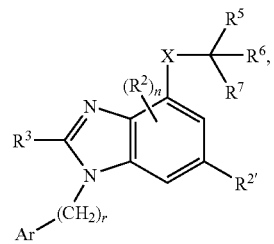
(Ia)

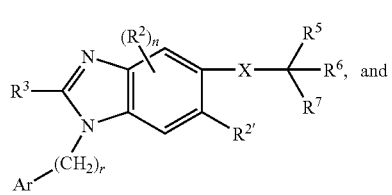
(Ib)

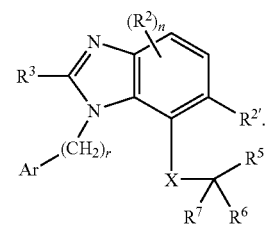
(Ic)

19. The compound of claim 1, of the formula

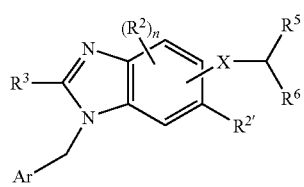
(II)

wherein R¹ is selected from —COOH and tetrazol-5-yl; n is 0, or n is 1 and R² is —C₁₋₆alkyl; R²' is selected from H and —C(O)—C₁₋₆alkyl; R³ is selected from —C₁₋₁₀alkyl and —C₀₋₅alkylene-O—C₁₋₅alkylene-H; R⁵ is selected from —C₀₋₃alkylene-SR⁵ᵃ and —C₀₋₃alkylene-C(O)NR⁵ᵇR⁵ᶜ; R⁵ᵃ is H or —C(O)—C₁₋₆alkyl; R⁵ᵇ is H, —OH, or —OC(O)—C₁₋₆alkyl; R⁵ᶜ is H or —C₁₋₆alkyl; and R⁶ is —C₁₋₆alkyl or —C₀₋₃alkylenearyl.

20. The compound of claim 19, of the formula selected from:

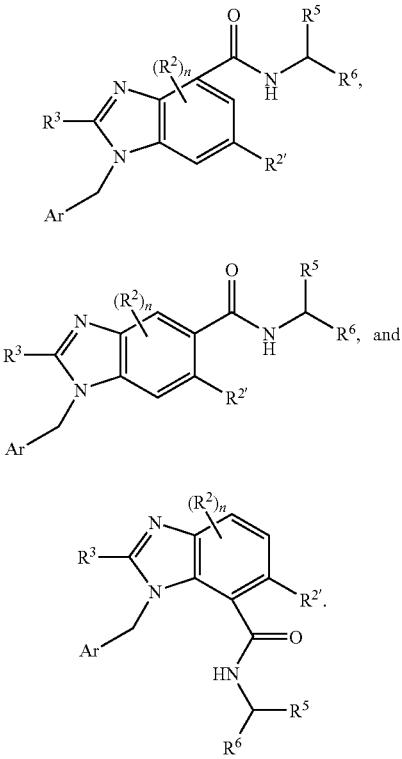

(IIa)

(IIb)

(IIc)

21. A pharmaceutical composition comprising a compound of claim 1 and a pharmaceutically acceptable carrier.

22. The pharmaceutical composition of claim 21, further comprising a therapeutic agent selected from the group consisting of diuretics, $\beta_1$ adrenergic receptor blockers, calcium channel blockers, angiotensin-converting enzyme inhibitors, $AT_1$ receptor antagonists, neprilysin inhibitors, non-steroidal anti-inflammatory agents, prostaglandins, anti-lipid agents, anti-diabetic agents, anti-thrombotic agents, renin inhibitors, endothelin receptor antagonists, endothelin converting enzyme inhibitors, aldosterone antagonists, angiotensin-converting enzyme/neprilysin inhibitors, vasopressin receptor antagonists, and combinations thereof.

23. An intermediate selected from the group consisting of:

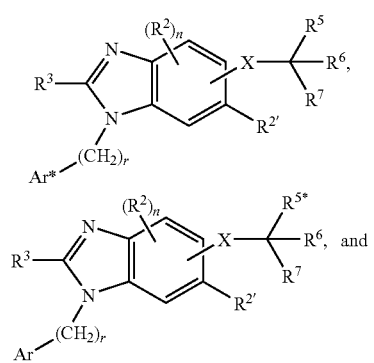

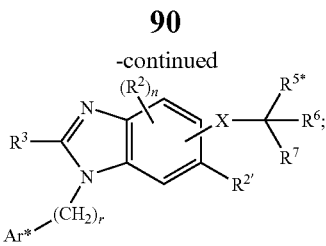

where Ar* is:

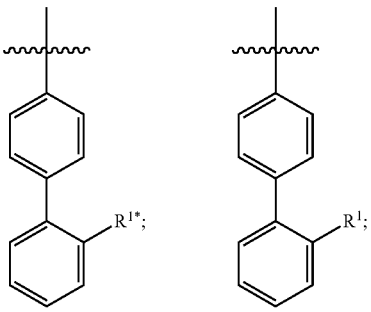

Ar is:

$R^1$ is selected from —$COOR^{1a}$, —$NHSO_2R^{1b}$—$SO_2NHR^{1d}$, —$SO_2OH$, —$C(O)NH$—$SO_2R^{1c}$, —$P(O)(OH)_2$, —$CN$, —$OCH(R^{1e})$—$COOH$, tetrazol-5-yl,

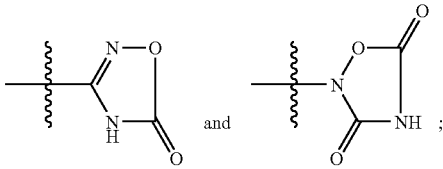

$R^{1a}$ is H, —$C_{1-6}$ alkyl, —$C_{1-3}$ alkylenearyl, —$C_{1-3}$ alkyleneheteroaryl, —$C_{3-7}$cycloalkyl, —$CH(C_{1-4}alkyl)OC(O)R^{1aa}$, —$C_{0-6}$alkylenemorpholine,

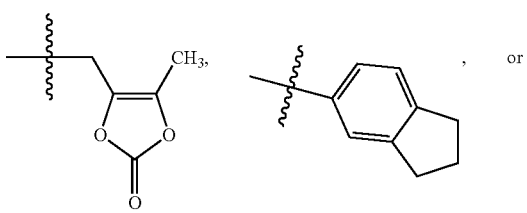

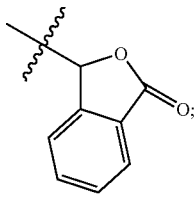

$R^{1aa}$ is —$O$—$C_{1-6}$alkyl, —$O$—$C_{3-7}$cycloalkyl, —$NR^{1ab}R^{1ac}$, or —$CH(NH_2)CH_2COOCH_3$; $R^{1ab}$ and $R^{1ac}$ are independently H, —$C_{1-6}$alkyl, or benzyl, or are taken together as —$(CH_2)_{3-6}$—; $R^{1b}$ is $R^{1c}$ or —$NHC(O)R^{1c}$; $R^{1c}$ is —$C_{1-6}$alkyl, —$C_{0-6}$alkylene-O—$R^{1ca}$, —$C_{1-5}$alkylene-$NR^{1cb}R^{1cc}$, —$C_{0-4}$alkylenearyl, or —$C_{0-4}$alkyleneheteroaryl; $R^{1ca}$ is H, —$C_{1-6}$alkyl, or —$C_{1-6}$alkylene-O—$C_{1-6}$alkyl; $R^{1cb}$ and $R^{1cc}$ are independently H or —$C_{1-6}$alkyl, or are taken together as —$(CH_2)_2$—O—$(CH_2)_2$— or —$(CH_2)_2$—N[C(O)CH$_3$]—$(CH_2)_2$—; $R^{1d}$ is H, $R^{1c}$, —C(O)$R^{1c}$, or —C(O)NH$R^{1c}$; $R^{1e}$ is —$C_{1-4}$alkyl or aryl;

$R^{1*}$ is selected from —C(O)O—P$^2$, —SO$_2$O—P$^5$, —SO$_2$NH—P$^6$, —P(O)(O—P$^7$)$_2$, —OCH(CH$_3$)—C(O)O—P$^2$, —OCH(aryl)-C(O)O—P$^2$, and tetrazol-5-yl-P$^4$;

r is 0, 1 or 2;

n is 0, 1, or 2;

each $R^2$ is independently selected from halo, —NO$_2$, —$C_{1-6}$ alkyl, —$C_{2-6}$alkenyl, —$C_{3-7}$cycloalkyl, —CN, —C(O)$R^{2a}$, —$C_{0-5}$alkylene-O$R^{2b}$, —$C_{0-5}$alkylene-N$R^{2c}R^{2d}$, —$C_{0-3}$alkylenearyl, and —$C_{0-3}$alkyleneheteroaryl; $R^{2a}$ is H, —$C_{1-6}$alkyl, —$C_{3-7}$cycloalkyl, —O$R^{2b}$, or —N$R^{2c}R^{2d}$; $R^{2b}$ is H, —$C_{1-6}$alkyl, —$C_{3-7}$cycloalkyl, or —$C_{0-1}$alkylenearyl; and $R^{2c}$ and $R^{2d}$ are independently H, —$C_{1-4}$alkyl, or —$C_{0-1}$alkylenearyl;

$R^{2'}$ is selected from H and $R^2$;

$R^3$ is selected from —$C_{1-10}$alkyl, —$C_{2-10}$alkenyl, —$C_{3-10}$alkynyl, —$C_{0-3}$alkylene-$C_{3-7}$cycloalkyl, —$C_{2-3}$alkenylene-$C_{3-7}$cycloalkyl, —$C_{2-3}$alkynylene-$C_{3-7}$cycloalkyl, —$C_{0-5}$alkylene-N$R^{3a}$—$C_{0-5}$alkylene-$R^{3b}$, —$C_{0-5}$alkylene-O—$C_{0-5}$alkylene-$R^{3b}$, —$C_{1-5}$alkylene-S—$C_{1-5}$alkylene-$R^{3b}$, and —$C_{0-3}$alkylenearyl; $R^{3a}$ is H, —$C_{1-6}$alkyl, —$C_{3-7}$cycloalkyl, or —$C_{0-3}$alkylenearyl; and $R^{3b}$ is H, —$C_{1-6}$alkyl, —$C_{3-7}$cycloalkyl, —$C_{2-4}$alkenyl, —$C_{2-4}$alkynyl, or aryl;

X is —C(O)—NH—;

$R^5$ is selected from —$C_{0-3}$alkylene-S$R^{5a}$, —$C_{0-3}$alkylene-C(O)N$R^{5b}R^{5c}$, and —$C_{0-3}$alkylene-N$R^{5b}$—C(O)$R^{5d}$; $R^{5a}$ is H or —C(O)—$R^{5aa}$; $R^{5aa}$ is —$C_{1-6}$alkyl, —$C_{0-6}$alkylene-$C_{3-7}$cycloalkyl, —$C_{0-6}$alkylenearyl, —$C_{0-6}$alkyleneheteroaryl, —$C_{0-6}$alkylenemorpholine, —$C_{0-6}$alkylenepiperazine-CH$_3$, —CH[N($R^{5ab}$)$_2$]-aa where aa is an amino acid side chain, -2-pyrrolidine, —$C_{0-6}$alkylene-O$R^{5ab}$, —OC$_{0-6}$alkylenearyl, —$C_{1-2}$alkylene-OC(O)—$C_{1-6}$alkyl, —$C_{1-2}$alkylene-OC(O)—$C_{0-6}$alkylenearyl, or —$C_{1-2}$alkylene-OC(O)—OC$_{1-6}$alkyl; $R^{5ab}$ is independently H or —$C_{1-6}$alkyl; $R^{5b}$ is H, —OH, —OC(O)$R^{5ba}$, —CH$_2$COOH, —O-benzyl, -pyridyl, or —OC(S)N$R^{5bb}R^{5bc}$; $R^{5ba}$ is H, —$C_{1-6}$alkyl, aryl, —OCH$_2$-aryl, —CH$_2$O-aryl, or —N$R^{5bb}R^{5bc}$; $R^{5bb}$ and $R^{5bc}$ are independently H or —$C_{1-4}$alkyl; $R^{5c}$ is H, —$C_{1-6}$alkyl, or —C(O)—$R^{5ca}$; $R^{5ca}$ is H, —$C_{1-6}$alkyl, —$C_{3-7}$-cycloalkyl, aryl, or heteroaryl; and $R^{5d}$ is H, —$C_{0-3}$alkylenearyl, —N$R^{5da}R^{5db}$, —CH$_2$SH, or —O—$C_{1-6}$alkyl; $R^{5da}$ and $R^{5db}$ are independently H or —$C_{1-4}$alkyl;

$R^{5*}$ is selected from —$C_{0-3}$alkylene-S—P$^3$, —$C_{0-3}$alkylene-C(O)NH(O—P$^5$), and —$C_{0-3}$alkylene-N(O—P$^5$)—C(O)$R^{5d}$;

$R^6$ is selected from —$C_{1-6}$ alkyl, —CH$_2$—O—$(CH_2)_2$OCH$_3$, —$C_{1-6}$ alkylene-O—$C_{1-6}$ alkyl, —$C_{0-3}$alkylenearyl, —$C_{0-3}$alkyleneheteroaryl, and —$C_{0-3}$alkylene-$C_{3-7}$ cycloalkyl; and $R^7$ is H or is taken together with $R^6$ to form —$C_{3-8}$cycloalkyl;

wherein each —CH$_2$— group in —(CH$_2$)$_r$— is optionally substituted with 1 or 2 substituents independently selected from —$C_{1-4}$alkyl and fluoro;

each alkyl and each aryl in $R^1$, $R^2$, $R^{2'}$, $R^3$, and $R^{5-6}$ is optionally substituted with 1 to 7 fluoro atoms;

each ring in Ar and each aryl and heteroaryl in $R^1$, $R^2$, $R^{2'}$, $R^3$, and $R^{5-6}$ is optionally substituted with 1 to 3 substituents independently selected from —OH, —$C_{1-6}$alkyl, —$C_{2-4}$alkenyl, —$C_{2-4}$alkynyl, —CN, halo, —O—$C_{1-6}$alkyl, —S—$C_{1-6}$alkyl, —S(O)—$C_{1-6}$alkyl, —S(O)$_2$—$C_{1-4}$alkyl, -phenyl, —NO$_2$, —NH, —NH—$C_{1-6}$alkyl, and —N($C_{1-6}$alkyl)$_2$, wherein each alkyl, alkenyl and alkynyl is optionally substituted with 1 to 5 fluoro atoms;

P$^2$ is a carboxy-protecting group; P$^3$ is a thiol-protecting group; P$^4$ is a tetrazole-protecting group; P$^5$ is a hydroxyl-protecting group; P$^6$ is a sulfonamide-protecting group; and P$^7$ is a phosphate-protecting group or phosphinate-protecting group;

or a salt thereof.

* * * * *

UNITED STATES PATENT AND TRADEMARK OFFICE
CERTIFICATE OF CORRECTION

| | | |
|---|---|---|
| PATENT NO. | : 8,212,052 B2 | Page 1 of 1 |
| APPLICATION NO. | : 12/330289 | |
| DATED | : July 3, 2012 | |
| INVENTOR(S) | : Seok-Ki Choi et al. | |

It is certified that error appears in the above-identified patent and that said Letters Patent is hereby corrected as shown below:

At Column 85, line 10,

" –$C_{1-6}$alkyl" should read " –O-$C_{1-6}$alkyl".

At Column 86, line 62,

"-$C_{0-5}$alkylene-O-$C_{0-5}$alkylene-$R^{3b}$"

should read "-$C_{0-5}$alkylene-O-$C_{1-5}$alkylene-$R^{3b}$".

At Column 90, lines 13-25, the structure below should appear after "Ar is:"

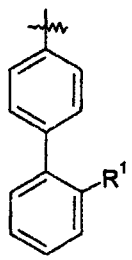

At Column 92, line 7, insert -- –$C_{1-4}$alkyl -- after "H".

Signed and Sealed this

Thirteenth Day of November, 2012

David J. Kappos
*Director of the United States Patent and Trademark Office*